(12) United States Patent
Diwu et al.

(10) Patent No.: US 8,927,224 B2
(45) Date of Patent: Jan. 6, 2015

(54) FLUORESCENT ION INDICATORS AND THEIR APPLICATIONS

(71) Applicant: AAT Bioquest, Inc., Sunnyvale, CA (US)

(72) Inventors: Zhenjun Diwu, Sunnyvale, CA (US); Jinfang Liao, Foster City, CA (US)

(73) Assignee: AAT Bioquest, Inc., Sunnyvale, CA (US)

(*) Notice: Subject to any disclaimer, the term of this patent is extended or adjusted under 35 U.S.C. 154(b) by 0 days.

(21) Appl. No.: 14/070,292

(22) Filed: Nov. 1, 2013

(65) Prior Publication Data
US 2014/0080170 A1 Mar. 20, 2014

Related U.S. Application Data

(60) Continuation of application No. 12/932,683, filed on Mar. 2, 2011, now Pat. No. 8,779,165, which is a division of application No. 12/040,753, filed on Feb. 29, 2008, now abandoned.

(60) Provisional application No. 60/923,452, filed on Apr. 13, 2007.

(51) Int. Cl.
| | |
|---|---|
| G01N 33/53 | (2006.01) |
| G01N 33/84 | (2006.01) |
| G01N 33/52 | (2006.01) |
| C07C 229/24 | (2006.01) |
| C07D 219/06 | (2006.01) |
| C07D 311/90 | (2006.01) |
| C07D 493/10 | (2006.01) |
| G01N 33/533 | (2006.01) |

(52) U.S. Cl.
CPC .............. *G01N 33/84* (2013.01); *C07C 229/24* (2013.01); *C07D 219/06* (2013.01); *C07D 311/90* (2013.01); *C07D 493/10* (2013.01); *G01N 33/533* (2013.01); *C07C 2103/24* (2013.01)
USPC ....................................................... 435/7.21

(58) Field of Classification Search
None
See application file for complete search history.

(56) References Cited

U.S. PATENT DOCUMENTS

| | | |
|---|---|---|
| 4,603,209 A | 7/1986 | Tsien et al. |
| 4,849,362 A | 7/1989 | DeMarinis |
| 4,945,171 A | 7/1990 | Haugland et al. |
| 5,049,673 A | 9/1991 | Tsien et al. |
| 5,134,232 A | 7/1992 | Tsien et al. |
| 5,227,487 A | 7/1993 | Haugland et al. |
| 5,380,836 A | 1/1995 | Rogart |
| 5,405,975 A | 4/1995 | Kuhn et al. |
| 5,436,128 A | 7/1995 | Harpold et al. |
| 5,439,828 A | 8/1995 | Masilamani et al. |
| 5,453,517 A | 9/1995 | Kuhn et al. |
| 5,459,276 A | 10/1995 | Kuhn et al. |
| 5,501,980 A | 3/1996 | Katerinopolous et al. |
| 5,516,911 A | 5/1996 | London et al. |

(Continued)

OTHER PUBLICATIONS

Adams, C.M.W., et al., "Permeability in Atherosclerosis," Atherosclerosis, 27, pp. 353-359 (1977).

(Continued)

*Primary Examiner* — Michael Pak

(57) ABSTRACT

Fluorescent dyes useful for preparing fluorescent metal ion indicators, the fluorescent indicators themselves, and the use of the fluorescent indicators for the detection, discrimination and quantification of metal cations.

16 Claims, 14 Drawing Sheets

(56) References Cited

U.S. PATENT DOCUMENTS

| | | | |
|---|---|---|---|
| 5,773,227 | A | 6/1998 | Kuhn et al. |
| 6,057,114 | A | 5/2000 | Akong et al. |
| 6,162,931 | A | 12/2000 | Gee et al. |
| 6,420,183 | B1 | 7/2002 | Krahn et al. |
| 2001/0006820 | A1* | 7/2001 | Knapp et al. .......... 436/172 |
| 2002/0164616 | A1 | 11/2002 | Martin et al. |

OTHER PUBLICATIONS

Bacci, J., et al., "Efficient Two-Step Synthesis of 9-Aryl-6-hydroxy-3H-xanthen-3-one Fluorophores," Org. Chem., 70, pp. 9051-9053 (2005).

Davis, H.W., and Sauter, R.W., "Fluorescence of Trypan Blue in Frozen-Dried Embryos of the Rat," Histochemistry, 54, pp. 177-189 (1977).

Eidelman, O., and Cabantchik, Z. 1., "Continuous Monitoring of Transport by Fluorescence on Cells and Vesicles," Biochim. Biophys. Acta, 988, pp. 319-334 (1989).

Gee, K., et al., "Detection and Imaging of Zinc Secretion from Pancreatic B-Cells Using a New Fluorescent Zinc Indicator," J. Am. Chem. Soc., 124, pp. 776-778 (2002).

Hathaway, W., et al., "The Acridine Orange Viability Test Applied to Bone Marrow Cells I. Correlation with Trypan Blue and Eosin Dye . . . ," Blook, 23, pp. 517-525 (2007).

Lakowicz, J. R., "Topics in Fluorescence Spectroscopy," vol. 4: Probe Design and Chemical Sensing; Plenum Press, New York & London (1994).

Martin, V., et al., "Fluorescent Sodium Ion Indicators Based on the 1,7-diaza-15-crown-5 system," Bioorg. Med. Chem. Lett., 14, pp. 5313-5316 (2004).

Molecular Probes Inc., Handbook of Fluorescent Probes and Research Chemicals, 7th edition, Chapter 1, Eugene, Oregon (1996-2007).

Online "http://www.interchim.fr/caUCalciumAssays.pdf Mar. 31, 2004—Fluo-8 AM." "[PDF] Calcium Assays—Interchim" accessed Sep. 16, 2013.

Online: http://www.teflabs.com/Portals/44052/docs/Fiuo-2-MA-Info-Packet1.pdf accessed Sep. 17, 2013.

Parham, W. E., and Bradscher, C. K., "Aromatic Organolithium Reagents Bearing Electrophilic Groups. Preparation by Halogen . . . ," Ace. Chem. Res., 15, pp. 300-305 (1982).

Chun et al., "D1-D2 Dopamine Receptor Synergy Promotes Calcium Signaling via Multiple Mechanisms", Molecular Pharmacology, vol. 84, pp. 190-200, (2013).

"Human CRAC (STIM1/ORAI1) Ion Channel Cell Line", Technical Data Sheet, PhotoScreen Ion Channel Cell Line, PerkinElmer, Inc., pp. 1-9, (2009).

Kurogi et al., "Green Tea Polyphenol Epigallocatechin Gallate Activates TRPA1 in an Intestinal Enteroendocrine Cell Line, STC-1", Chem. Senses, vol. 37, pp. 167-177, (2012).

Podust et al., "Extension of in vivo half-life of biologically active peptides via chemical conjugation to XTEN protein polymer", Protein Engineering, Design & Selection, vol. 26, No. 11, pp. 743-753, (2013).

Senbagavalli et al., "Immune Complexes Isolated from Patients with Pulmonary Tuberculosis Modulate the Activation and Function of Normal Granulocytes", Clinical and Vaccine Immunology, vol. 19, No. 12, pp. 1965-1971, (2012).

Vicini, Rino, "Study of calcium signaling by fluorescent imaging", Studienwoche Schweizer Jugend forscht, Universite De Geneve, (2011).

Minta et al., "Fluorescent Indicators for Cytosolic Calcium Based on Rhodamine and Fluorescein Chromophores", J Biol Chem (1989), 264(14):8171-8178.

* cited by examiner

FLUORESCENT ION INDICATORS AND THEIR APPLICATIONS

CROSS-REFERENCE TO RELATED APPLICATIONS

This application is a continuation of U.S. patent application Ser. No. 12/932,683, filed Mar. 2, 2011, which is a divisional of U.S. patent application Ser. No. 12/040,753, filed Feb. 29, 2008, which claims priority under 35 U.S.C. §119(e) to U.S. provisional patent application Ser. No. 60/923,452, filed Apr. 13, 2007, the disclosures of which are hereby incorporated by reference.

BACKGROUND

Metal ions play important roles in many biological systems. Cells utilize metal ions for a wide variety of functions, such as regulating enzyme activities, protein structures, cellular signaling, as catalysts, as templates for polymer formation and as regulatory elements for gene transcription. Metal ions can also have a deleterious effect when present in excess of bodily requirements or capacity to excrete. A large number of natural and synthetic materials are known to selectively or non-selectively bind to or chelate metal ions. Ion chelators are commonly used in solution for in vivo control of ionic concentrations and detoxification of excess metals, and as in vitro buffers. Ion chelators can be used as optical indicators of ions when bound to a fluorophore, and may be useful in the analysis of cellular microenvironments or dynamic properties of proteins, membranes and nucleic acids. For example, $Ca^{2+}$ ions play an important role in many biological events, and so the determination of intracellular $Ca^{2+}$ is an important biological application.

Fluorescent indicators utilizing a polycarboxylate BAPTA chelator have been predominantly used for intracellular calcium detections (see for example U.S. Pat. No. 4,603,209; U.S. Pat. No. 5,049,673; U.S. Pat. No. 4,849,362; U.S. Pat. No. 5,453,517; U.S. Pat. No. 5,501,980; U.S. Pat. No. 5,459,276; U.S. Pat. No. 5,501,980; U.S. Pat. No. 5,459,276; and U.S. Pat. No. 5,516,911; each of which is hereby incorporated by reference). Xanthene-based fluorescent calcium indicators (such as Fluo-3, Fluo-4 and Rhod-2 as represented by Formula 1) are the most common fluorescent indicators used in biological assays. However, these existing xanthene-based calcium indicators typically have low fluorescence quantum yields, resulting in low detection sensitivity). Furthermore their corresponding acetoxymethyl esters may not readily penetrate the membranes of live cells (thus requiring higher temperatures to achieve optimal dye loading), and once inside the cells, they exhibit a slow conversion to the corresponding BAPTA free acid.

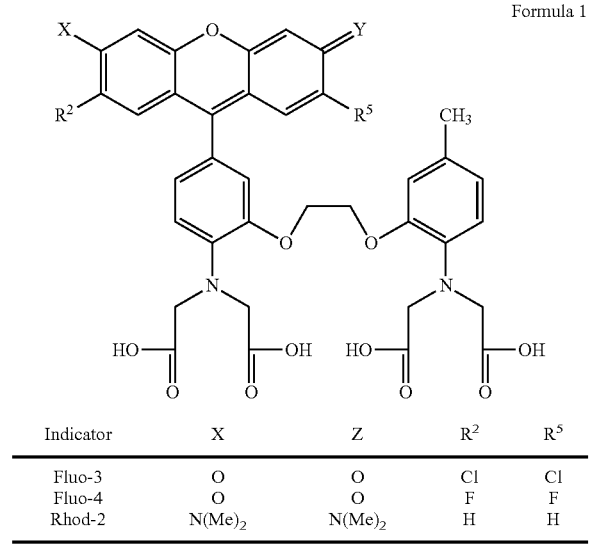

Formula 1

| Indicator | X | Z | $R^2$ | $R^5$ |
|---|---|---|---|---|
| Fluo-3 | O | O | Cl | Cl |
| Fluo-4 | O | O | F | F |
| Rhod-2 | $N(Me)_2$ | $N(Me)_2$ | H | H |

In view of the existing drawbacks for currently used xanthene-based fluorescent calcium indicators, what is needed are improved compositions and methods that offer sensitive detection of small variations in calcium concentrations, with a rapid response and a strong fluorescence signal. Also needed are fluorescent indicators that can be readily loaded into live cells. In addition, compositions and methods that are less susceptible to the effects of external changes (such as temperature) are preferred for high throughput screening and high content analysis.

The present application is directed to a family of fluorescent dyes that are useful for preparing fluorescent metal ion indicators. The indicators include a fluorophore and a ionophore, and are useful for the detection, discrimination and quantification of metal cations.

DEFINITIONS

Figure 1:
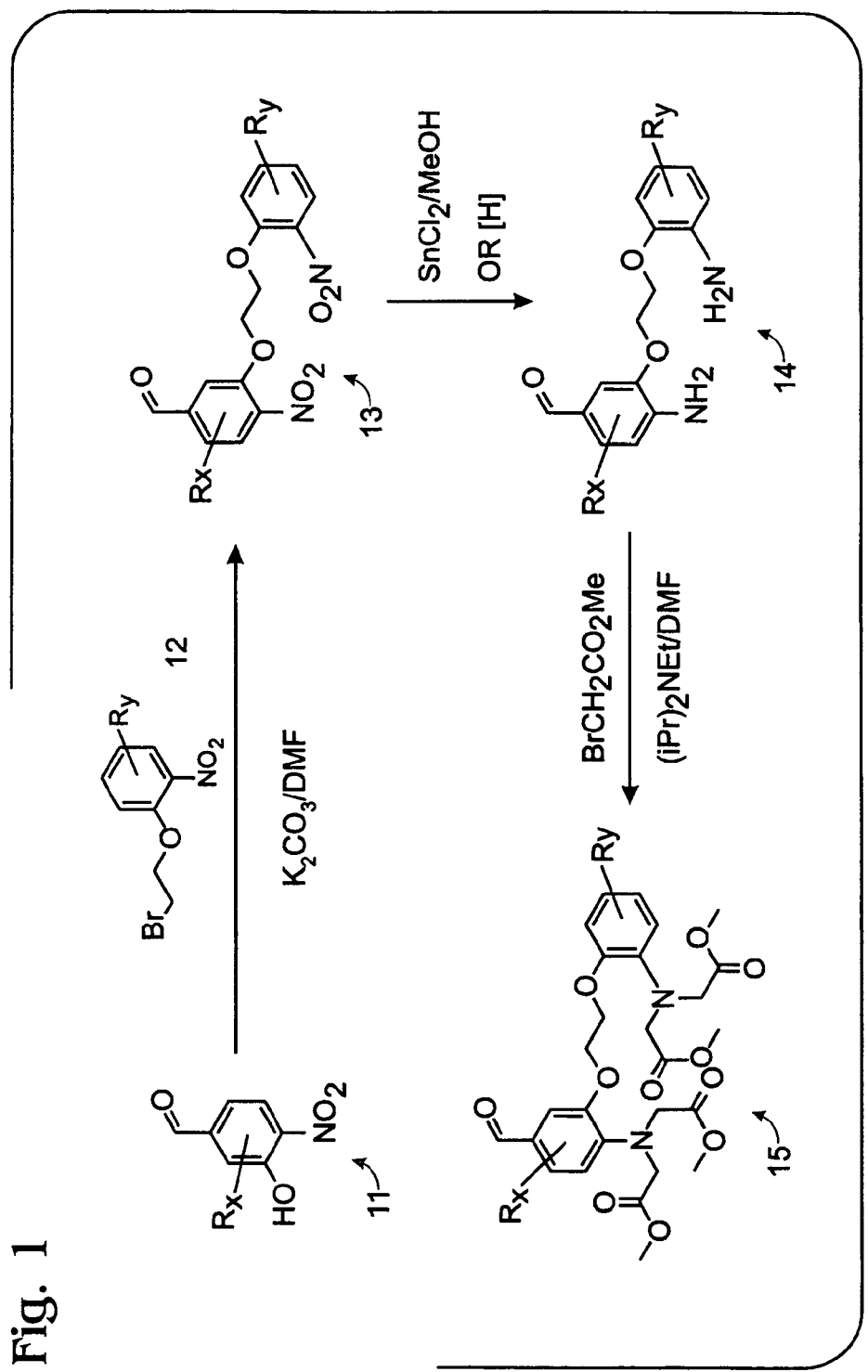
FIG. 1. A synthetic scheme for the preparation of selected BAPTA aldehyde compounds, where. $R_x$ and $R_y$ represent one or more substituents of each ring.

The following definitions are set forth to illustrate and define the meaning and scope of the various terms used to describe the invention herein.

The term "organic substituent", as used herein, refers to a carbon-containing organic radical that incorporates straight, branched chain or cyclic radicals having up to 50 carbons, unless the chain length or ring size is limited thereto. The organic substituent may include one or more elements of unsaturation, such as carbon-carbon double or triple bonds. Organic substituents may include alkyl, alkylene, alkenyl, alkenylene and alkynyl moieties, among others.

The term "alkyl," as used herein, by itself or as part of another group, refers to straight, branched chain or cyclic radicals having up to 50 carbons, unless the chain length or ring size is limited thereto, such as methyl, ethyl, propyl, cyclopropanyl, isopropyl, butyl, t-butyl, isobutyl, pentyl, hexyl, cyclohexyl, isohexyl, heptyl, 4,4-dimethylpentyl, octyl, 2,2,4-trimethylpentyl, nonyl, and decyl, among others.

The term "alkylene," as employed herein, by itself or as part of another group, refers to straight, branched chain or cyclic divalent radicals having up to 50 carbons, unless the chain length or ring size is limited thereto. Typical examples include methylene (—$CH_2$—), ethylene (—$CH_2CH_2$—), hexylene, heptylene, octylene, nonylene, and decylene, among others.

The term "alkenyl," as used herein, by itself or as part of another group, means a straight, branched chain or cyclic radical having 2-50 carbon atoms and one or more carbon-carbon double bonds, unless the chain length or ring size is limited thereto, such as ethenyl, 1-propenyl, 2-propenyl, 2-methyl-1-propenyl, 1-butenyl, and 2-butenyl, among others. The alkenyl chain may be 2 to 10 carbon atoms in length. Alternatively, the alkenyl chain may be 2 to 4 carbon atoms in length.

The term "alkenylene," as used herein, by itself or as part of another group, means straight, branched chain or cyclic divalent radical having 2-50 carbon atoms, unless the chain length or ring size is limited thereto, said straight, branched chain or cyclic radical containing at least one carbon-carbon double bond. Typical examples include ethenylene (—CH═CH—), propenylene (—CH═$CHCH_2$— and —$CH_2$CH═CH—), n-butenylene, and 3-methyl-2-pentenylene, hexenylene, heptenylene, octenylene, nonenylene, and decenylene, among others.

The term "alkynyl," as used herein, by itself or as part of another group, means a straight, branched chain or cyclic radical of 2-50 carbon atoms, unless the chain length or ring size is limited thereto, having at least one carbon-carbon triple bond between two of the carbon atoms in the chain, such as acetylenyl, 1-propynyl, and 2-propynyl, among others. The alkynyl chain may be 2 to 10 carbon atoms in length. Alternatively, the alkynyl chain may be from 2 to 4 carbon atoms in length.

The term "alkynylene" as used herein, by itself or as part of another group, means a straight, branched chain or cyclic divalent radical having 2-50 carbon atoms, unless the chain length or ring size is limited thereto, that contains at least one carbon-carbon triple bond. Typical examples include ethynylene (—C≡C—) propynylene (—C≡$CCH_2$— and —$CH_2$C≡C—), n-butynylene, 4-methyl-2-pentynylene, 1-butynylene, 2-butynylene, 3-butynylene, 4-butynylene, pentynylene, hexynylene, heptynylene, octynylene, nonynylene, and decynylene, among others.

The term "alkoxy" as used herein, by itself or as part of another group, refers to any of the above radicals linked via an oxygen atom. Typical examples include methoxy, ethoxy, isopropyloxy, sec-butyloxy, n-butyloxy, t-butyloxy, n-pentyloxy, 2-methylbutyloxy, 3-methylbutyloxy, n-hexyloxy, and 2-ethylbutyloxy, among others. Alkoxy also may include PEG groups (—$OCH_2CH_2O$—) or alkyl moieties that contain more than one oxygen atom.

The term "aryl," as employed herein, by itself or as part of another group, refers to an aryl or aromatic ring system containing 1 to 4 unsaturated rings (each ring containing 6 conjugated carbon atoms and no heteroatoms) that are optionally fused to each other or bonded to each other by carbon-carbon single bonds, that is optionally further substituted as described below. Examples of aryl ring systems include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Aryl substituents may include phenyl, substituted phenyl, naphthyl or substituted naphthyl.

The term "heteroaryl," as employed herein, by itself or as part of another group, refers to groups having 5 to 14 ring atoms; 6, 10 or 14 π electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, phenanthrolinyl, phenazinyl, isothiazolyl, phenothiazinyl, isoxazolyl, furazanyl, phenoxazinyl, and tetrazolyl groups).

Any aryl or heteroaryl ring system is unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

The terms "halogen" or "halo" as employed herein, by itself or as part of another group, refers to chlorine, bromine, fluorine or iodine.

The terms "AM ester" or "AM" as employed herein, by itself or as part of another group, refers to an acetoxymethyl ester of a carboxylic acid.

The terms "amino" or "amine" include $NH_2$, "monoalkylamine" or "monoalkylamino," and "dialkylamine" or "dialkylamino". The terms "monoalkylamine" and "monoalkylamino," "dialkylamine" and "dialkylamino as employed herein, by itself or as part of another group, refers to the group $NH_2$ where one hydrogen has been replaced by an alkyl group, as defined above.

The terms "dialkylamine" and "dialkylamino" as employed herein, by itself or as part of another group, refers to the group $NH_2$ where both hydrogens have been replaced by alkyl groups, as defined above.

The term "hydroxyalkyl," as employed herein, by itself or as part of another group, refers to an alkyl group where one or more hydrogens thereof are substituted by one or more hydroxyl moieties.

The term "haloalkyl," as employed herein, by itself or as part of another group, refers to an alkyl group where one or more hydrogens thereof are substituted by one or more halo moieties. Typical examples include chloromethyl, fluoromethyl, difluoromethyl, trifluoromethyl, trichloroethyl, trifluoroethyl, fluoropropyl, and bromobutyl, among others.

The term "haloalkenyl," as employed herein, by itself or as part of another group, refers to an alkenyl group where one or more hydrogens thereof are substituted by one or more halo moieties.

The term "haloalkynyl," as employed herein, by itself or as part of another group, refers to an alkynyl group where one or more hydrogens thereof are substituted by one or more halo moieties.

The term "carboxyalkyl," as employed herein, by itself or as part of another group, refers to an alkyl group where one or more hydrogens thereof are substituted by one or more carboxylic acid moieties.

The term "heteroatom" as used herein, by itself or as part of another group, means an oxygen atom ("O"), a sulfur atom ("S") or a nitrogen atom ("N"). It will be recognized that when the heteroatom is nitrogen, it may form an $NR_1R_2$ moiety, where $R_1$ and $R_2$ are, independently from one another, hydrogen or alkyl, or together with the nitrogen to which they are bound, form a saturated or unsaturated 5-, 6-, or 7-membered ring.

The term "chelator", "chelate", "chelating group", "ionophore", or "ionophoric moiety" as used herein, by itself or as part of another group, refers to a chemical moiety that binds to, or complexes with, one or more metal ions, such as lithium, calcium, sodium, magnesium, potassium, and/or other biologically important metal ions. The binding affinity of a chelator for a particular metal ion can be determined by measuring the dissociation constant between that chelator and that ion. Chelators may include one or more chemical moieties that bind to, or complex with, a cation or anion. Examples of suitable chelators include 1,2-Bis(2-aminophenoxy)ethane-N,N,N',N'-tetraacetic acid (BAPTA), bipyridyl (bipy); terpyridyl (terpy); ethylenediaminetetraacetic acid (EDTA); crown ethers; aza-crown ethers; succinic acid; citric acid; salicylic acids; histidines; imidazoles; ethyleneglycol-bis-(beta-aminoethyl ether)N,N'-tetraacetic acid (EGTA); nitroloacetic acid; acetylacetonate (acac); sulfate; dithiocarbamates; carboxylates; alkyldiamines; ethylenediamine (en); diethylenetriamine (dien); nitrate; nitro; nitroso; glyme; diglyme; bis(acetylacetonate)ethylenediamine (acacen); 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (OTTA), 1,4,7-triazacyclononanetriacetic acid (NOTA), 1,4,8,11-tetraazacyclotetra-decanetetraacetic acid (TETA), DOTA-N-(2-aminoethyl)amide; DOTA-N-(2-aminophenethyl)amide; and 1,4,8,11-tetraazacyclotetradecane, among others.

The term "BAPTA" or "1,2-Bis(2-aminophenoxy)ethane-N,N,N',N'-tetraacetic acid" as used herein, by itself or as part of another group, refers to the following ring structure or its derivatives, such as esters, amides, carbamates and so on:

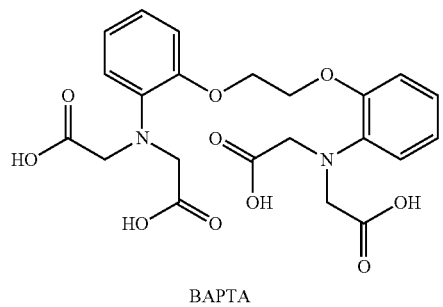 [SMILES: O=C(O)CN(CC(=O)O)c1ccccc1OCCOc1ccccc1N(CC(=O)O)CC(=O)O]

BAPTA

The term "fluorophore or fluorophore moiety" as used herein, by itself or as part of another group, means a molecule or a portion of a molecule which exhibits fluorescence. By fluorescence is meant that the molecule or portion of a molecule can absorb excitation energy having a given wavelength and emit energy at a different wavelength. The intensity and wavelength of the emitted energy depend on the fluorophore, the chemical environment of the fluorophore, and the specific excitation energy used. Exemplary fluorophores include, but are not limited to, fluoresceins, rhodamines, coumarins, oxazines, cyanines, pyrenes, and other polycyclic aromatic molecules.

The term "xanthene", or "xanthene derivative", as used herein, by itself or as part of another group, means any compounds or substituents that contain one or more of the following fused ring structures or its derivatives:

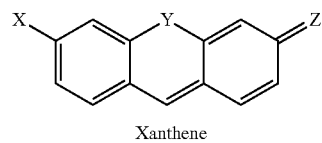

Xanthene (X, Z = O, S or Se or N; Y = O, S, Se, N or C)

The term "fluorescein" as used herein, by itself or as part of another group, means any compounds or substituents that contain one or more of the following fused ring structures or its derivatives:

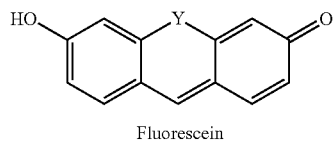

Fluorescein (Y = O, S, Se, N or C)

The term "rhodamine" as used herein, by itself or as part of another group, means any compounds or substituents that contain one or more of the following fused ring structures or its derivatives:

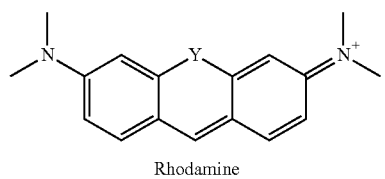

Rhodamine (Y = O, S, Se, N or C)

The term "rhodol" as used herein, by itself or as part of another group, means any compounds or substituents that contain one or more of the following fused ring structures or its derivatives:

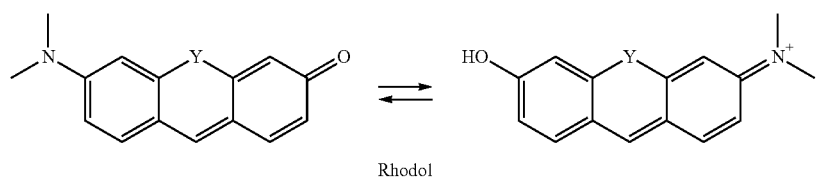

Rhodol (Y = O, S, Se, N or C)

The term "substituted," as used herein, refers to the formal replacement of a hydrogen on a chemical moiety or functional group with an alternative radical. Where a compound, chemical moiety or functional group is described as substituted, the alternative radical substituent moiety is generally selected from the group consisting of hydroxy, oxo, nitro, trifluoromethyl, halogen, alkoxy, alkylenedioxy, aminoalkyl, aminoalkoxy, amino, monoalkylamino, dialkylamino, alkylcarbonylamino, alkoxycarbonylamino, alkoxycarbonyl, carboxy, hydroxyalkoxy, alkoxyalkoxy, monoalkylaminoalkoxy, dialkylaminoalkoxymono(carboxyalkyl)amino, bis(carboxyalkyl)amino, alkoxycarbonyl, alkynylcarbonyl, alkylsulfonyl, alkenylsulfonyl, alkynylsulfonyl, arylsulfonyl, alkylsulfonyl, alkylsulfinyl, alkylsulfonamido, arylsulfonamido, alkylsulfonamido, carboxyalkoxy, carboxyalkyl, carboxyalkylamino, cyano, trifluoromethoxy, perfluoroethoxy, guanidine, amidino, oxyguanidino, alkylimino, formylimino, acyl nitrile, acyl azide, acetyl azide, dichlorotriazene, isothiocyante, sulfonyl halide, sulfosuccinimidyl ester, isocyante, acyl halide, aldehyde, haloacetamide, maleimido, aziridinyl, alkylthio (disulfide), acrylo, haloalkylcarbonyl, boronate, hydrazide, semicarbazide, carbohydrazide, arylalkyl, heteroarylalkyl, cycloalkylalkyl, cycloalkenylalkyl, cycloheteroalkylalkyl, and cycloheteroalkenylalkyl.

The term "indicator compound" refers to the compounds of the invention, specifically to those compounds having utility as fluorescent metal ion indicators, as well as their acylated or otherwise protected precursor compounds, such as the acetoxymethyl ester derivatives suitable for adding to samples containing biological cells.

The term "screening" refers to the testing and/or evaluation of a multiplicity of molecules or compounds for a selected property or therapeutic utility. Screening is typically a repetitive, or iterative, process. A multiplicity of candidate molecules may be screened for their ability to bind to a target molecule which is capable of denaturing and/or unfolding. For example, a multiplicity of candidate molecules may be evaluated for their ability to bind to a target molecule (e.g., a protein receptor) in a thermal shift assay. If none of a selected subset of molecules from the multiplicity of candidate molecules (for example, a combinatorial library) binds to the target molecule, then a different subset may be tested for binding in the thermal shift assay.

The term "high-throughput", as used herein, encompasses screening activity in which human intervention is minimized, and automation is maximized. For example, high-throughput screening may include any of a variety of automated processes, including for example the automation of pipetting, mixing, and/or heating, the software-controlled generation of thermal unfolding information, and the software-controlled comparisons of thermal unfolding information. Alternatively, a high-throughput method is one in which hundreds of compounds can be screened per 24 hour period by a single individual operating a single suitable apparatus.

DESCRIPTION OF THE PREFERRED EMBODIMENTS

The present application is directed to Fluorescent dyes useful for preparing fluorescent metal ion indicators, the fluorescent indicators themselves, and the use of the fluorescent indicators for the detection, discrimination and quantification of metal cations.

In one aspect of the invention, the compounds of the invention may be described by Formula 2, below:

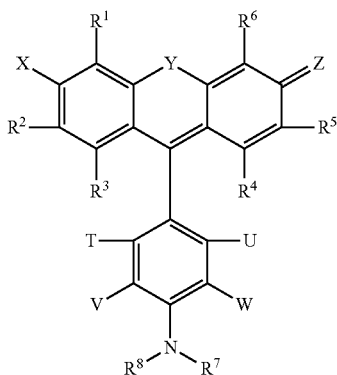

Formula 2

Substituents $R^1$-$R^6$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl, or heteroaryl; or alkyl, or alkoxy that is itself optionally substituted one or more times by halogen, amino, hydroxy, phosphonyl, sulfonyl, carbonyl, boronic acid, aryl or heteroaryl.

The heteroatom Y is independently selected from O, S, Se, $NR^9$ and $CR^{10}R^{11}$. The X and Z substituents are independently selected from O and $NR^{12}R^{13}$, where each $R^9$, $R^{10}$, $R^{11}$, $R^{12}$ and $R^{13}$ is independently H, an alkyl having 1-12 carbons, or carboxyalkyl.

The T and U substituents are independently selected from alkyl having 1-12 carbons, alkoxy having 1-12 carbons, aryloxy, amino, halogen, cyano, carboxy, carboxyalkyl, carbonyl, sulfonyl, phosphonyl, boronic acid, aryl, and heteroaryl.

The V and W are independently selected from $OR^{14}$, $SR^{15}$ or $NR^{12}R^{13}$, such that at least one of V or W, in combination with $NR^7R^8$, forms a metal chelator, where each $R^7$, $R^8$, and $R^{12}$-$R^{15}$ are independently H, an alkyl having 1-12 carbons, carboxyalkyl, alkoxy or aryloxy.

In one aspect of the invention X and Z are both O. In another aspect of the invention, X and Y are O, and Z is $NR^{12}R^{13}$. In yet another aspect of the invention, X, Y and Z are each O. Careful selection of the nature of the X, Y, and Z heteroatoms allows the spectral properties of the indicators to be tuned through the selection of the appropriate xanthene dye.

The compound of the invention may include exactly two fluorophores, which may be the same or different, and which may each be independently bound to the chelator by a covalent linkage L, or may be fused to the chelator moiety. Where the compound of the invention includes two fluorophores, the two fluorophores may result in an indicator compound that exhibits ratiometric spectral properties (such as Indo-1 or Fura-2).

The compounds of the present invention are xanthene-based metal ion indicators. The existing xanthene-based BAPTA calcium indicators are either fluorescein- (where X, Y and Z are O) or rhodamine- (where X and Z are N while Y is O) based structures such as Fluo-3, Fluo-4 and Rhod-2. The spectral properties of the existing xanthene-based ion indicators may be modulated by selecting substituents $R^1$-$R^6$, while the chelating properties of the indicator may be adjusted by selecting and/or modifying substituents j, k, m and n on the phenyl ring that is not conjugated to the xanthene ring.

The substituents T and U can play unexpectedly important roles in determining both the spectral properties and the chelating properties of the indicator compounds. Another unexpected discovery is that substituents $R^1$, $R^2$, $R^5$ and $R^6$ play important roles in controlling the cell loading and intracellular esterase-induced hydrolysis rate of acetoxymethyl (AM) esters of xanthene-based fluorescent BAPTA indicators. For example, the acetoxymethyl (AM) esters of xanthene-based BAPTA indicators are much more readily loaded into live cells when $R^1$, $R^2$, $R^5$ and $R^6$ are all hydrogen. The compounds of the present invention provide sensitive and selective xanthene-based fluorescent indicators for optical measurement of ion concentrations in cells. Furthermore, substituents T and U can be selected to provide the optimized spectral responses of xanthene-based fluorescent ion indicators for selective measurement of ions in cells. Careful selection of the $R^1$, $R^2$, $R^5$ and $R^6$ groups of acetoxymethyl (AM) esters of xanthene-based BAPTA indicators may result in optimal cell-loading properties.

In one aspect of the invention, the compounds of the invention can be described by Formula 3, below.

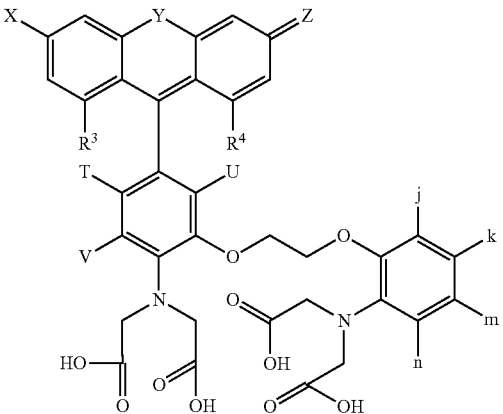

Formula 3

In the embodiment of formula 3, heteroatom Y is independently selected from O, S, Se, $NR^9$ and $CR^{10}R^{11}$. Substituents X and Z are independently selected from O and $NR^{12}R^{13}$ where each $R^9$, $R^{10}$, $R^{11}$, $R^{12}$ and $R^{13}$ are independently H or an alkyl having 1-12 carbons or carboxyalkyl. Substituents T and U are independently selected from an alkyl having 1-12 carbons, alkoxy having 1-12 carbons, aryloxy, amino, halogen, cyano, carboxy, carboxyalkyl, carbonyl, sulfonyl, phosphonyl, boronic acid, aryl and heteroaryl. $R^3$, $R^4$, j, k, m, n and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, alkoxy that is itself optionally substituted one or more times by halogen, amino, hydroxy, phosphonyl, sulfonyl, carbonyl, boronic acid, aryl or heteroaryl.

In another aspect of the invention, the compounds of the invention can be described by Formula 4, below.

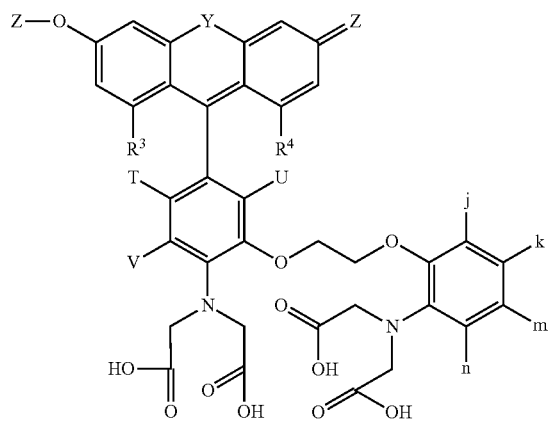

Formula 4

In this embodiment of the invention, the heteroatom Y is independently selected from O, S, Se, $NR^9$ and $CR^{10}R^{11}$. Z is acyl having less than 10 carbon atom or —$CH_2OAc$. $R^9$, $R^{10}$, $R^{11}$, $R^{12}$ and $R^{13}$ are independently H or alkyl having 1-12 carbons, or carboxyalkyl. T and U are independently selected from hydrogen, alkyl having 1-12 carbons, alkoxy having 1-12 carbons, aryloxy, amino, halogen, cyano, carboxy, carboxyalkyl, carbonyl, sulfonyl, phosphonyl, boronic acid, aryl, and heteroaryl. $R^3$, $R^4$, j, k, m, n and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention can be described by Formula 5, below.

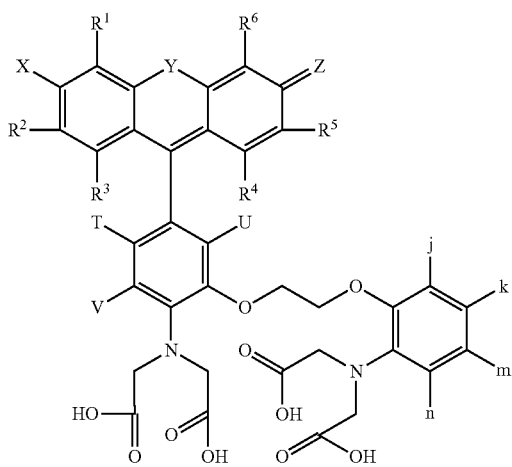

Formula 5

In this embodiment, the heteroatom Y is independently selected from O, S, Se, $NR^9$ and $CR^{10}R^{11}$. X and Z are independently selected from O or $NR^{12}R^{13}$, where each $R^9$, $R^{10}$, $R^{11}$, $R^{12}$ and $R^{13}$ is independently H or an alkyl having 1-12 carbons or carboxyalkyl. T and U are independently selected from an alkyl having 1-12 carbons, alkoxy having 1-12 carbons, aryloxy, amino, halogen, cyano, carboxy, carboxyalkyl, carbonyl, sulfonyl, phosphonyl, boronic acid, aryl and heteroaryl. $R^1$-$R^6$, j, k, m, n and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl or alkoxy that is itself optionally substituted one or more times by halogen, amino, hydroxy, phosphonyl, sulfonyl, carbonyl, boronic acid, aryl or heteroaryl. In this embodiment, the fluorophore moiety is typically a xanthene.

In yet another aspect of the invention, the compounds of the invention are fluorescent indicators which can be described by Formula 6, below.

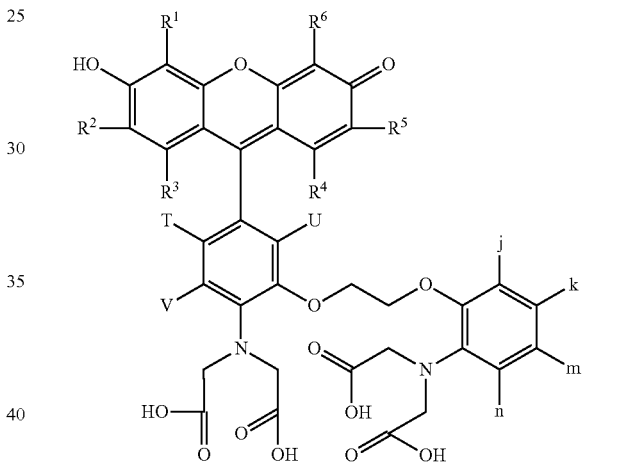

Formula 6

In this embodiment, the substituents T and U are independently selected from alkyl having 1-12 carbons, alkoxy having 1-12 carbons, aryloxy, amino, halogen, cyano, carboxy, carboxyalkyl, carbonyl, sulfonyl, phosphonyl, boronic acid, aryl or heteroaryl. $R^1$-$R^6$, j, k, m, n and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, alkoxy that is itself optionally substituted one or more times by halogen, amino, hydroxy, phosphonyl, sulfonyl, carbonyl, boronic acid, aryl or heteroaryl.

The disclosed indicator compounds typically exhibit low fluorescence quantum efficiency in the absence of metal ions. However, in the presence of increasing metal ion concentration the fluorescence quantum efficiency rises dramatically. For example, selected indicators of this family exhibit a fluorescence signal increase of over 100-times between zero and a saturating calcium concentration.

In yet another aspect of the invention, the compounds of the invention are fluorescent indicators which can be described by Formula 7, below.

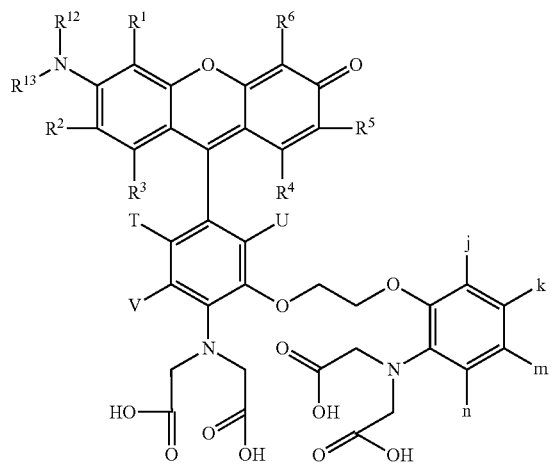

Formula 7

In this embodiment, substituents T and U are independently selected from alkyl having 1-12 carbons, alkoxy having 1-12 carbons, aryloxy, amino, halogen, cyano, carboxy, carboxyalkyl, carbonyl, sulfonyl, phosphonyl, boronic acid, aryl and heteroaryl. $R^1$-$R^6$, j, k, m, n and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. $R^{12}$ and $R^{13}$ are independently H or alkyl having 1-12 carbons or carboxyalkyl.

In yet another aspect of the invention, the compounds of the invention are fluorescent indicators which can be described by Formula 8, below.

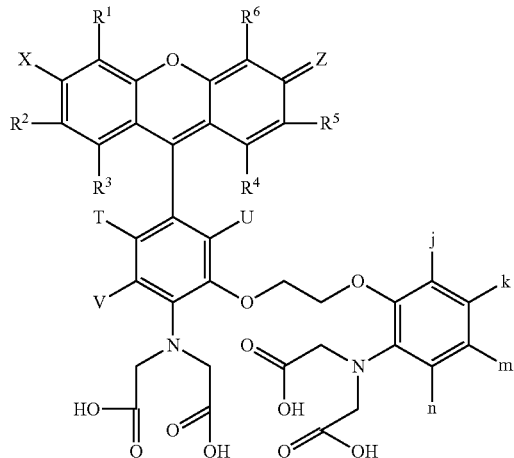

Formula 8

In this embodiment, substituents T and U are independently selected from alkyl having 1-12 carbons, alkoxy having 1-12 carbons, aryloxy, amino, halogen, cyano, carboxy, carboxyalkyl, carbonyl, sulfonyl, phosphonyl, boronic acid, aryl and heteroaryl. $R^1$-$R^6$, j, k, m, n and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. X and Z, which may be same or different, are independently selected from Nee, where $R^{12}$ and $R^{13}$ are independently H or alkyl having 1-12 carbons or carboxyalkyl.

In yet another aspect of the invention, the compounds of the invention are fluorescent indicators which can be described by Formula 9, below.

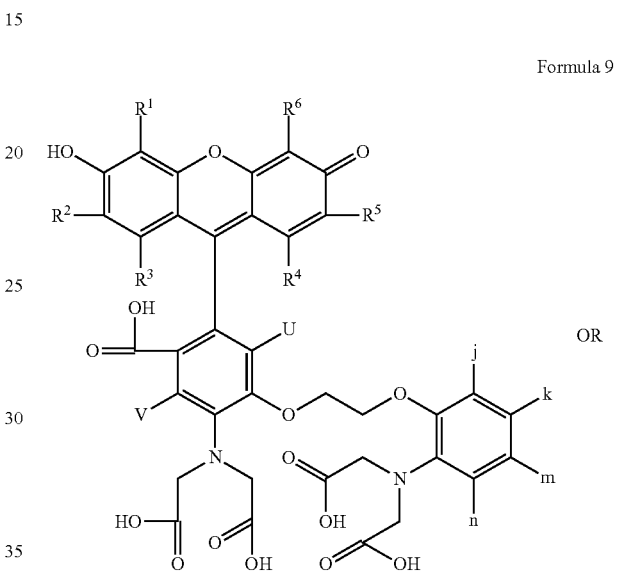

Formula 9

OR

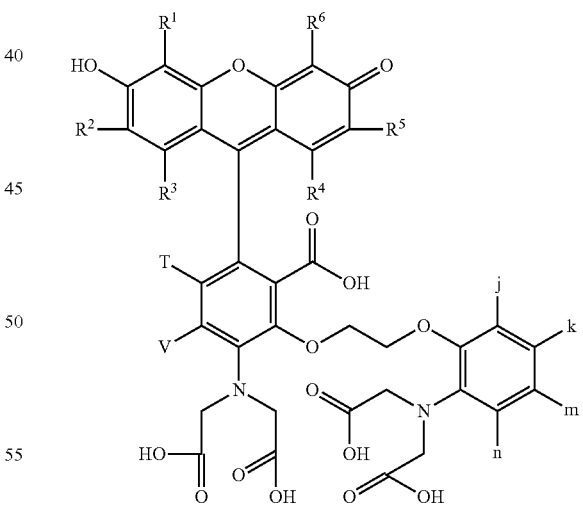

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 10, below.

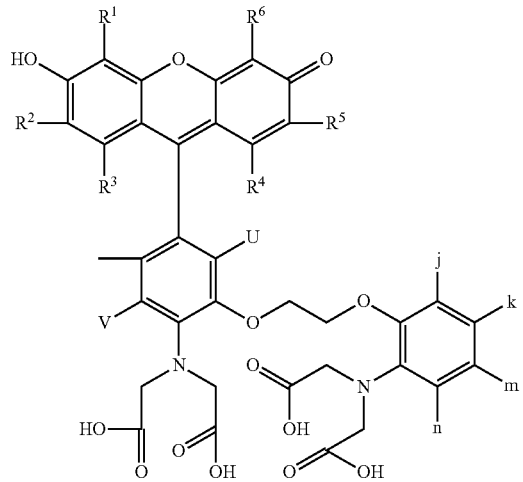

Formula 10

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In another aspect of the invention, the compounds of the invention are fluorescent indicators having Formula 11.

Formula 11

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 12, below.

Formula 12

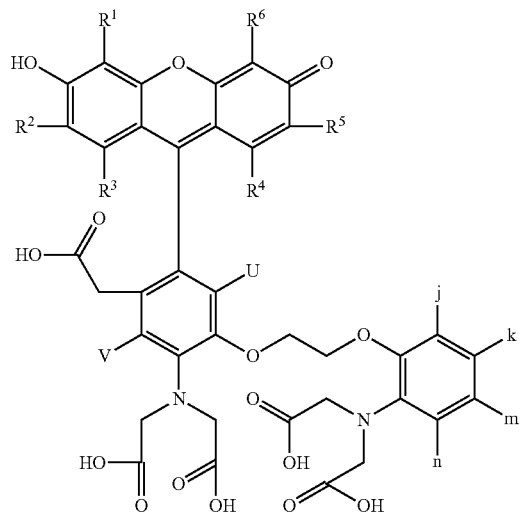

Formula 13

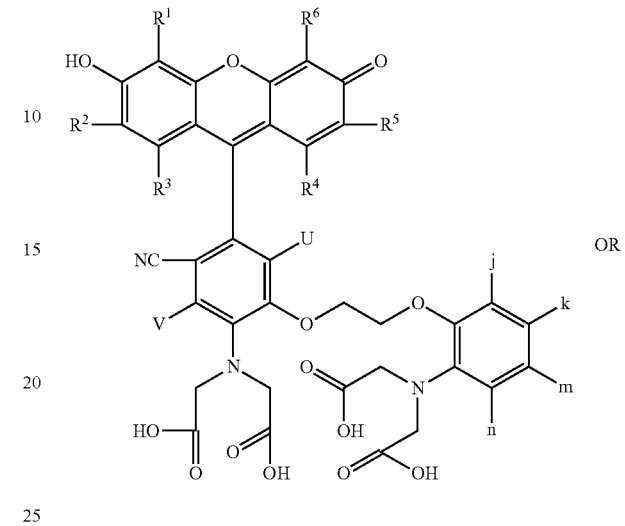

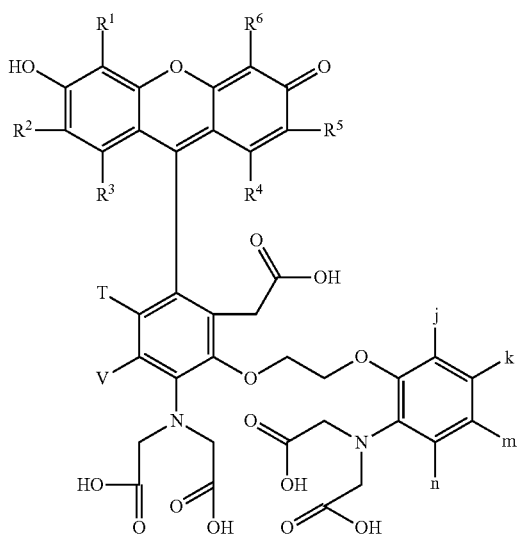

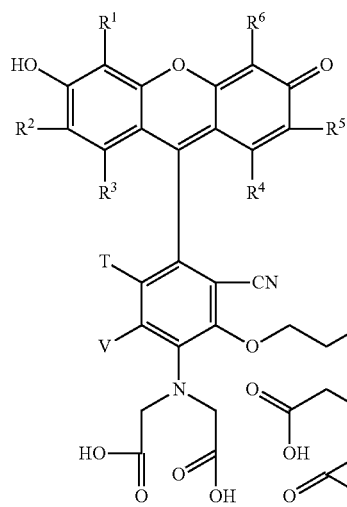

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 13, below.

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 14, below.

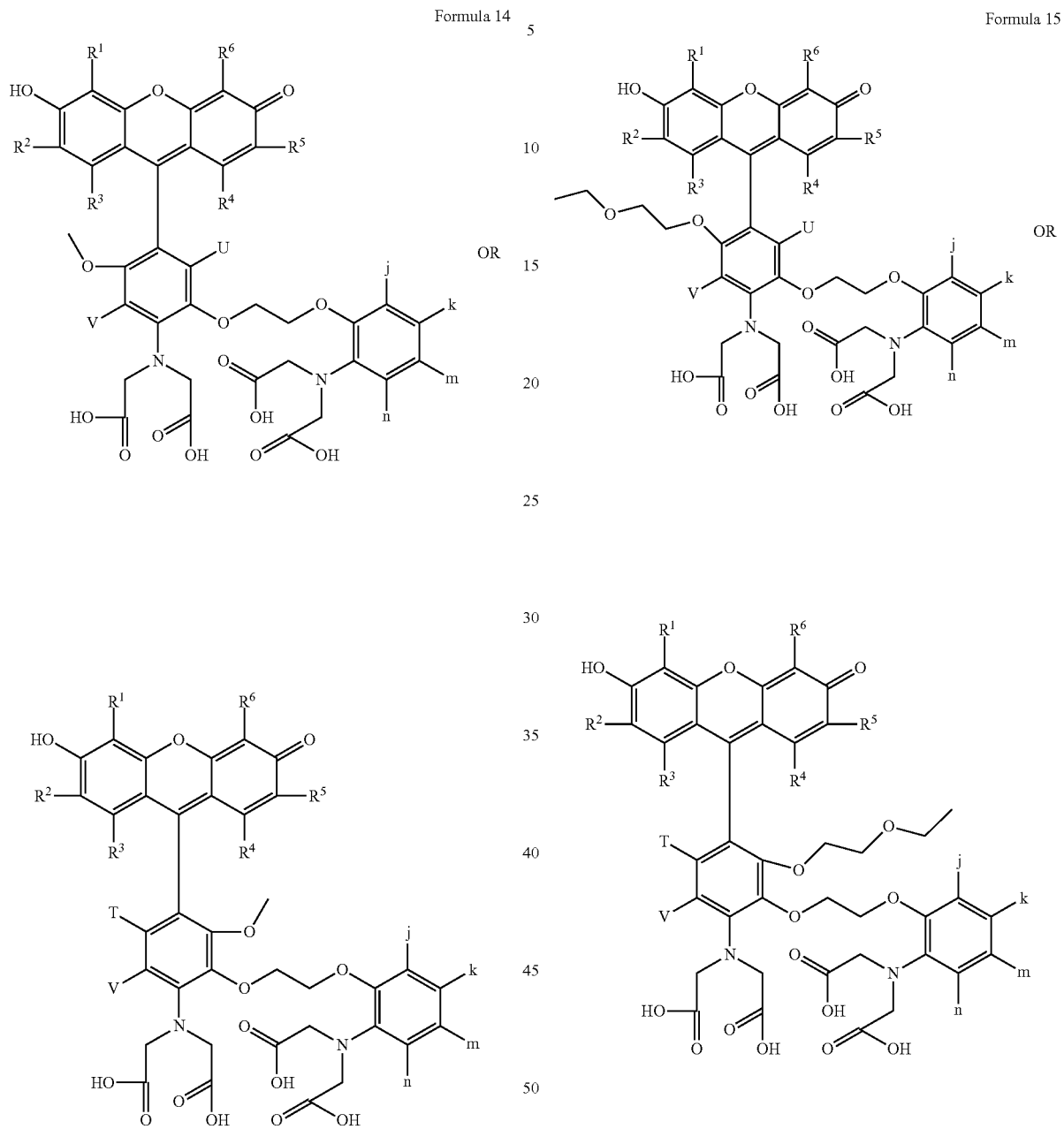

In this embodiment, $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 15.

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 16, below.

Formula 16

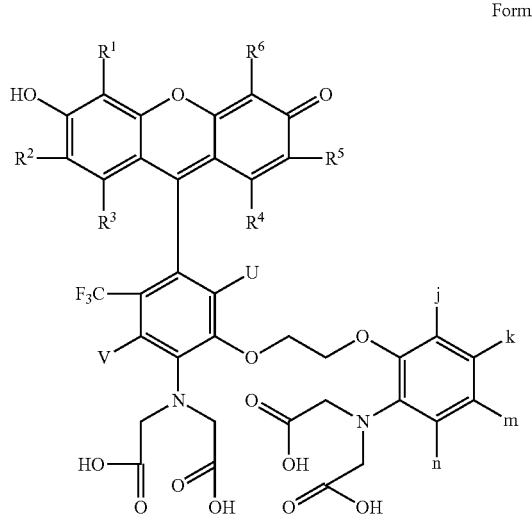

OR

Formula 17

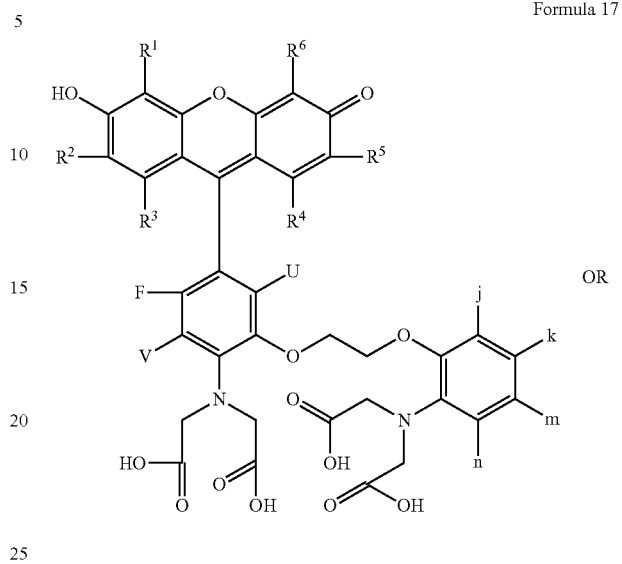

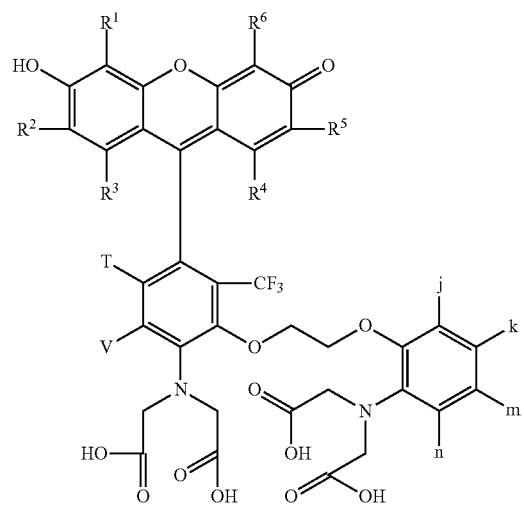

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 17, below.

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which may be described by Formula 18.

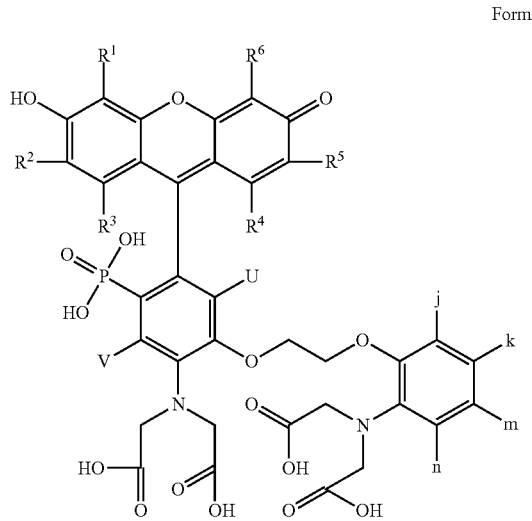

Formula 18

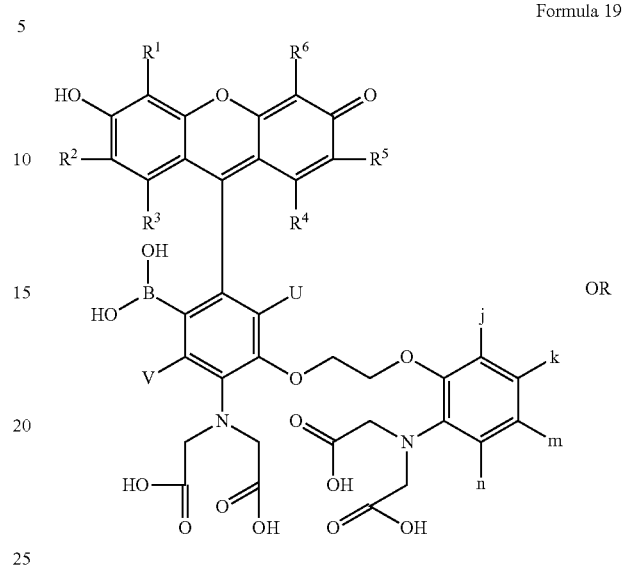

Formula 19

OR

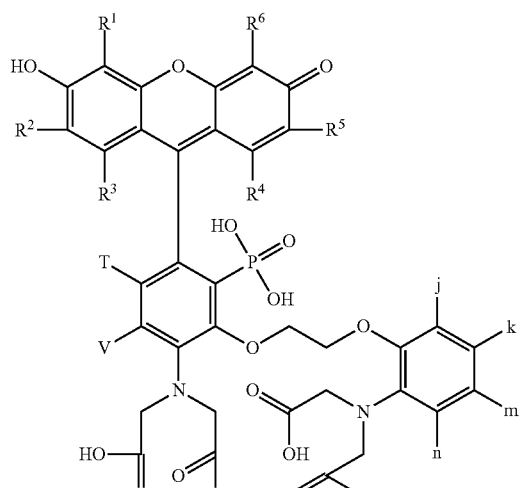

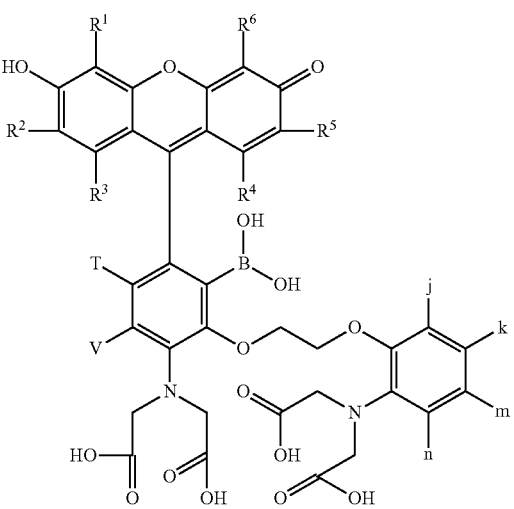

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 19, below.

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 20, below.

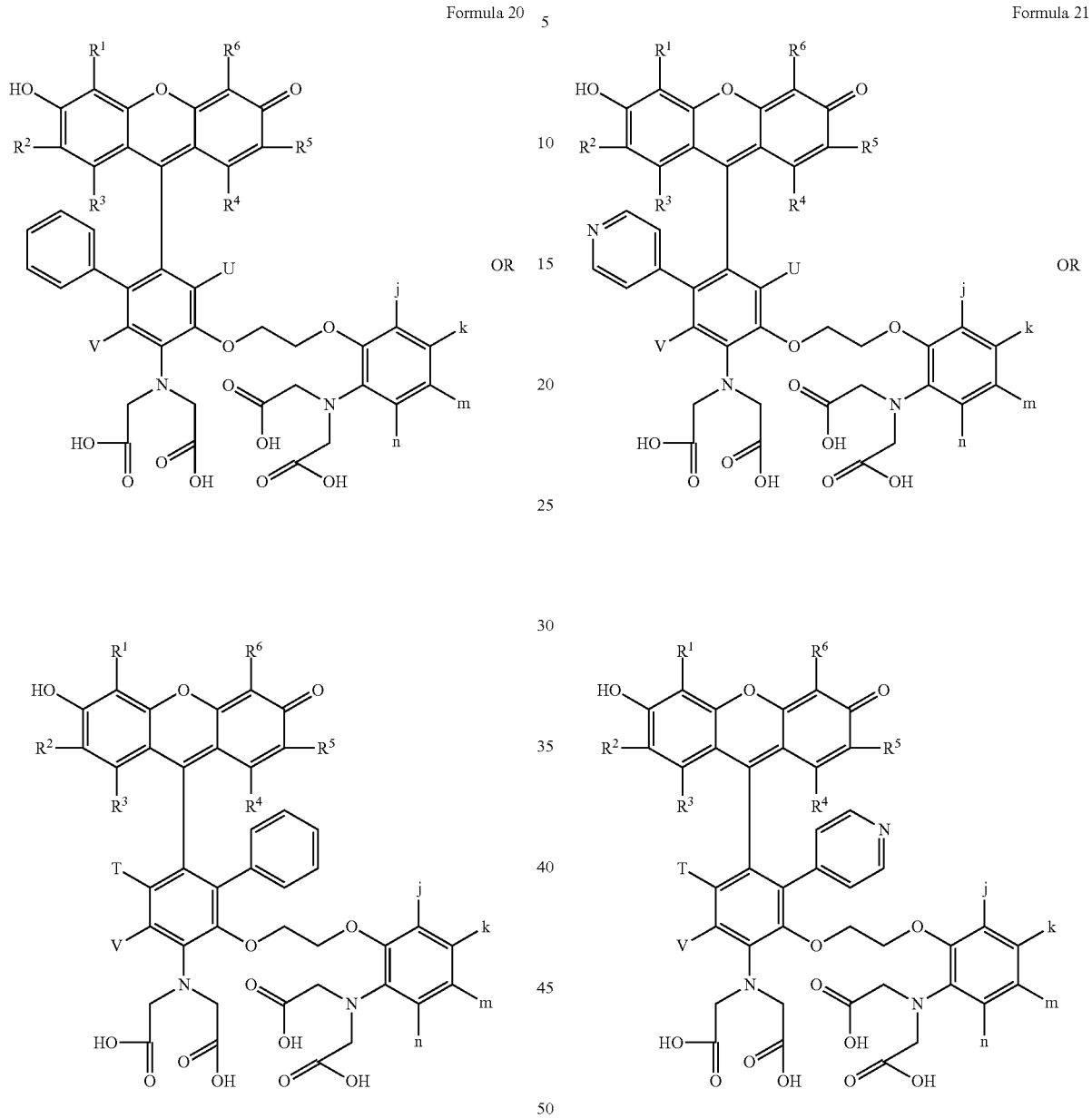

Formula 20 OR Formula 21 OR

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 21, below.

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 22, below.

Formula 22

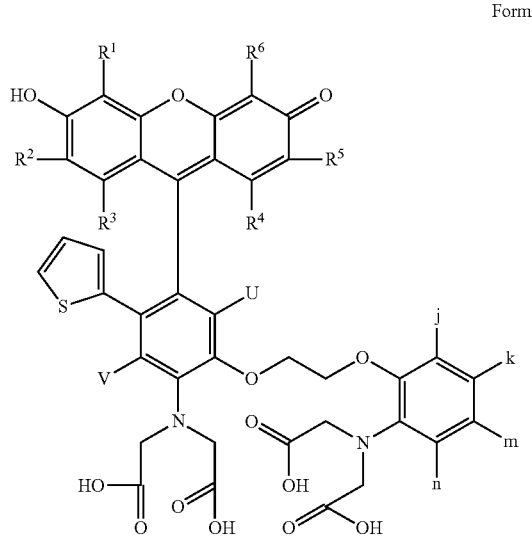

OR

Formula 23

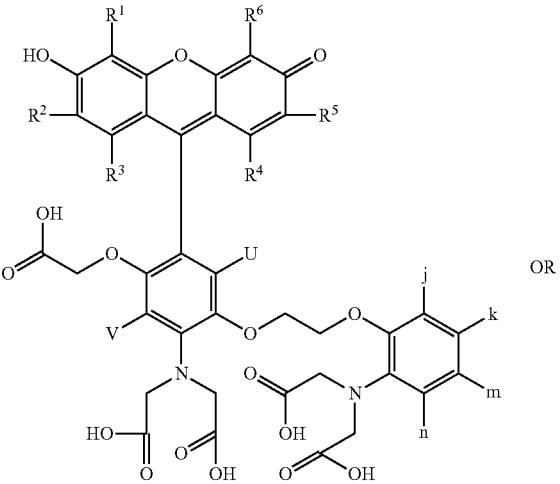

OR

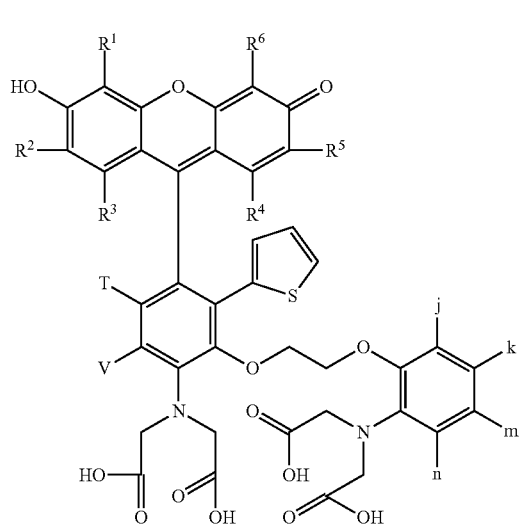

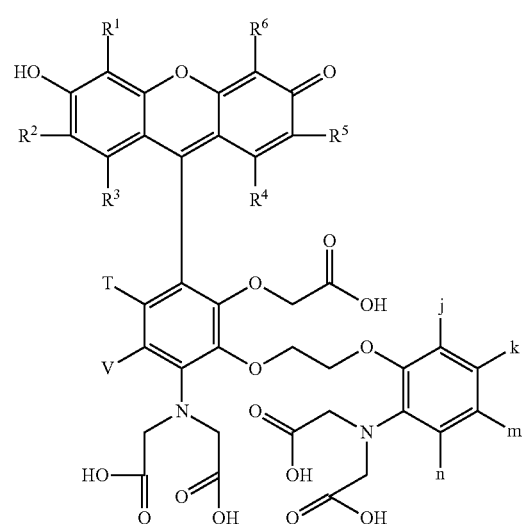

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 23, below.

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl.

In yet another aspect of the invention, the compounds of the invention are fluorescent indicators which can be described by Formula 24, below.

Formula 24

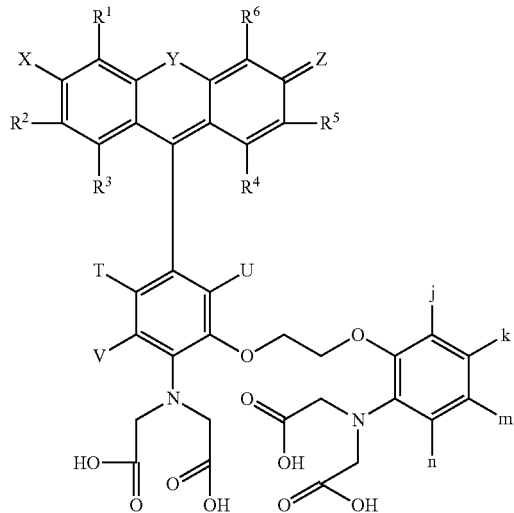

In this embodiment, heteroatom Y is $NR^9$ or $CR^{11}R^{12}$, where $R^9$, $R^{11}$ and $R^{12}$ are independently alkyl having 1-12 carbons, carboxyalkyl having 1-12 carbons, alkoxy having 1-12 carbons, a polyethylene glycol (PEG) moiety, aryloxy; or alkyl, or alkoxy that is itself optionally substituted one or more times by halogen, amino, hydroxy, phosphonyl, sulfonyl, carbonyl, boronic acid, aryl or heteroaryl. Substituents T and U are independently selected from H, alkyl having 1-12 carbons, alkoxy having 1-12 carbons, aryloxy, amino, halogen, cyano, carboxy, carboxyalkyl, carbonyl, sulfonyl, phosphonyl, boronic acid, aryl and heteroaryl. $R^1$-$R^6$, j, k, m, n and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. X and Z, which may be the same or different, are independently selected from O or $NR^{12}R^{13}$, where $R^{12}$ and $R^{13}$ are independently H or an alkyl having 1-12 carbons or carboxyalkyl having 2-12 carbons. In this embodiment, Y is typically N-alkyl where the alkyl group has 1-12 carbon atoms or $=C(alkyl)_2$, where each alkyl independently has 1-6 carbons. More, Preferably Y is NMe or $C(Me)_2$.

In yet another aspect of the invention, the compounds of the invention are fluorescent indicators which can be described by Formula 25, below.

Formula 25

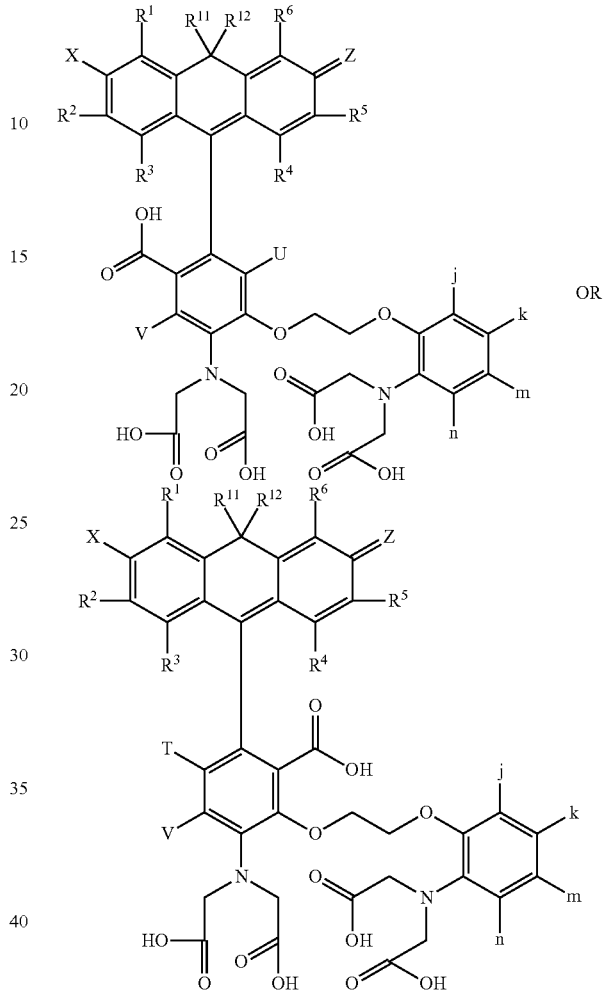

In this embodiment, substituents T and U are independently selected from H, alkyl having 1-12 carbons, alkoxy having 1-12 carbons, aryloxy, amino, halogen, cyano, carboxy, carboxyalkyl, carbonyl, sulfonyl, phosphonyl, boronic acid, aryl and heteroaryl. $R^1$-$R^6$, j, k, m, n and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. $R^{11}$ and $R^{12}$ are independently an alkyl having 1-12 carbons or carboxyalkyl, alkoxy having 1-12 carbons, PEG chain, aryloxy; or alkyl, alkoxy that is itself optionally substituted one or more times by halogen, amino, hydroxy, phosphonyl, sulfonyl, carbonyl, boronic acid, aryl or heteroaryl. X and Z, which may be the same or different, are independently selected from O and $NR^{13}R^{14}$, where $R^{13}$ and $R^{14}$ are independently H or alkyl having 1-12 carbons, or carboxyalkyl having 2-12 carbons. In this embodiment, $R^{13}$ and $R^{14}$ are typically lower alkyl or lower alkoxy having 1-12 carbon atoms. Preferably, $R^{13}$ and $R^{14}$ are methyl or ethyl.

In yet another aspect of the invention, the compounds of the invention are fluorescent indicators which can be described by Formula 26, below.

Formula 26

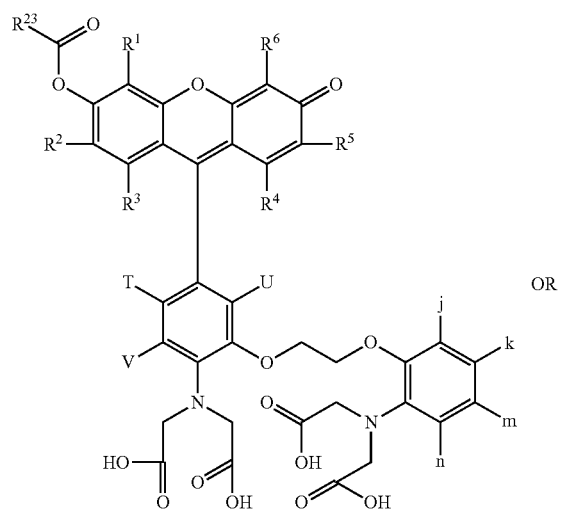

OR

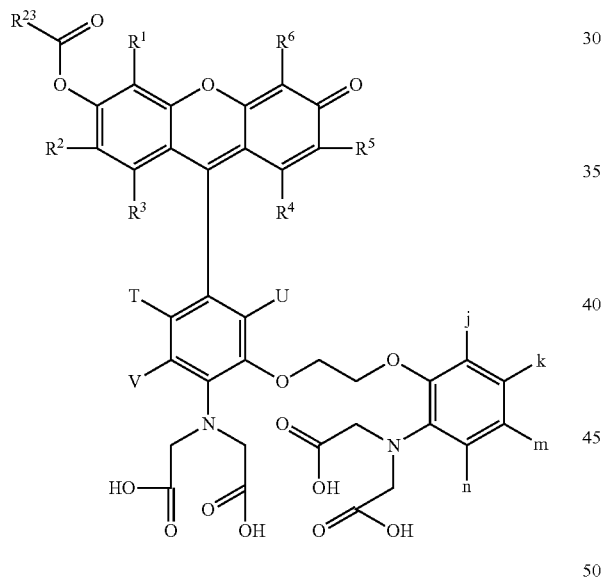

In this embodiment, substituents T and U are independently selected from H, alkyl having 1-12 carbons, alkoxy having 1-12 carbons, aryloxy, amino, halogen, cyano, carboxy, carboxyalkyl, carbonyl, sulfonyl, phosphonyl, boronic acid, aryl and heteroaryl. $R^1$-$R^6$, j, k, m, n and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. $R^{23}$ is H or an alkyl having 1-12 carbons or carboxyalkyl, alkoxy, aryloxy, amino, alkylamino or arylamino. In this embodiment, $R^{23}$ is typically lower alkyl or lower alkoxy having 1-12 carbon atoms. Preferably $R^{23}$ is methyl or methoxy. More preferably $R^{23}$ is methyl.

In yet another aspect of the invention, the compounds of the invention are fluorescent indicators which can be described by Formula 27, below.

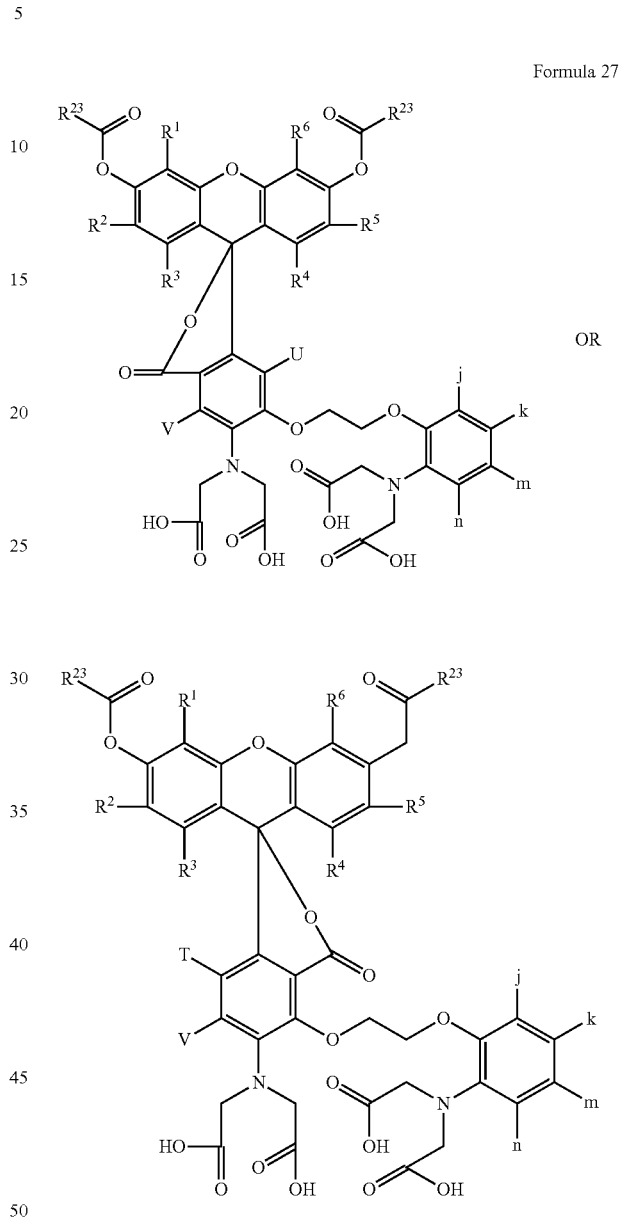

Formula 27

OR

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. $R^{23}$ is independently H or an alkyl having 1-12 carbons or carboxyalkyl, alkoxy, aryloxy, amino, alkylamino or arylamino. In this embodiment, $R^{23}$ is typically lower alkyl or lower alkoxy having 1-12 carbon atoms. Preferably $R^{23}$ is methyl or methoxy. More preferably $R^{23}$ is methyl.

In yet another aspect of the invention, the compounds of the invention are fluorescent indicators which can be described by Formula 28, below.

Formula 28

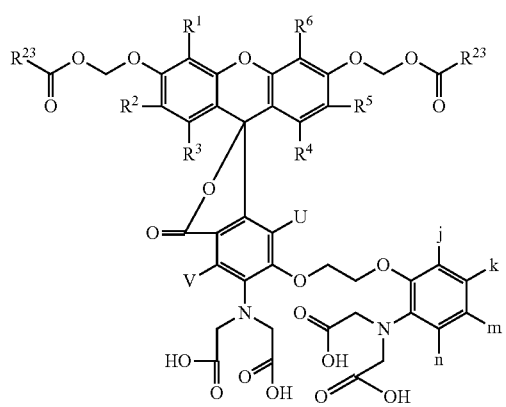

OR

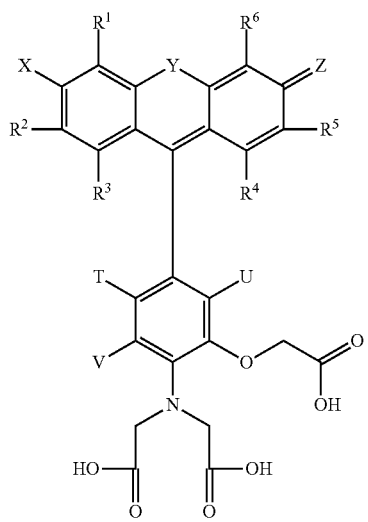

Formula 29

In this embodiment, substituents $R^1$-$R^6$, j, k, m, n, T, U and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. $R^{23}$ is independently H or alkyl having 1-12 carbons or carboxyalkyl, alkoxy, aryloxy, amino, alkylamino or arylamino. In this embodiment, $R^{23}$ is typically lower alkyl or lower alkoxy of 1-12 carbon atoms. Preferably $R^{23}$ is methyl or methoxy. More preferably $R^{23}$ is methyl.

In yet another aspect of the invention, the compound of the invention can be described by Formula 29, below.

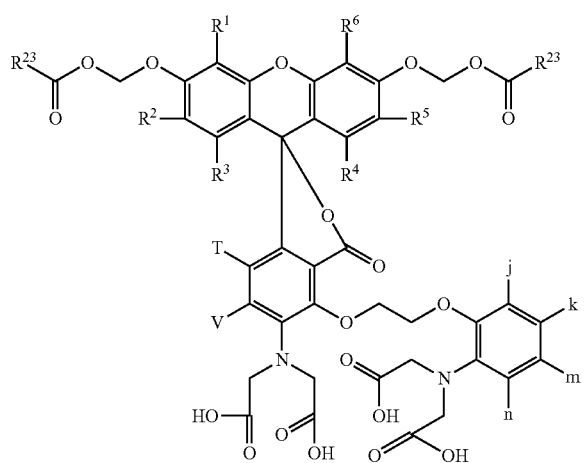

In this embodiment, Y is independently selected from O, S, Se, $NR^9$ and $CR^{10}R^{11}$; X and Z are independently selected from O and $NR^{12}R^{13}$, where each $R^9$, $R^{10}$, $R^{11}$, $R^{12}$ and $R^{13}$ is independently H or alkyl having 1-12 carbons or carboxyalkyl. T and U are independently selected from alkyl having 1-12 carbons, alkoxy having 1-12 carbons, aryloxy, amino, halogen, cyano, carboxy, carboxyalkyl, carbonyl, sulfonyl, phosphonyl, boronic acid, aryl and heteroaryl. $R^1$-$R^6$ and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. In this embodiment, the fluorophore moiety is typically a xanthene.

In yet another aspect of the invention, the compound of the invention can be described by Formula 30, below.

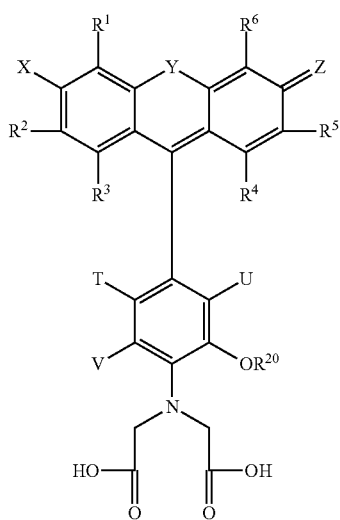

Formula 30

In this embodiment, Y is independently selected from O, S, Se, $NR^9$ and $CR^{10}R^{11}$. X and Z are independently selected from O and $NR^{12}R^{13}$, where each $R^9$, $R^{10}$, $R^{11}$, $R^{12}$ and $R^{13}$ is independently H or alkyl having 1-12 carbons or carboxyalkyl. T and U are independently selected from an alkyl having 1-12 carbons, alkoxy having 1-12 carbons, aryloxy, amino, halogen, cyano, carboxy, carboxyalkyl, carbonyl, sulfonyl, phosphonyl, boronic acid, aryl and heteroaryl. $R^1$-$R^6$ and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. In this embodiment, preferably the fluorophore moiety is a xanthene. $R^{20}$ is typically alky or aryl.

In yet another aspect of the invention, the compound of the invention can be described by Formula 31, below.

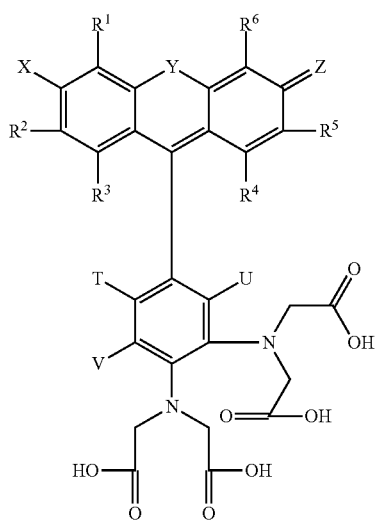

Formula 31

In this embodiment, Y is independently selected from O, S, Se, $NR^9$ and $CR^{10}R^{11}$, X and Z are independently selected from O and $NR^{12}R^{13}$, where each $R^9$, $R^{10}$, $R^{11}$, $R^{12}$ and $R^{13}$ are independently H or an alkyl having 1-12 carbons or carboxyalkyl. T and U are independently selected from an alkyl having 1-12 carbons, alkoxy having 1-12 carbons, aryloxy, amino, halogen, cyano, carboxy, carboxyalkyl, carbonyl, sulfonyl, phosphonyl, boronic acid, aryl or heteroaryl. $R^1$-$R^6$ and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, alkoxy that is itself optionally substituted one or more times by halogen, amino, hydroxy, phosphonyl, sulfonyl, carbonyl, boronic acid, aryl or heteroaryl. In this embodiment, preferably the fluorophore moiety is a xanthene.

In yet another aspect of the invention, the compound of the invention can be described by Formula 32, below.

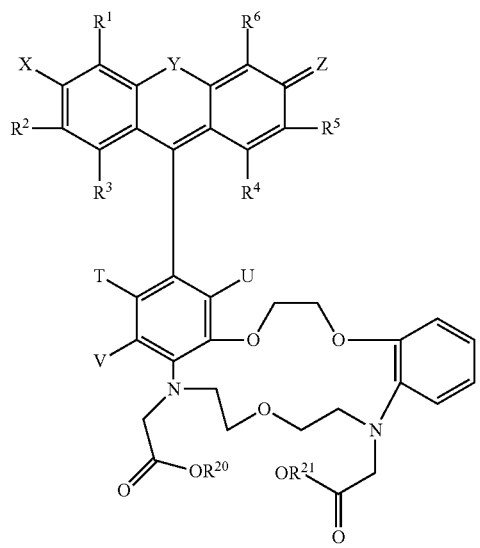

Formula 32

In this embodiment, Y is independently selected from O, S, Se, $NR^9$ and $CR^{10}R^{11}$. X and Z are independently selected from O and $NR^{12}R^{13}$, where each $R^9$, $R^{10}$, $R^{11}$, $R^{12}$ and $R^{13}$ are independently H, alkyl having 1-12 carbons, or carboxyalkyl. T and U are independently selected from an alkyl having 1-12 carbons, alkoxy having 1-12 carbons, aryloxy, amino, halogen, cyano, carboxy, carboxyalkyl, carbonyl, sulfonyl, phosphonyl, boronic acid, aryl, and heteroaryl. $R^1$-$R^6$ and V are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl, or heteroaryl. $R^{20}$ and $R^{21}$ are independently H or alkyl having 1-12 carbons, or carboxyalkyl. Typically the fluorophore moiety is a xanthene.

In yet another aspect of the invention, the compounds of the invention further include the alkyl ester derivatives of any of the compounds described by Formulas 2 to 32, in order to facilitate the delivery of fluorescent metal ion indicators into live cells. The acetoxymethyl (AM) esters of the disclosed fluorescent indicators are preferably used for applications that include the detection of ions in live cells.

The AM esters of the invention can be described by Formula 33, below.

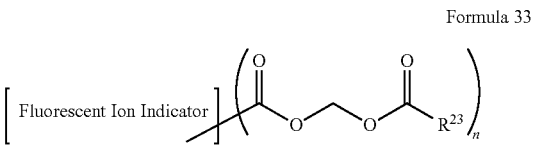

Formula 33

In the above formula, the "Fluorescent Ion Indicator" moiety corresponds to a compound of Formula 2 to 32, n is an integer from 1 to 10, and $R^{23}$ is H or an alkyl having 1-12 carbons or carboxyalkyl, alkoxy, aryloxy, amino, alkylamino or arylamino. In this embodiment, $R^{23}$ is typically lower alkyl or lower alkoxy having 1-12 carbon atoms. Preferably $R^{23}$ is methyl or methoxy. More preferably $R^{23}$ is methyl.

The fluorophore moiety can be any compound described by any of Formulas 2-32 that exhibits an absorption maximum beyond 450 nm, that is bound to a chelator by a covalent linkage L, or that is fused to a chelator. The covalent linkage L may be a single covalent bond, or a suitable combination of stable chemical bonds, as described in greater detail below. The covalent linkage binding the fluorophore moiety to the chelator is typically a single bond, but optionally incorporates 1-20 nonhydrogen atoms selected from the group consisting of C, N, O, P, and S.

As described above, where the fluorophore moiety is a xanthene, the resulting compound may be a fluorescein, a rhodol (U.S. Pat. No. 5,227,487, hereby incorporated by reference), or a rhodamine. As used herein, fluorescein includes benzo- or dibenzofluoresceins, seminaphthofluoresceins, or naphthofluoresceins. Similarly, as used herein rhodol includes seminaphthorhodafluors (U.S. Pat. No. 4,945,171, hereby incorporated by reference). Fluorinated xanthene dyes have been described previously as possessing particularly useful fluorescence properties (U.S. Pat. No. 6,162,931, hereby incorporated by reference).

Alternatively, the fluorophore moiety is a xanthene that is bound via a covalent linkage L that is a single covalent bond at the 9-position of the xanthene. Preferred xanthenes include derivatives of 3H-xanthen-6-ol-3-one bound at the 9-position, derivatives of 6-amino-3H-xanthen-3-one bound at the 9-position, or derivatives of 6-amino-3H-xanthen-3-imine bound at the 9-position.

In one aspect of the invention, the fluorophore moiety has an absorption maximum beyond 480 nm. In a particularly useful embodiment, the fluorophore moiety absorbs at or near 488 nm to 514 nm, and so is particularly suitable for excitation by the output of an argon-ion laser excitation source, or near 546 nm, and so is particularly suitable for excitation by a mercury arc lamp.

The fluorophore moiety is typically selected to confer its fluorescence properties on the indicator compound it is incorporated into. That is, the resulting indicator compound exhibits a detectable optical response when excited by energy having a wavelength at which that fluorophore absorbs As used herein, a detectable optical response means a change in, or occurrence of, an optical property that is detectable either by observation or instrumentally, such a change in absorption (excitation) wavelength, fluorescence emission wavelength, fluorescence emission intensity, fluorescence polarization, or fluorescence lifetime, among others.

In addition, the compounds of the invention preferably exhibit a detectable change in the optical response upon binding a target metal ion. Where the detectable response is a fluorescence response, the detectable change is typically a change in fluorescence, such as a change in the intensity, excitation or emission wavelength distribution of fluorescence, fluorescence lifetime, fluorescence polarization, or a combination thereof. Preferably, the change in optical response upon binding the target metal ion is a change in fluorescence intensity that is greater than approximately 50-fold, more preferably greater than 100-fold. In another aspect, the change in optical response upon binding the target metal ion is a shift in the wavelength of maximal excitation or emission. Typically the shift in wavelength is greater than about 20 nm, preferably greater than about 30 nm.

Selected specific compounds of the invention are provided in Table 2.

TABLE 2

Selected embodiment of the compounds of the invention:

| Cpd. no. | Structure | Method of synthesis |
|---|---|---|
| 256 | 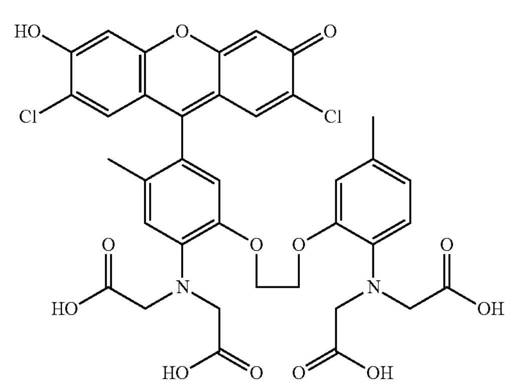 [SMILES: Cc1ccc(N(CC(=O)O)CC(=O)O)c(OCCOc2cc(-c3c4cc(Cl)c(=O)cc-4oc4cc(O)c(Cl)cc34)c(C)cc2N(CC(=O)O)CC(=O)O)c1] | Example 7 |

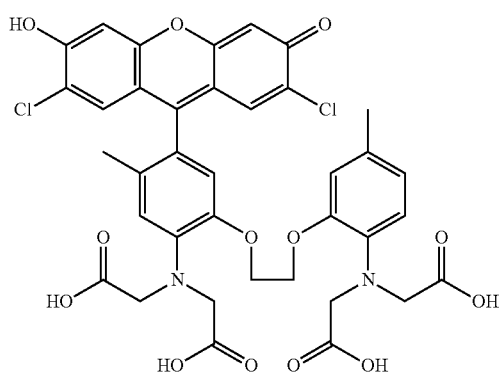

TABLE 2-continued
Selected embodiment of the compounds of the invention:
| Cpd. no. | Structure | Method of synthesis |
|---|---|---|
| 258 | 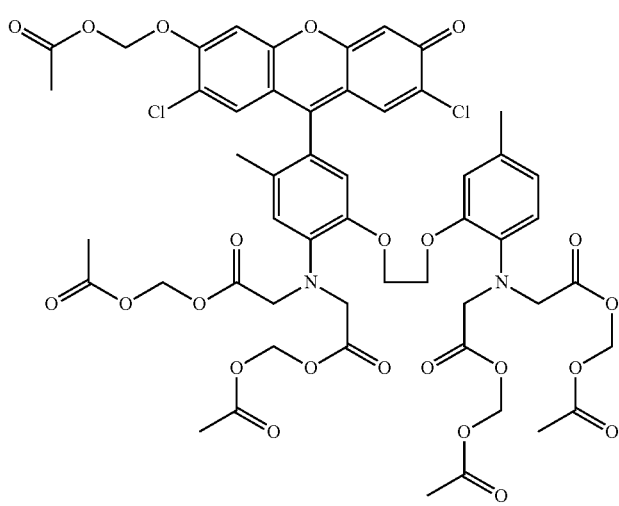 [SMILES: CC(=O)OCOC(=O)CN(CC(=O)OCOC(C)=O)c1ccc(C)cc1OCCOc1cc(-c2c3cc(Cl)c(=O)cc-3oc3cc(OCOC(C)=O)c(Cl)cc23)c(C)cc1N(CC(=O)OCOC(C)=O)CC(=O)OCOC(C)=O] | Example 8 |
| 275 | 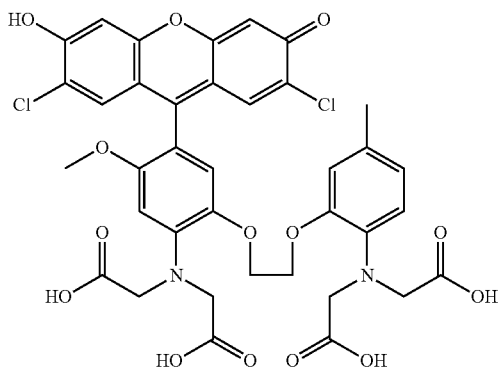 [SMILES: COc1cc(N(CC(=O)O)CC(=O)O)c(OCCOc2cc(C)ccc2N(CC(=O)O)CC(=O)O)cc1-c1c2cc(Cl)c(=O)cc-2oc2cc(O)c(Cl)cc12] | Example 11 |
| 280 | 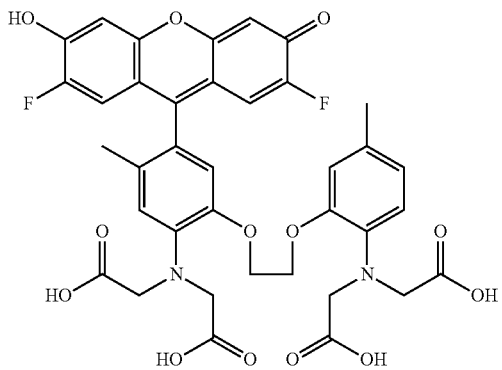 [SMILES: Cc1ccc(N(CC(=O)O)CC(=O)O)c(OCCOc2cc(-c3c4cc(F)c(=O)cc-4oc4cc(O)c(F)cc34)c(C)cc2N(CC(=O)O)CC(=O)O)c1] | Example 12 |

TABLE 2-continued

Selected embodiment of the compounds of the invention:

| Cpd. no. | Structure | Method of synthesis |
|---|---|---|
| 282 | 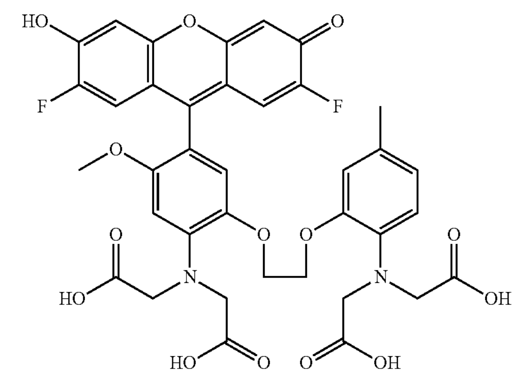 [SMILES: COc1cc(N(CC(=O)O)CC(=O)O)c(OCCOc2cc(C)ccc2N(CC(=O)O)CC(=O)O)cc1-c1c2cc(F)c(=O)cc-2oc2cc(O)c(F)cc12] | Example 13 |
| 284 | 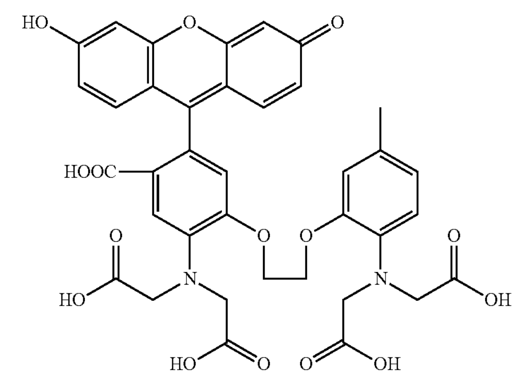 [SMILES: Cc1ccc(N(CC(=O)O)CC(=O)O)c(OCCOc2cc(-c3c4ccc(=O)cc-4oc4cc(O)ccc34)c(C(=O)O)cc2N(CC(=O)O)CC(=O)O)c1] | Example 14 |
| 286 | 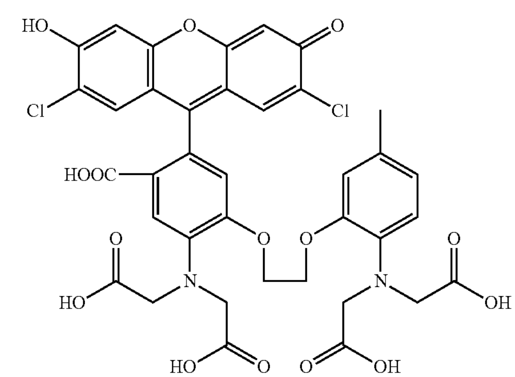 [SMILES: Cc1ccc(N(CC(=O)O)CC(=O)O)c(OCCOc2cc(-c3c4cc(Cl)c(=O)cc-4oc4cc(O)c(Cl)cc34)c(C(=O)O)cc2N(CC(=O)O)CC(=O)O)c1] | Example 15 |
| 288 | 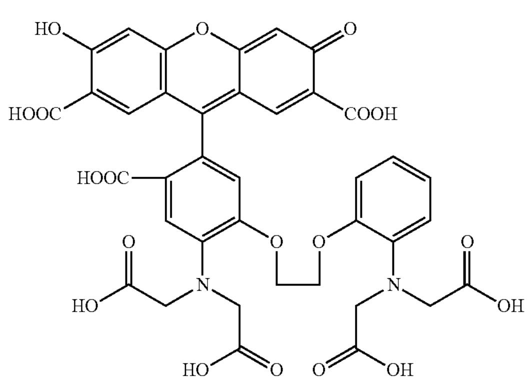 [SMILES: O=C(O)CN(CC(=O)O)c1ccccc1OCCOc1cc(-c2c3cc(C(=O)O)c(=O)cc-3oc3cc(O)c(C(=O)O)cc23)c(C(=O)O)cc1N(CC(=O)O)CC(=O)O] | Example 16 |

TABLE 2-continued
Selected embodiment of the compounds of the invention:
| Cpd. no. | Structure | Method of synthesis |
|---|---|---|
| 290 | 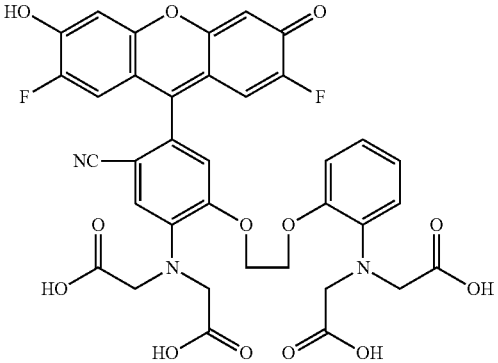 [SMILES: N#Cc1cc(N(CC(=O)O)CC(=O)O)c(OCCOc2ccccc2N(CC(=O)O)CC(=O)O)cc1-c1c2cc(F)c(=O)cc-2oc2cc(O)c(F)cc12] | Example 17 |
| 292 | 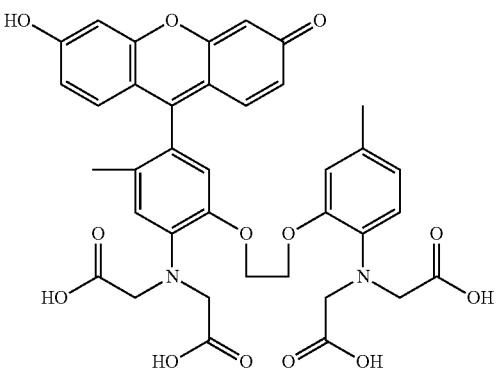 [SMILES: Cc1ccc(N(CC(=O)O)CC(=O)O)c(OCCOc2cc(-c3c4ccc(=O)cc-4oc4cc(O)ccc34)c(C)cc2N(CC(=O)O)CC(=O)O)c1] | Example 18 |
| 294 | 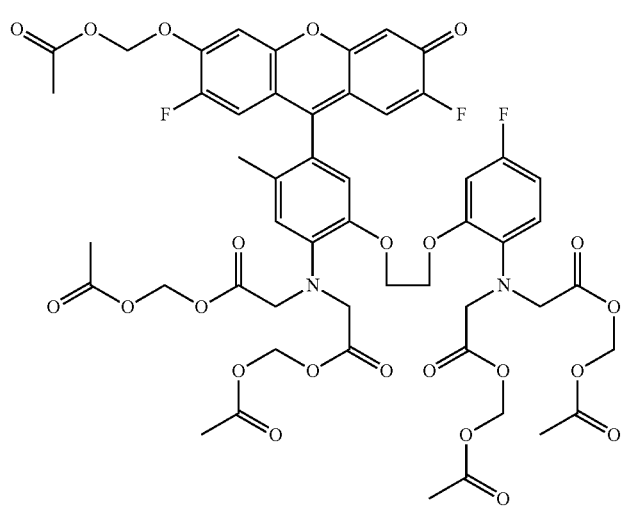 [SMILES: CC(=O)OCOC(=O)CN(CC(=O)OCOC(C)=O)c1ccc(F)cc1OCCOc1cc(-c2c3cc(F)c(=O)cc-3oc3cc(OCOC(C)=O)c(F)cc23)c(C)cc1N(CC(=O)OCOC(C)=O)CC(=O)OCOC(C)=O] | Example 19 |

TABLE 2-continued
Selected embodiment of the compounds of the invention:
| Cpd. no. | Structure | Method of synthesis |
|---|---|---|
| 296 | 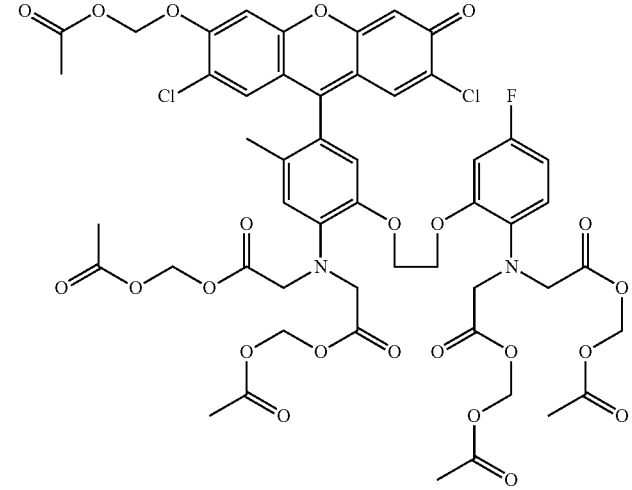 [SMILES: CC(=O)OCOC(=O)CN(CC(=O)OCOC(C)=O)c1ccc(F)cc1OCCOc1cc(-c2c3cc(Cl)c(=O)cc-3oc3cc(OCOC(C)=O)c(Cl)cc23)c(C)cc1N(CC(=O)OCOC(C)=O)CC(=O)OCOC(C)=O] | Example 20 |
| 298 | 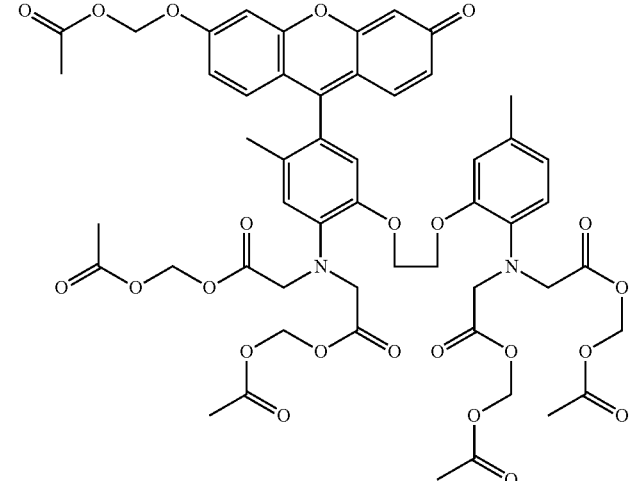 | Example 21 |
| 300 | 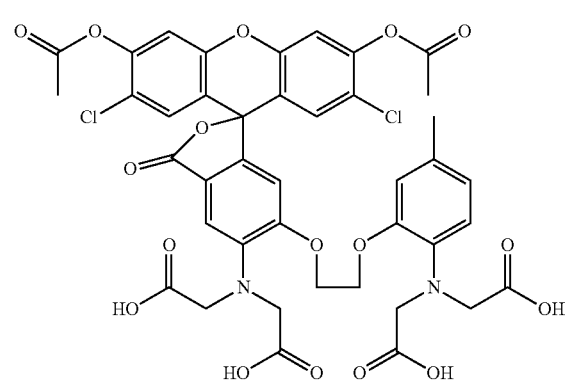 [SMILES: CC(=O)Oc1cc2c(cc1Cl)C1(OC(=O)c3cc(N(CC(=O)O)CC(=O)O)c(OCCOc4cc(C)ccc4N(CC(=O)O)CC(=O)O)cc31)c1cc(Cl)c(OC(C)=O)cc1O2] | Example 22 |

TABLE 2-continued
Selected embodiment of the compounds of the invention:
| Cpd. no. | Structure | Method of synthesis |
|---|---|---|
| 302 | 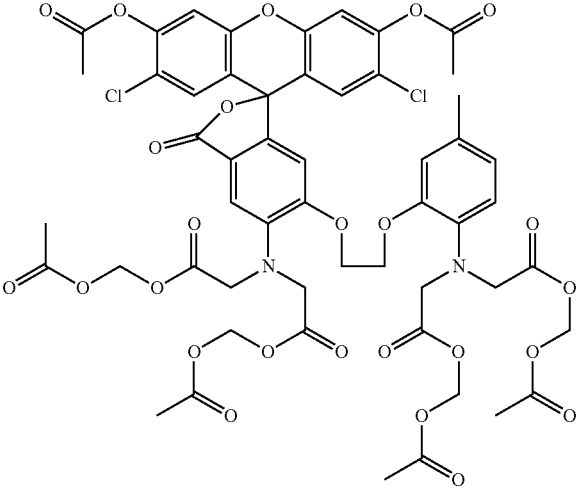 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(Cl)c(OC(C)=O)cc2Oc2cc(OC(C)=O)c(Cl)cc21] | Example 23 |
| 304 | 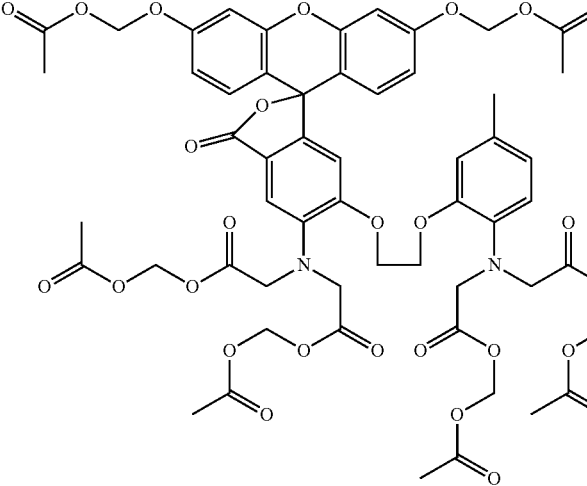 | Example 24 |
| 306 | 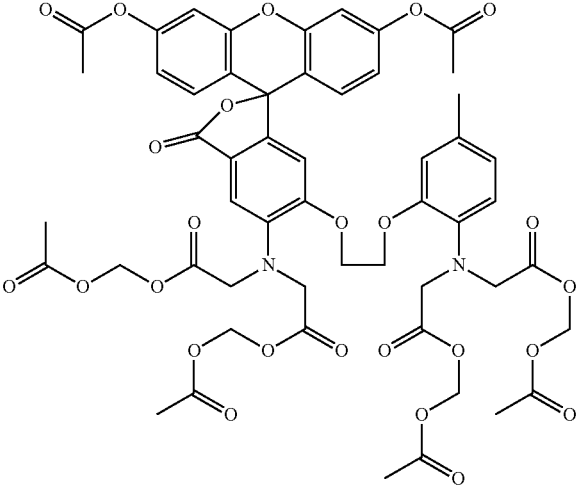 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2ccc(OC(C)=O)cc2Oc2cc(OC(C)=O)ccc21] | Example 25 |

Figure 8:
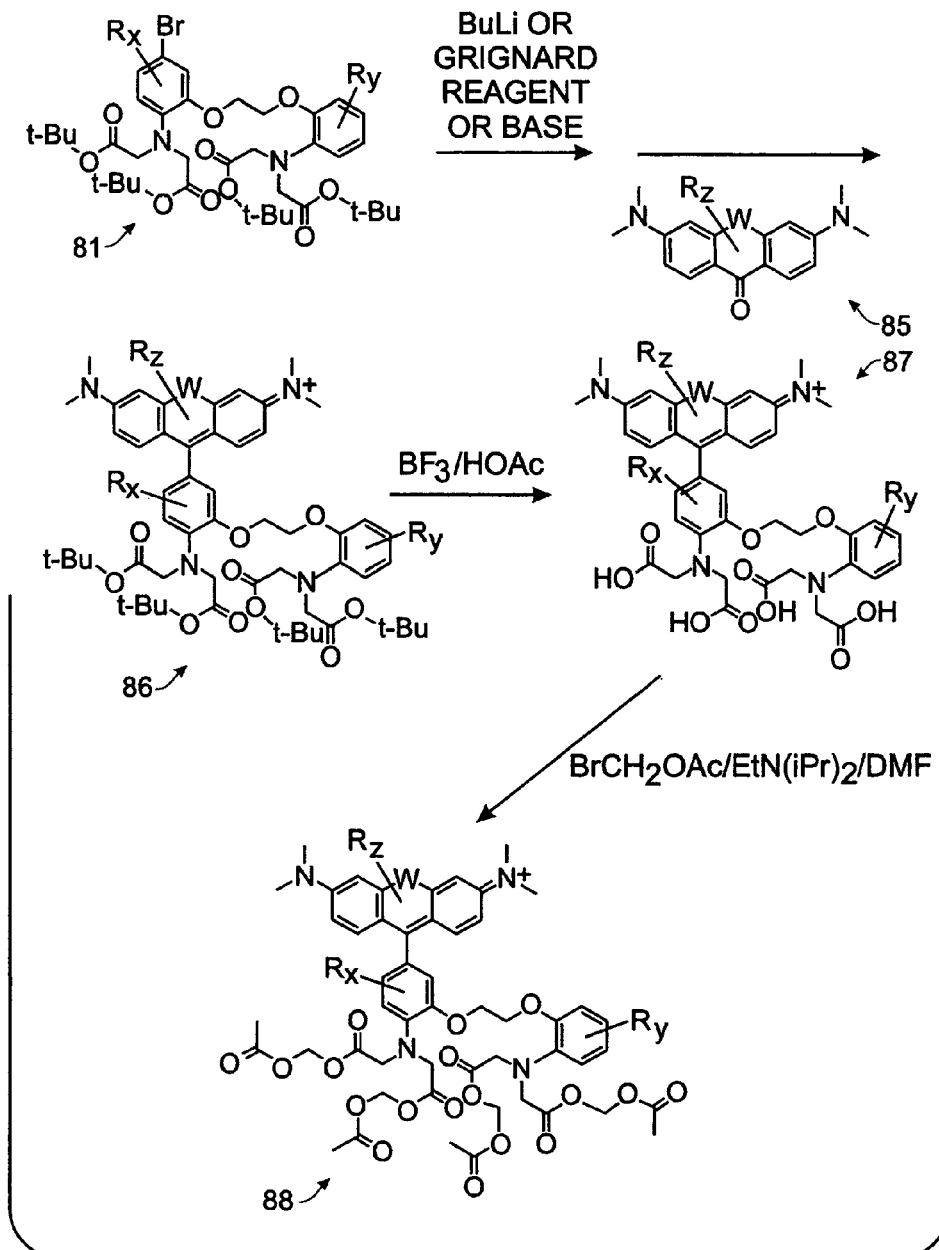
FIG. 8. A synthetic scheme for the preparation of selected rhodamine-based ion indicators (Method A), where $R_x$, $R_y$ and $R_z$ represent one or more substituents of each ring.

TABLE 2-continued
Selected embodiment of the compounds of the invention:
| Cpd. no. | Structure | Method of synthesis |
|---|---|---|
| 308 | 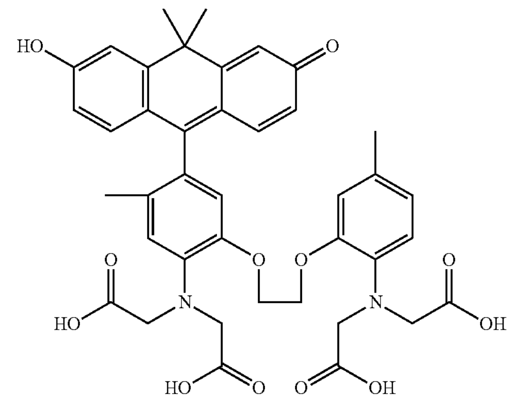 [SMILES: Cc1ccc(N(CC(=O)O)CC(=O)O)c(OCCOc2cc(C3=C4C=CC(=O)C=C4C(C)(C)c4cc(O)ccc43)c(C)cc2N(CC(=O)O)CC(=O)O)c1] | Example 26 |
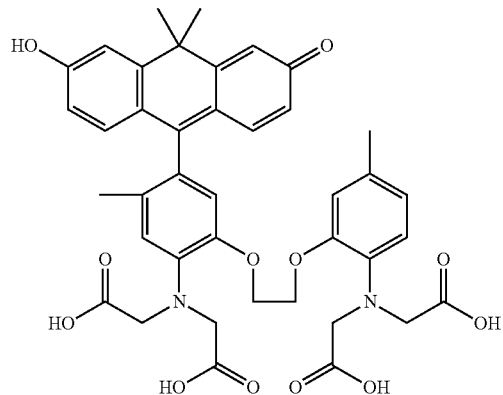
| 310 | | Example 27 |
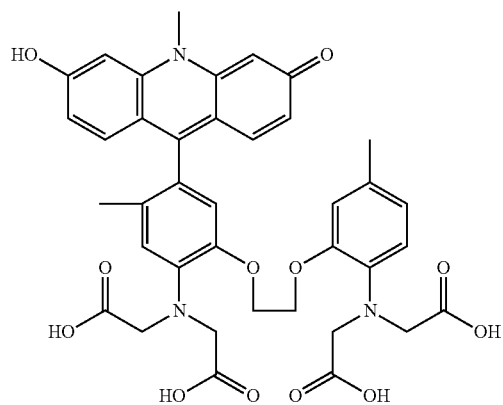 [SMILES: Cc1ccc(N(CC(=O)O)CC(=O)O)c(OCCOc2cc(-c3c4ccc(=O)cc-4n(C)c4cc(O)ccc34)c(C)cc2N(CC(=O)O)CC(=O)O)c1]
| 350 | | FIG. 8 |
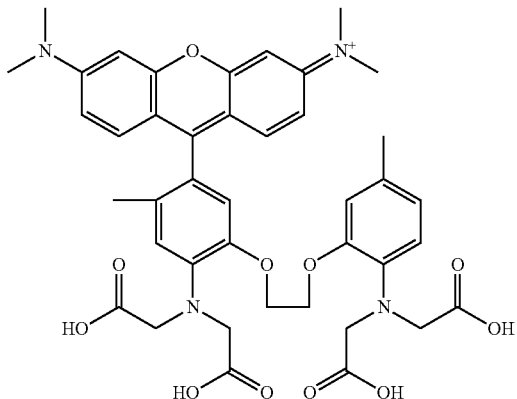 [SMILES: Cc1ccc(N(CC(=O)O)CC(=O)O)c(OCCOc2cc(-c3c4ccc(=[N+](C)C)cc-4oc4cc(N(C)C)ccc34)c(C)cc2N(CC(=O)O)CC(=O)O)c1]

TABLE 2-continued

Figure 6:
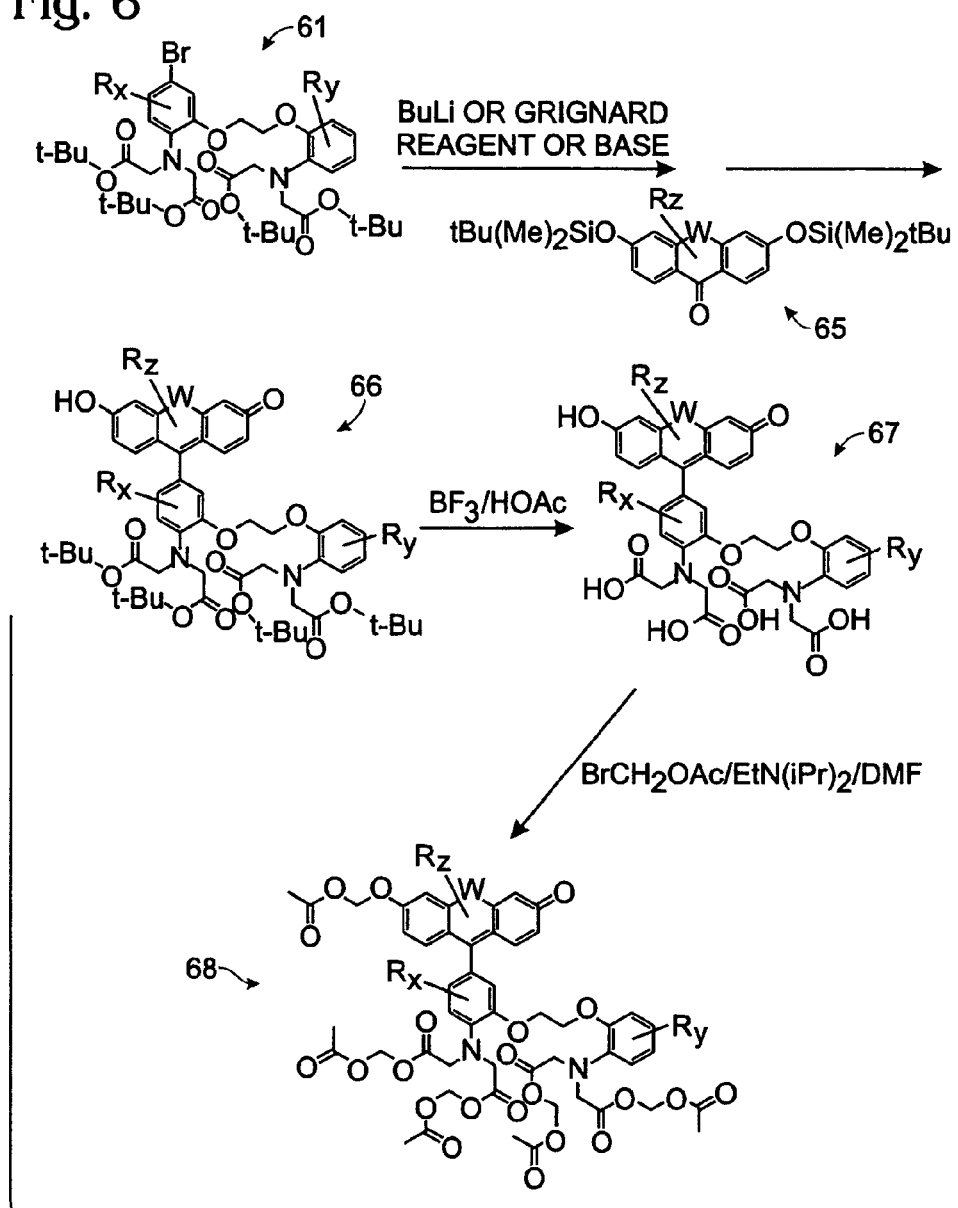
FIG. 6. A synthetic scheme for the preparation of selected fluorescein-based ion indicators (Method A), where $R_x$, $R_y$ and $R_z$ represent one or more substituents of each ring.
Figure 9:
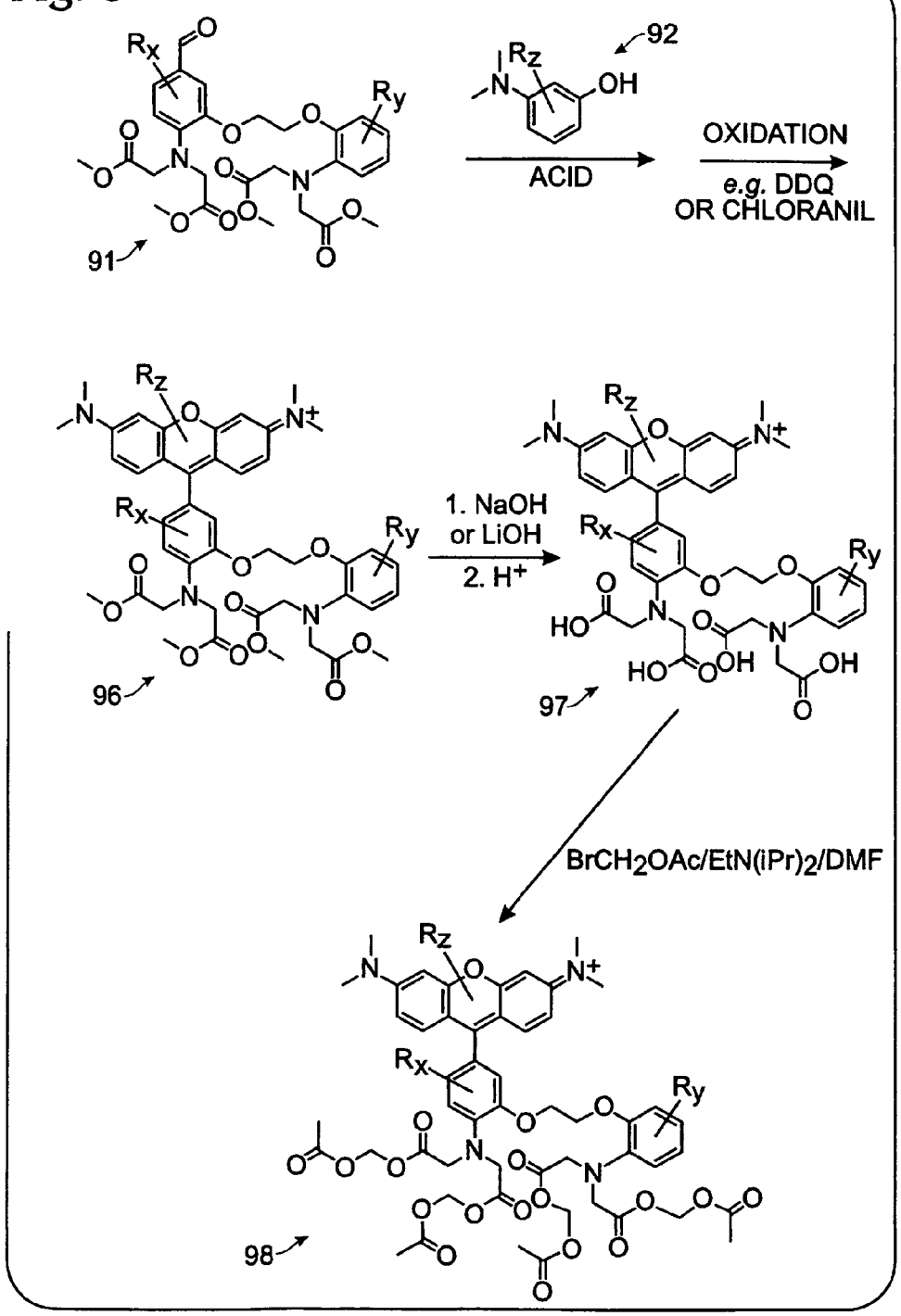
FIG. 9. An alternative synthetic scheme for the preparation of selected rhodamine-based ion indicators (Method B), where $R_x$, $R_y$ and $R_z$ represent one or more substituents of each ring.
Figure 10:
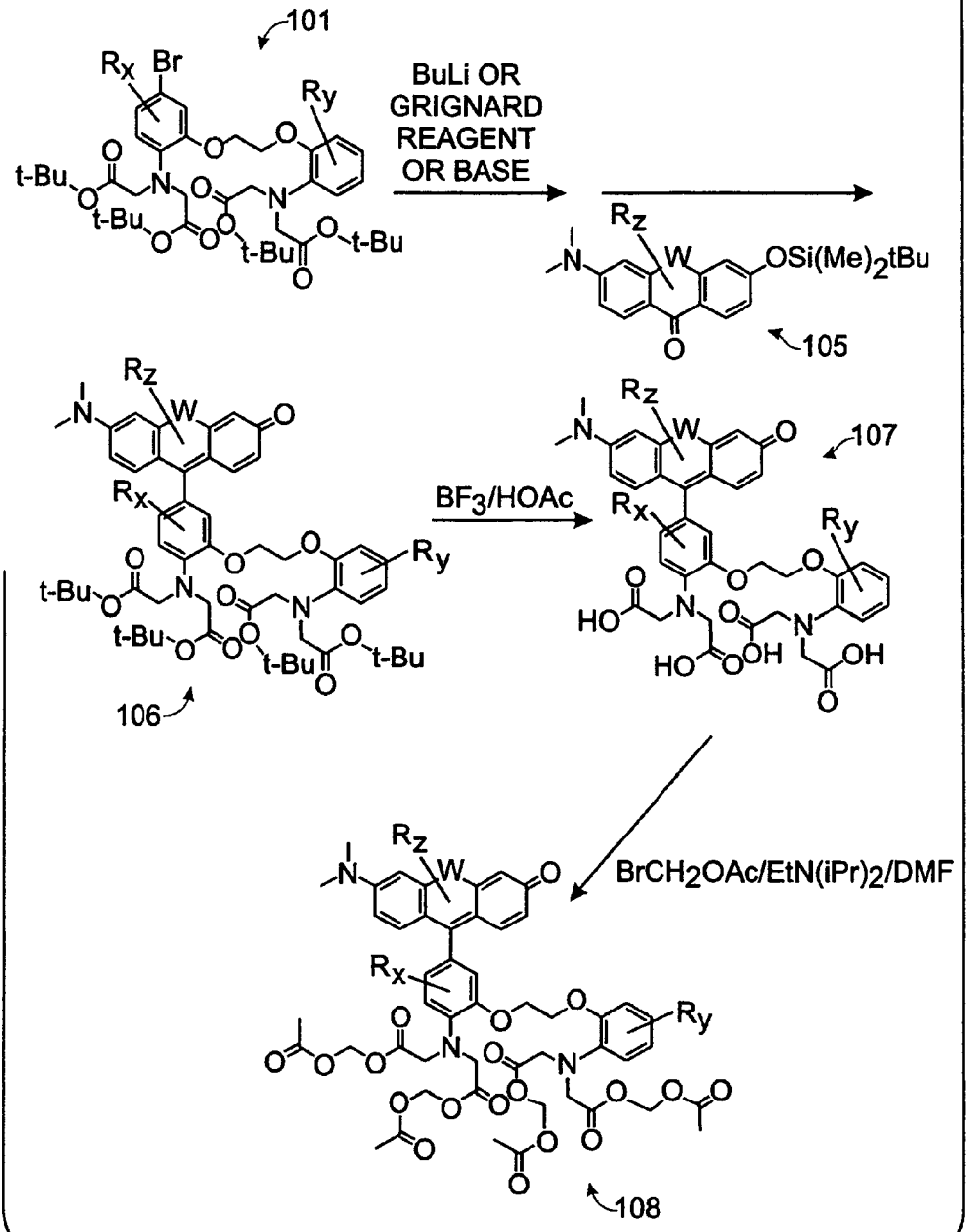
FIG. 10. A synthetic scheme for the preparation of selected rhodol-based ion indicators (Method A), where $R_x$, $R_y$ and $R_z$ represent one or more substituents of each ring.
Figure 11:
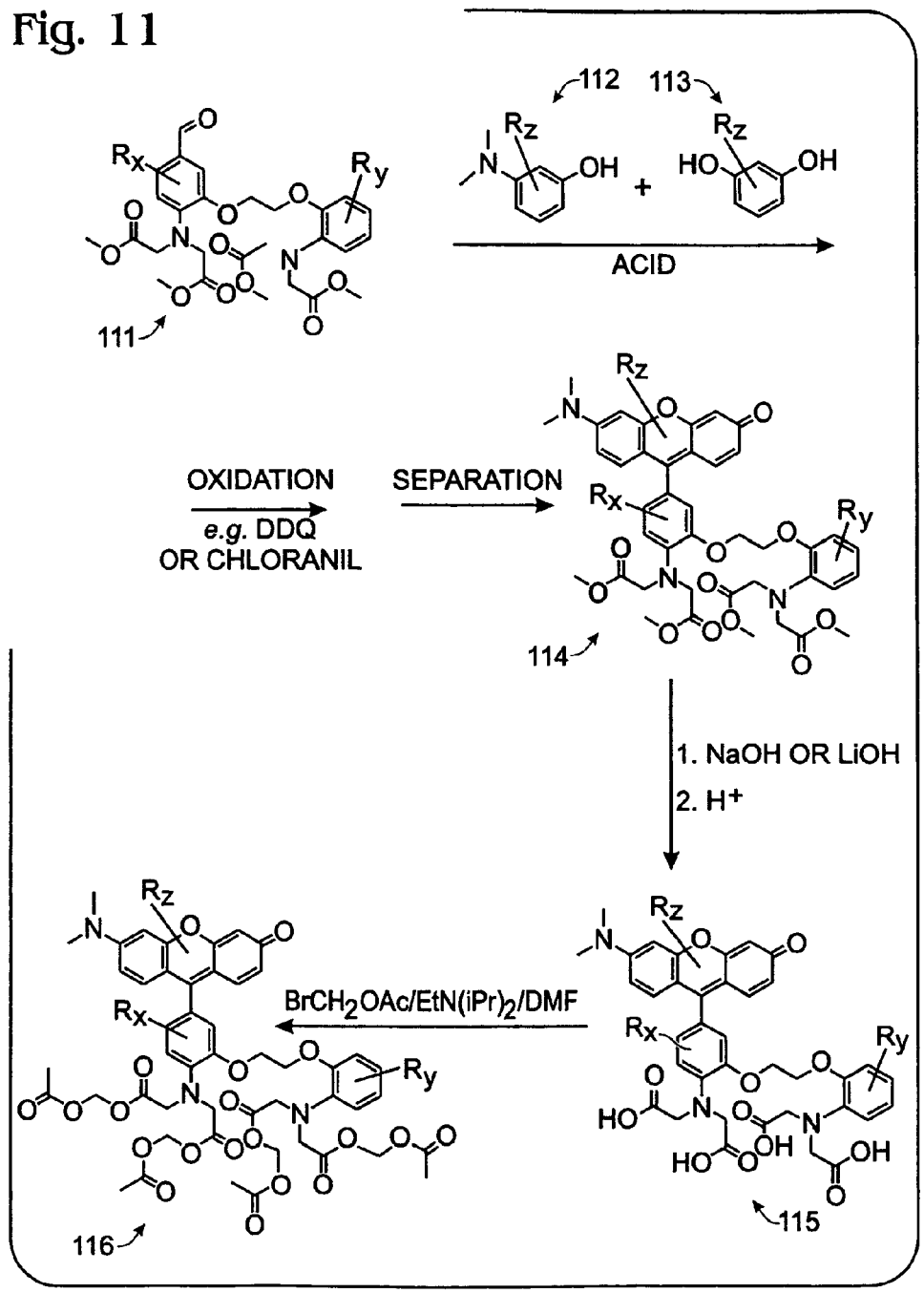
FIG. 11. An alternative synthetic scheme for the preparation of selected rhodol-based ion indicators (Method B), where $R_x$, $R_y$ and $R_z$ represent one or more substituents of each ring.
Figure 12:
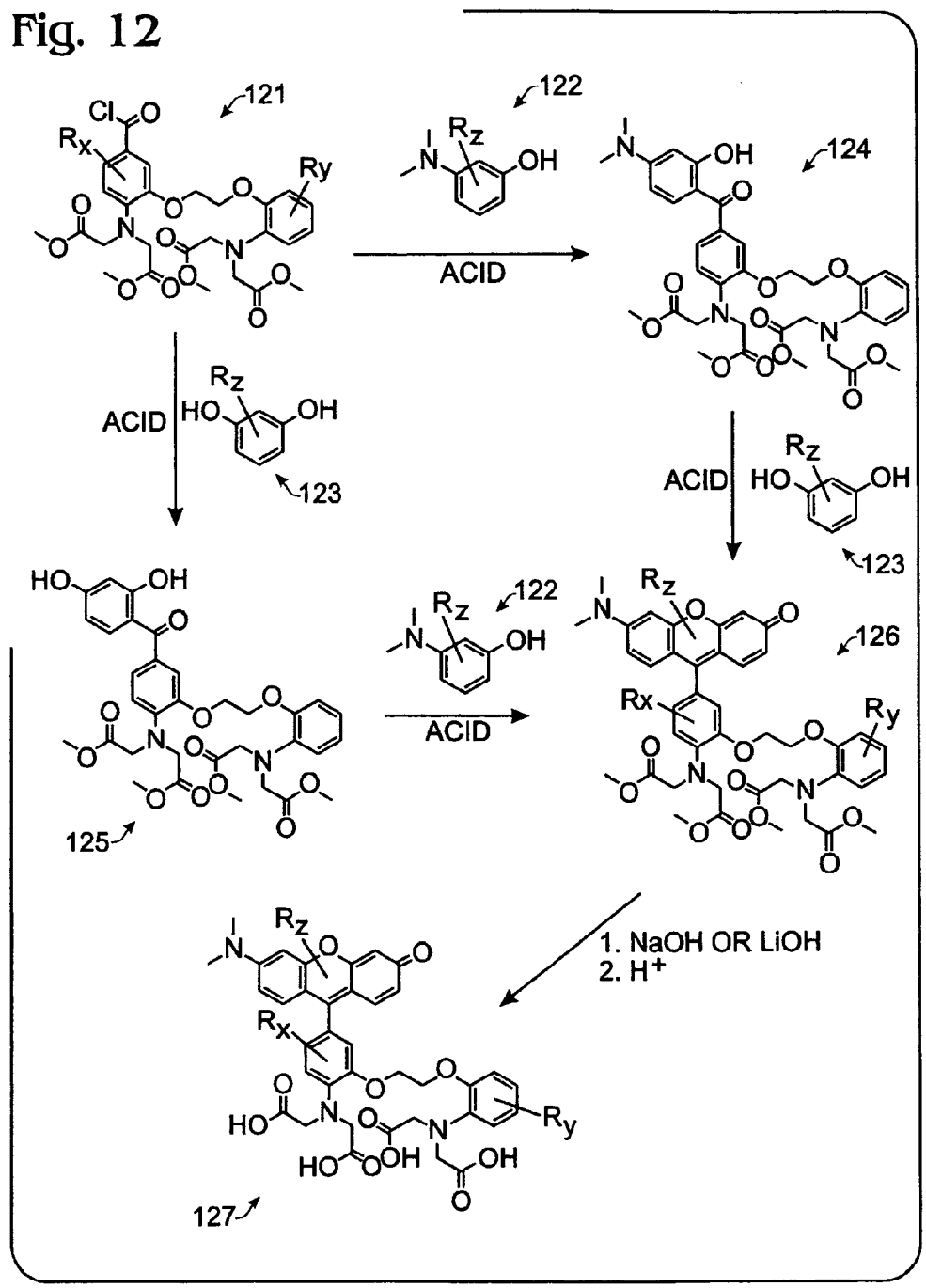
FIG. 12. Another alternative synthetic scheme for the preparation of selected rhodol-based ion indicators (Method C), where $R_x$, $R_y$ and $R_z$ represent one or more substituents of each ring.

Selected embodiment of the compounds of the invention:

| Cpd. no. | Structure | Method of synthesis |
|---|---|---|
| 351 | 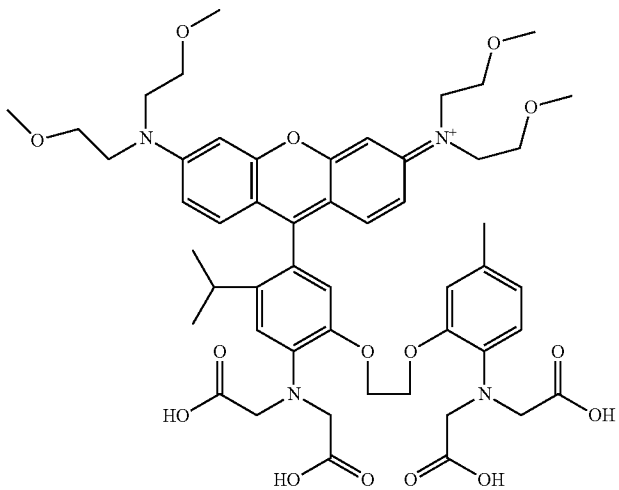 [SMILES: COCCN(CCOC)c1ccc2c(-c3cc(OCCOc4cc(C)ccc4N(CC(=O)O)CC(=O)O)c(N(CC(=O)O)CC(=O)O)cc3C(C)C)c3ccc(=[N+](CCOC)CCOC)cc-3oc2c1] | FIG. 8 or FIG. 9 |
| 352 | 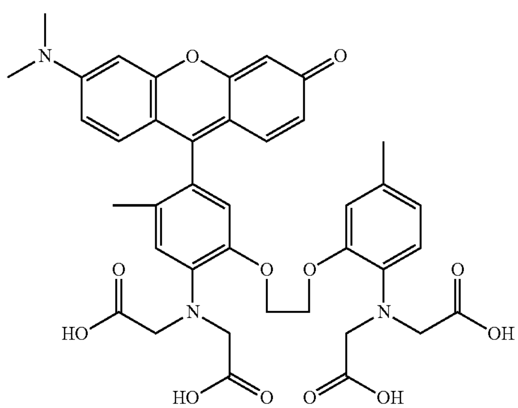 [SMILES: Cc1ccc(N(CC(=O)O)CC(=O)O)c(OCCOc2cc(-c3c4ccc(=O)cc-4oc4cc(N(C)C)ccc34)c(C)cc2N(CC(=O)O)CC(=O)O)c1] | FIG. 10 or FIG. 11 or FIG. 12 |
| 353 | 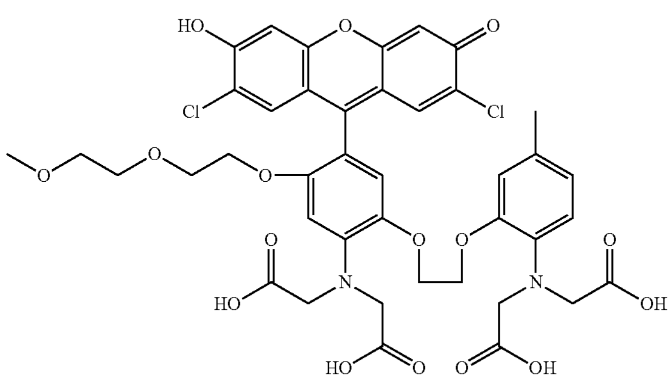 [SMILES: COCCOCCOc1cc(N(CC(=O)O)CC(=O)O)c(OCCOc2cc(C)ccc2N(CC(=O)O)CC(=O)O)cc1-c1c2cc(Cl)c(=O)cc-2oc2cc(O)c(Cl)cc12] | FIG. 6 |

Figure 7:
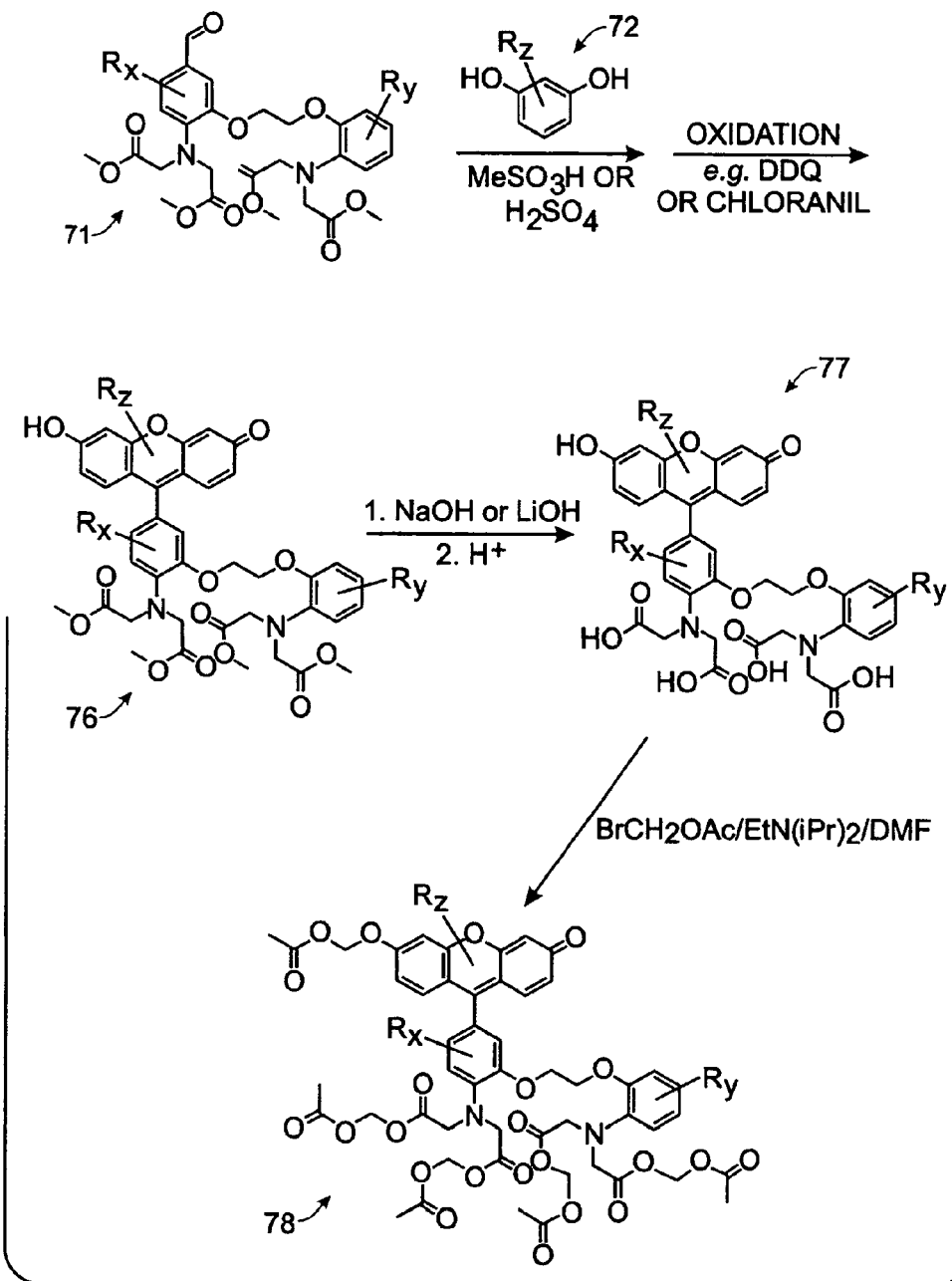
FIG. 7. An alternative synthetic scheme for the preparation of selected fluorescein-based ion indicators (Method B), where $R_x$, $R_y$ and $R_z$ represent one or more substituents of each ring.

TABLE 2-continued
Selected embodiment of the compounds of the invention:
| Cpd. no. | Structure | Method of synthesis |
|---|---|---|
| 352 | 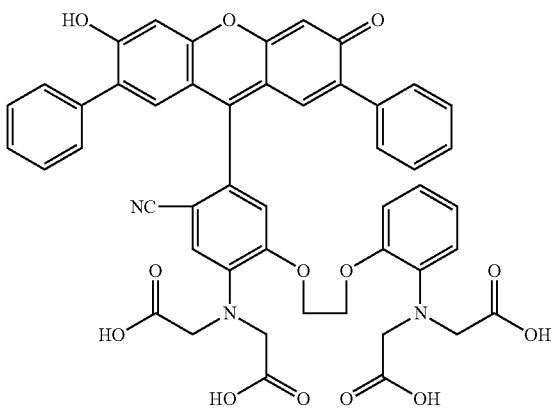 [SMILES: N#Cc1cc(N(CC(=O)O)CC(=O)O)c(OCCOc2ccccc2N(CC(=O)O)CC(=O)O)cc1-c1c2cc(-c3ccccc3)c(=O)cc-2oc2cc(O)c(-c3ccccc3)cc12] | FIG. 7 |
| 353 | 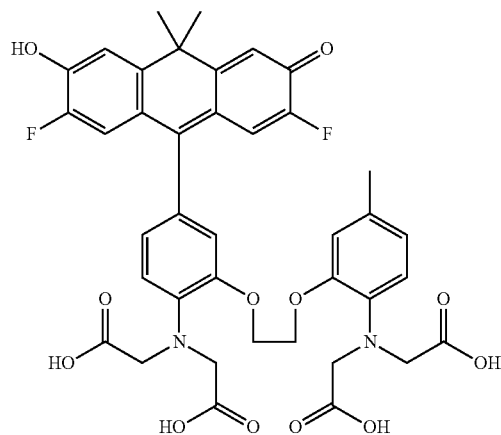 [SMILES: Cc1ccc(N(CC(=O)O)CC(=O)O)c(OCCOc2cc(C3=C4C=C(F)C(=O)C=C4C(C)(C)c4cc(O)c(F)cc43)ccc2N(CC(=O)O)CC(=O)O)c1] | FIG. 6 |
| 354 | 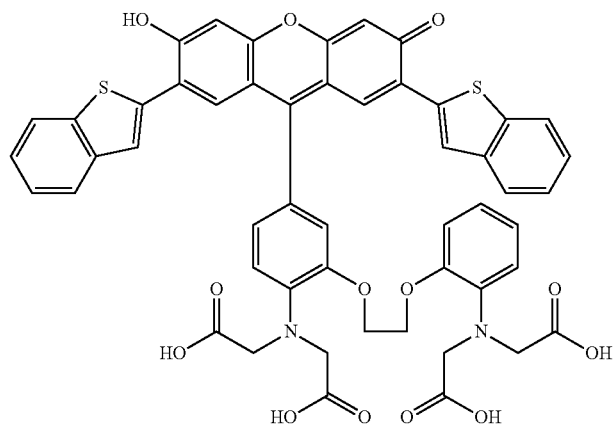 [SMILES: O=C(O)CN(CC(=O)O)c1ccccc1OCCOc1cc(-c2c3cc(-c4cc5ccccc5s4)c(=O)cc-3oc3cc(O)c(-c4cc5ccccc5s4)cc23)ccc1N(CC(=O)O)CC(=O)O] | FIG. 7 |

TABLE 2-continued

Selected embodiment of the compounds of the invention:

| Cpd. no. | Structure | Method of synthesis |
|---|---|---|
| 355 | 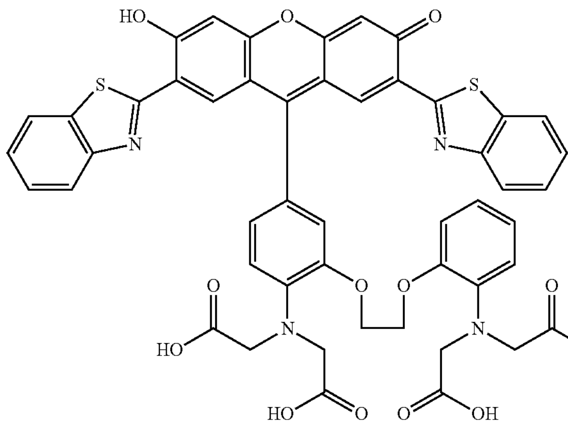 | FIG. 7 |
| 356 | 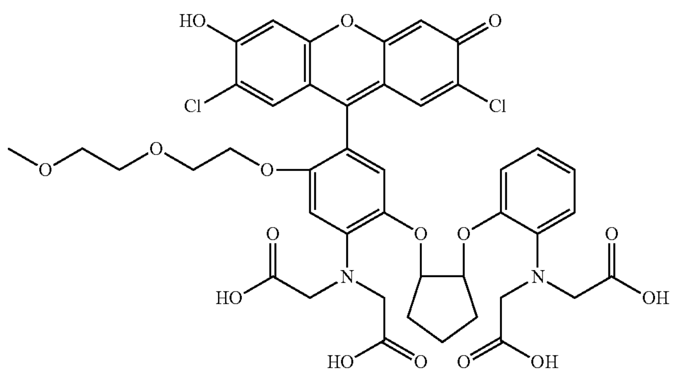 [SMILES: COCCOCCOc1cc(N(CC(=O)O)CC(=O)O)c(OC2CCCC2Oc2ccccc2N(CC(=O)O)CC(=O)O)cc1-c1c2cc(Cl)c(=O)cc-2oc2cc(O)c(Cl)cc12] | FIG. 6 |
| 357 | 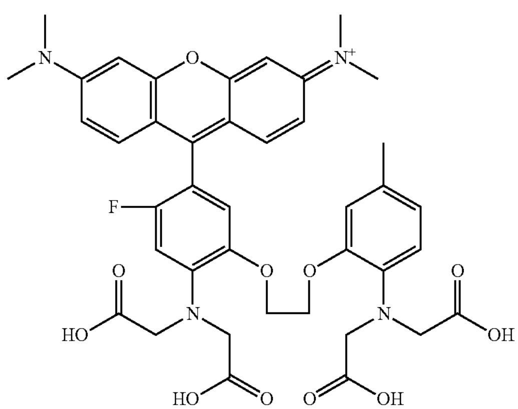 [SMILES: Cc1ccc(N(CC(=O)O)CC(=O)O)c(OCCOc2cc(-c3c4ccc(=[N+](C)C)cc-4oc4cc(N(C)C)ccc34)c(F)cc2N(CC(=O)O)CC(=O)O)c1] | FIG. 9 |
| 358 | 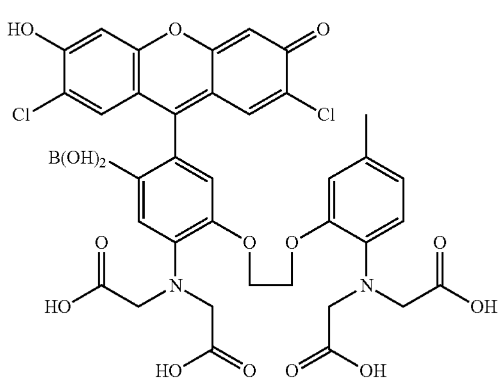 [SMILES: Cc1ccc(N(CC(=O)O)CC(=O)O)c(OCCOc2cc(-c3c4cc(Cl)c(=O)cc-4oc4cc(O)c(Cl)cc34)c(B(O)O)cc2N(CC(=O)O)CC(=O)O)c1] | FIG. 7 |

TABLE 2-continued
Selected embodiment of the compounds of the invention:
| Cpd. no. | Structure | Method of synthesis |
|---|---|---|
| 359 | 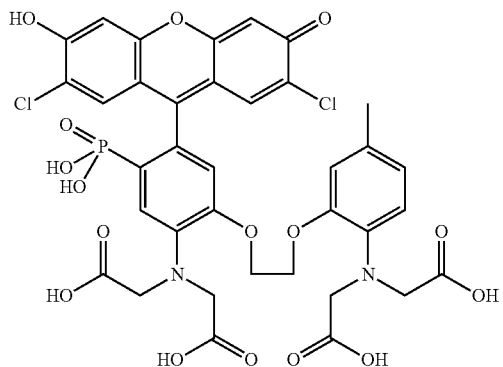 [SMILES: Cc1ccc(N(CC(=O)O)CC(=O)O)c(OCCOc2cc(-c3c4cc(Cl)c(=O)cc-4oc4cc(O)c(Cl)cc34)c(P(=O)(O)O)cc2N(CC(=O)O)CC(=O)O)c1] | FIG. 7 |
| 360 | 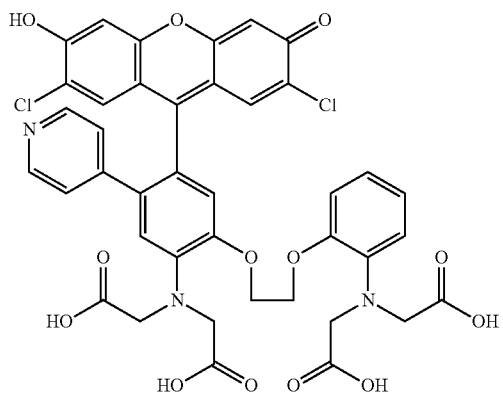 [SMILES: O=C(O)CN(CC(=O)O)c1ccccc1OCCOc1cc(-c2c3cc(Cl)c(=O)cc-3oc3cc(O)c(Cl)cc23)c(-c2ccncc2)cc1N(CC(=O)O)CC(=O)O] | FIG. 6 or FIG. 7 |
| 365 | 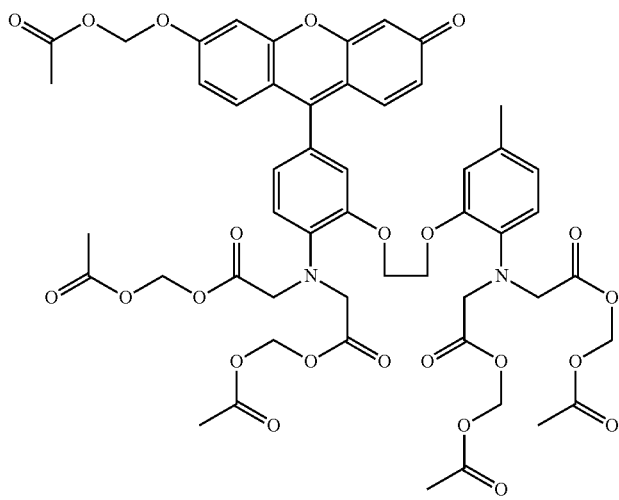 [SMILES: CC(=O)OCOC(=O)CN(CC(=O)OCOC(C)=O)c1ccc(C)cc1OCCOc1cc(-c2c3ccc(=O)cc-3oc3cc(OCOC(C)=O)ccc23)ccc1N(CC(=O)OCOC(C)=O)CC(=O)OCOC(C)=O] | FIG. 6 or FIG. 7 |

TABLE 2-continued

Figure 2:
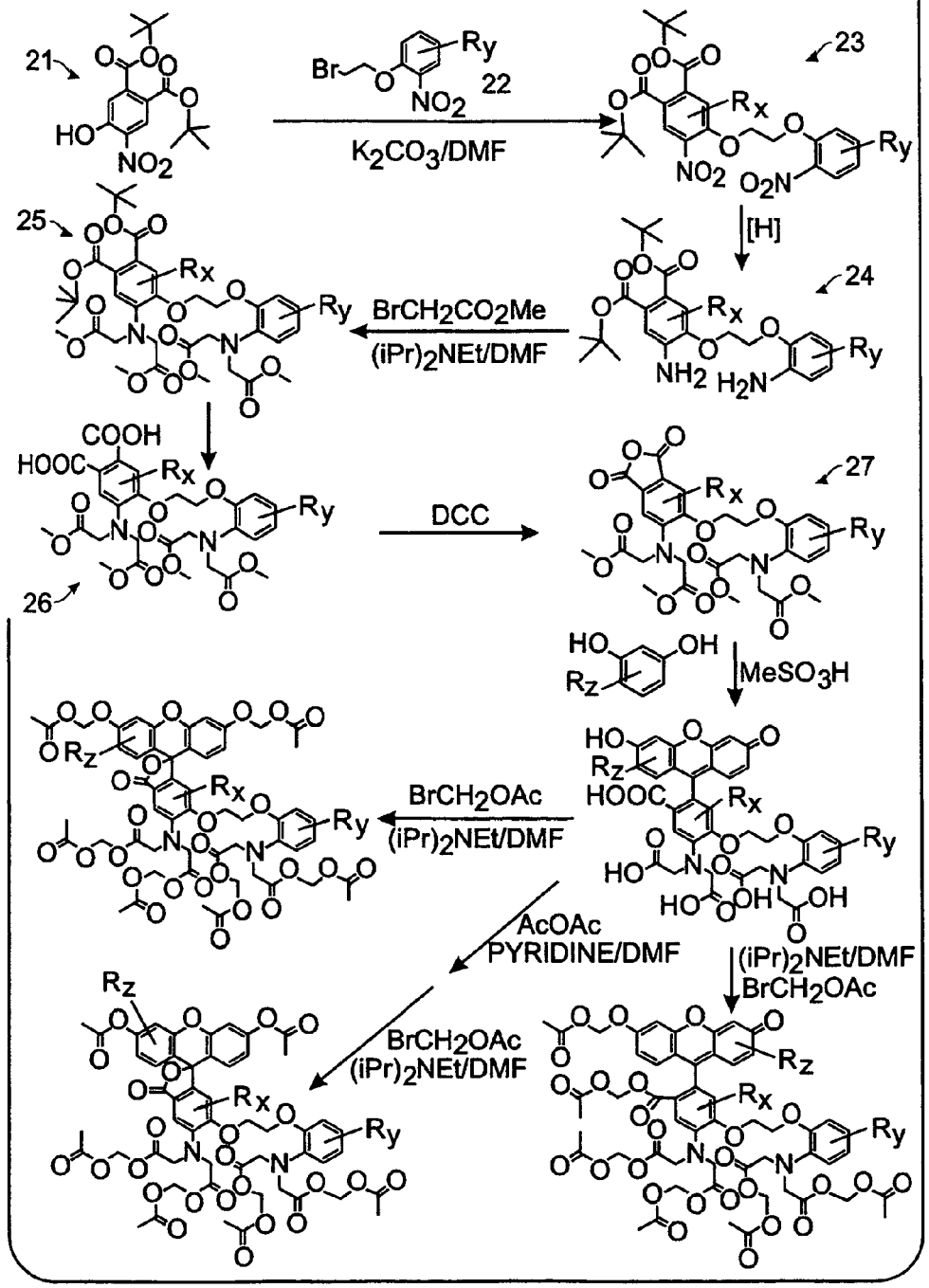
FIG. 2. A synthetic scheme for the preparation of BAPTA anhydride compounds and xanthene-substituted BAPTA compounds, where $R_x$, Ry and Rz represent one or more substituents of each ring.
Figure 3:
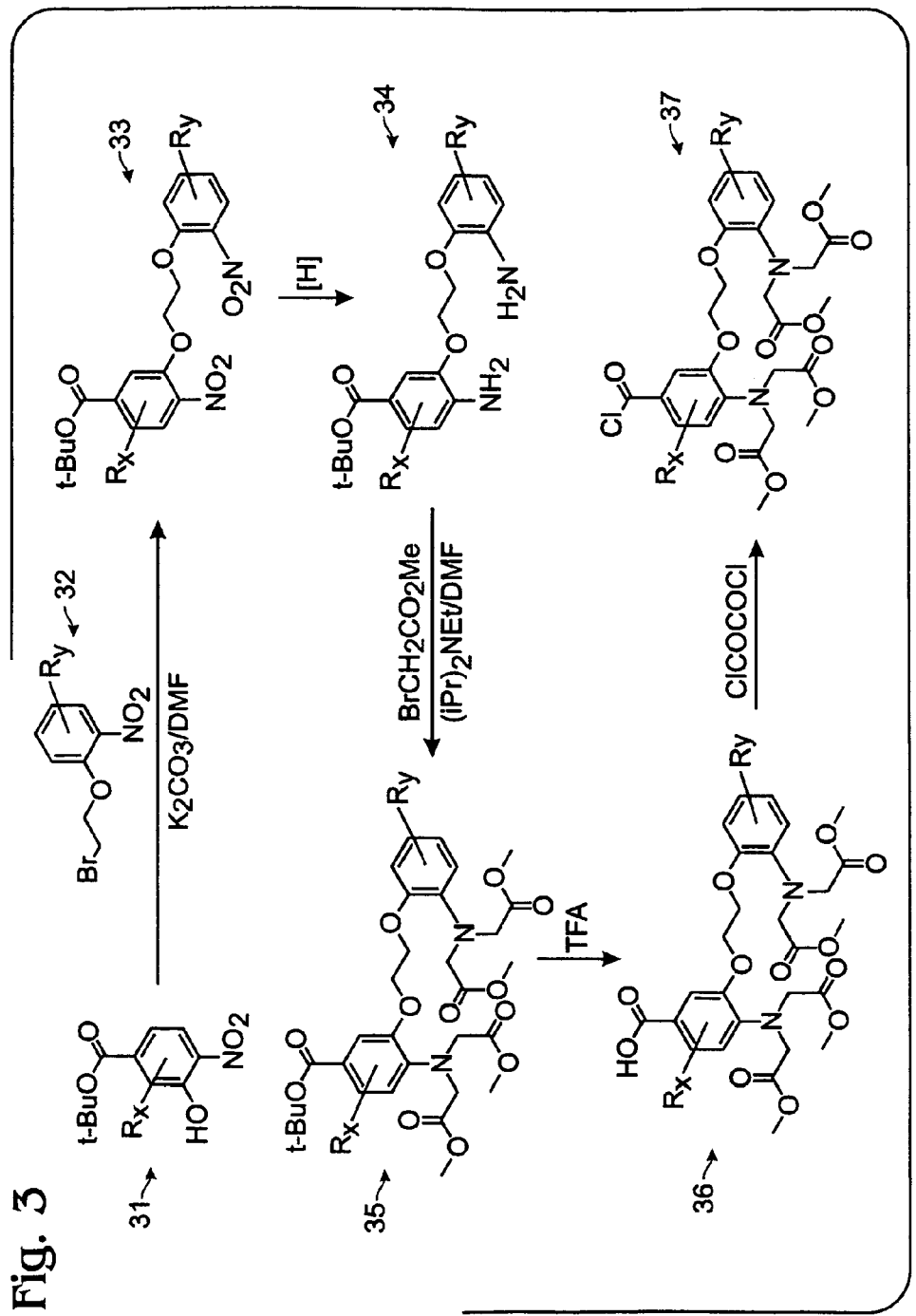
FIG. 3. A synthetic scheme for the preparation of selected BAPTA acid compounds and their derivatives, where $R_x$ and $R_y$ represent one or more substituents of each ring.
Figure 4:
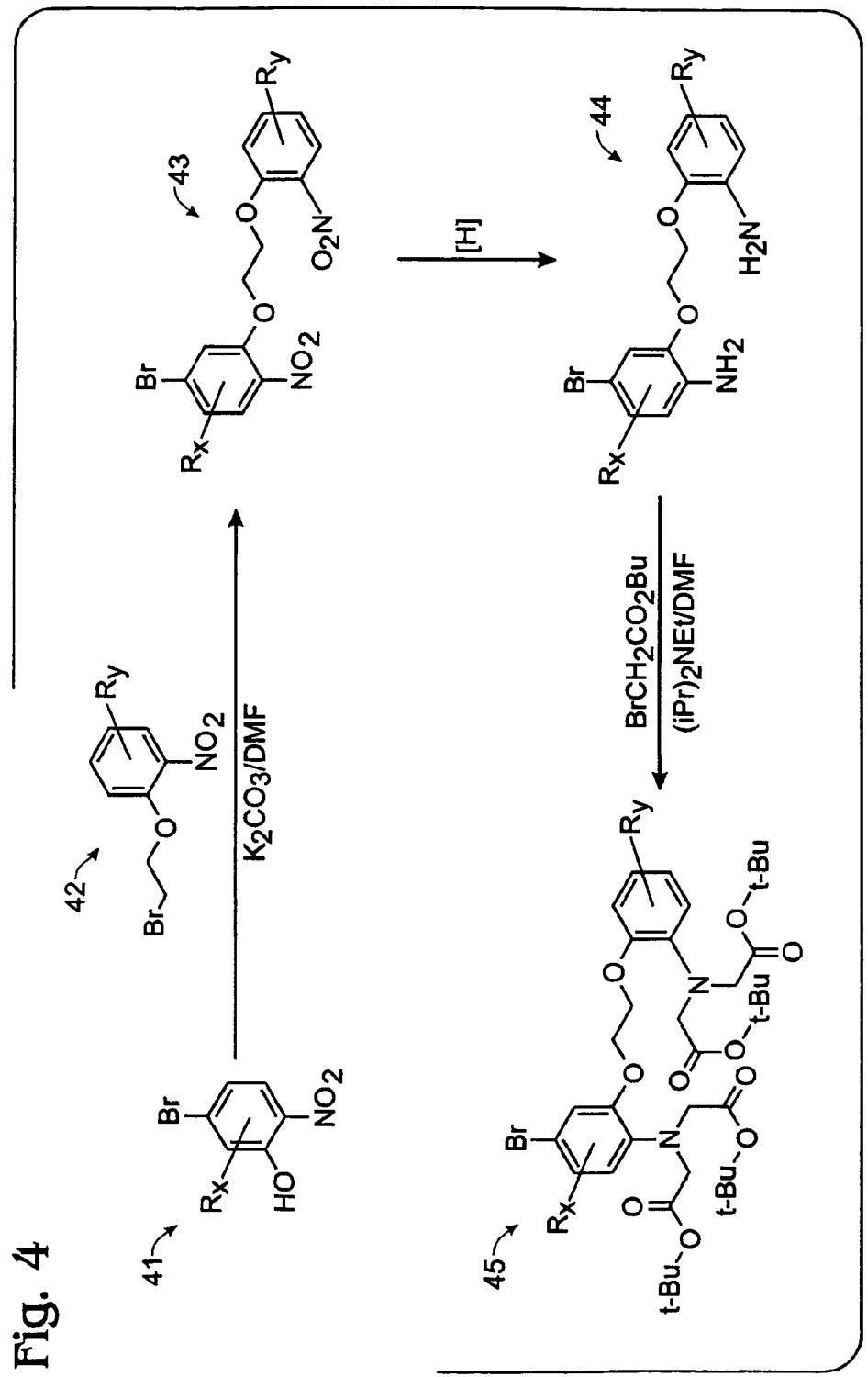
FIG. 4. A synthetic scheme for the preparation of selected BAPTA bromide compounds (Method A), where $R_x$ and $R_y$ represent one or more substituents of each ring.
Figure 5:
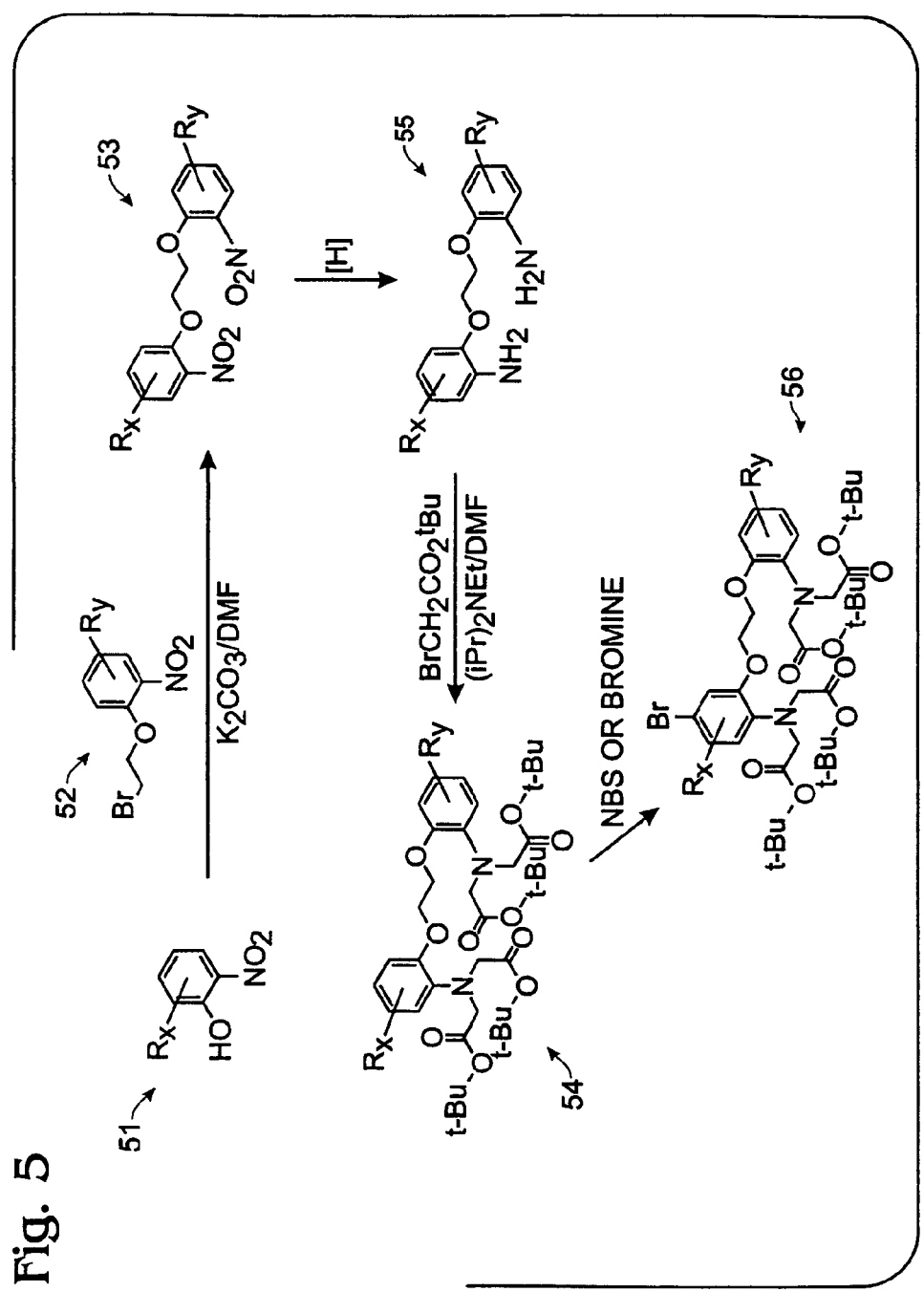
FIG. 5. An alternative synthetic scheme for the preparation of BAPTA bromide compounds (Method B), where. $R_x$ and $R_y$ represent one or more substituents of each ring.

Selected embodiment of the compounds of the invention:

| Cpd. no. | Structure | Method of synthesis |
|---|---|---|
| 366 | 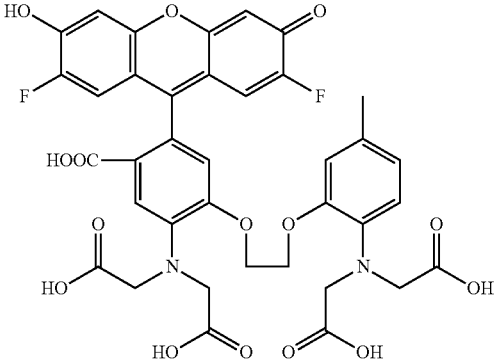 [SMILES: Cc1ccc(N(CC(=O)O)CC(=O)O)c(OCCOc2cc(-c3c4cc(F)c(=O)cc-4oc4cc(O)c(F)cc34)c(C(=O)O)cc2N(CC(=O)O)CC(=O)O)c1] | FIG. 2 |

Synthesis

The compounds of the invention may be prepared using any suitable synthetic scheme. The methodology used to prepare the compounds of the invention may involve two components. The first component may involve the formation of the chelator, while the second may involve the modification of the chelator by forming a reactive functional group, covalently attaching a conjugate, or covalently attaching a fluorophore moiety to form the desired indicator compound. Although these synthetic components are typically performed in the order given, they may be carried out in any other suitable sequence. For example, a portion of the chelator may be derivatized with a fluorescent dye prior to formation of the complete chelator ring. The representative synthetic methods are summarized in FIGS. 1-12. The appropriate methods may be used to synthesize the desired compounds of the invention.

As the metal binding ability of the resulting chelators may be significantly influenced by the nature of the amine substituents, careful selection of the alkylating agent may be necessary to prepare a reporter for a particular target ion. BAPTA chelators are typically selective for calcium ion. Where the chelator nitrogens are alkylated by methyl bromoacetate, the resulting bis-aza-crown ether is typically selective for sodium ions. If the alkylating agent is 2-picolyl chloride, the resulting crown ether is typically selective for zinc ions. Selection of an alkylating agent that incorporates a precursor to a reactive functional group is useful for producing chemically reactive compounds of the invention, as well as acting as a useful intermediate for preparing conjugates, as described above.

The syntheses of chelating groups selective for different metal ions has been well described in the literature (U.S. Pat. No. 4,603,209; U.S. Pat. No. 5,049,673; U.S. Pat. No. 4,849,362; U.S. Pat. No. 5,453,517; U.S. Pat. No. 5,501,980; U.S. Pat. No. 5,459,276; U.S. Pat. No. 5,501,980; U.S. Pat. No. 5,459,276; U.S. Pat. No. 5,516,911; U.S. Application No. 2002/0164616; each of which is incorporated by reference). These methods can be readily adapted to prepare chelator intermediates useful for the synthesis of the compounds of the invention.

Synthesis of conventional xanthene dyes such as fluoresceins, rhodamines and rhodols typically involves the condensation of two equivalents of resorcinol (for fluoresceins), aminophenol (for rhodamines) or a mixture of a resorcinol and an aminophenol (for rhodols) with a carbonyl-containing moiety such as a phthalic acid derivative or benzaldehyde. However, in the synthesis of the xanthene indicators of the invention, the desired resorcinol or aminophenol is condensed with a chelator intermediate that contains a carbonyl group, yielding either the reduced xanthene (where the chelator contains an aldehyde) or the oxidized xanthene (where the chelator intermediate ether contains a carboxylic acid, anhydride or acyl halide) bound directly to the chelating moiety. This synthetic method is illustrated in FIGS. 7, 9 and 11.

An oxidation step is typically required after condensation of a formyl-substituted chelator with the fluorophore precursors. Optionally, the dihydro condensation product may be isolated and subsequently oxidized with air or by standard chemical oxidants, such as DDQ or chloranil. For some fluorophores, the oxidation reaction is enhanced by acidic reaction conditions. These mild oxidation reaction conditions tolerate a wide variety of substituents on the fluorophore and/or crown ether of the resulting indicators. These carbonyl-derived methods are well described in the literature (K. R. Gee, Z. Zhou, W. Qian and R. Kennedy, J. Am. Chem. Soc. 2002, 124, 776; J. P. Bacci, A. M. Keramey and D. L. Van Vranken, J. Org. Chem. 2005, 70, 9051; U.S. Application No. 2002/0164616; each of which is incorporated by reference).

Unsymmetrical xanthene dyes are typically constructed using statistical methods, using a 1:1 mixture of the desired resorcinols or aminophenols in the condensation reaction, and purifying the desired product from the resulting statistical mixture of products using methods known in the art. This synthetic method is represented by FIG. 11. In addition, unsymmetrical xanthene dyes can be prepared from benzophenone intermediate as shown in FIG. 12.

Alternatively the fluorescent indicators of the invention can be prepared via the condensation of properly protected xanthones with a chelator anion, typically prepared from the corresponding chelator bromide or iodide. This organometallic chemistry is also well described in the literature (C. Chen, R. Yeh and D. S. Lawrence, J. Am. Chem. Soc. 2002, 124, 3840; U.S. Pat. No. 5,049,673); Y. Urano, M. Kamiya, K. Kanda, T. Ueno, K. Hirose and T. Nagano, J. Am. Chem. Soc. 2005, 127, 4888; each of which is incorporated by reference) and can be readily adapted to synthesize the compounds of the invention (see FIGS. 6, 8 and 10).

Post-condensation modifications of both the chelator and the fluorophore moiety are typically analogous to known methods of indicator modification. For example, the reduction of nitro substituents to amino groups, the conversion of carboxy substituents to cyano groups, and the preparation of esters of carboxylic acids, including acetoxymethyl esters (see FIGS. 6-11). Additionally, a given salt or counterion of the indicators of the invention may be readily converted to other salts by treatment with ion-exchange resins, selective precipitation, and basification, as is well-known in the art.

Post-condensation modifications of xanthylium dyes are well known. For instance, the xanthenone portion of the dye can be halogenated by treatment with an appropriate halogenating agent, such as liquid bromine. Xanthenes containing unsaturated fused rings can be hydrogenated to the saturated derivatives.

The reduced and oxidized versions of the xanthene indicators are freely interconvertible by well-known oxidation or reduction reagents, including borohydrides, aluminum hydrides, hydrogen/catalyst, and dithionites. Care must be exercised to select an oxidation or reducing agent that is compatible with the chelator used. A variety of oxidizing agents mediate the oxidation of dihydroxanthenes, including molecular oxygen in the presence or absence of a catalyst, nitric oxide, peroxynitrite, dichromate, triphenylcarbenium and chloranil. The dihydroxanthenes may also be oxidized electrochemically, or by enzyme action, including the use of horseradish peroxidase in combination with peroxides or by nitric oxide.

Rather than condensing the fluorophore moiety precursors directly with substituted chelators, the preformed fluorophore moiety may be covalently bound to the chelator via a conventional cross-linking reaction. A wide variety of chemically reactive or potentially chemically reactive and fluorescent fluorescein, rhodamine, rhodol, benzoxanthenes, dibenzoxanthene and other xanthene oxygen heterocycles that absorb maximally beyond about 490 nm are commercially available as described by Haugland, HANDBOOK OF FLUORESCENT PROBES AND RESEARCH CHEMICALS (7th ed., 1999), as described above, or in other literature references. The nature of the bond that links fluorophore moiety to the chelator appears to have an effect on the optical response of the fluorophore moiety to ion binding, sometimes a significant effect. Acceptability of the linking chemistry can be determined by titration of the resultant indicator with the ion of interest over the target range of response.

Applications of the Fluorescent Indicators of the Invention

The indicators disclosed herein possess particular utility for the detection and/or quantification of metal ions in a sample of interest. Such indicators may be useful for measuring ions in extracellular spaces; in vesicles; in vascular tissue of plants and animals; biological fluids such as blood and urine; in fermentation media; in environmental samples such as water, soil, waste water and seawater; and in chemical reactors. Optical indicators for ions are important for qualitative and quantitative determination of ions, particularly in living cells. Fluorescent indicators for metal cations also permit the continuous or intermittent optical determination of these ions in living cells, and in solutions containing the ions.

In effecting such determination, the substance to be determined, or analyte, which contains the ion of interest is contacted with a fluorescent indicator as disclosed above. Complexation of the metal ion in the chelator of the indicator results in a detectable change in the fluorescence properties of the indicator. Detection and optionally quantification of the detectable change permits the ion of interest to be detected and optionally quantified.

Upon binding the target ion in the chelating moiety of the indicator, the optical properties of the attached fluorophore are generally affected in a detectable way, and this change may be correlated with the presence of the ion according to a defined standard. Compounds having relatively long wavelength excitation and emission bands can be used with a variety of optical devices and require no specialized (quartz) optics, such as are required by indicators that are excited or that emit at shorter wavelengths. These indicators are suitable for use in fluorescence microscopy, flow cytometry, fluorescence microplate readers, or any other application that currently utilize fluorescent metal ion indicators.

This determination method may be based on the so-called "PET effect", or the transfer, induced by photons, of electrons (photoinduced electron transfer=PET) from the ionophoric moiety or ionophore, respectively, to the fluorophore moiety or fluorophore, respectively, which leads to a decrease in the (relative) fluorescence intensity and the fluorescence decay time of the fluorophore. Absorption and emission wavelengths, however, are not significantly affected in the process (J. R. Lakowicz in "Topics in Fluorescence Spectroscopy", Volume 4: Probe Design and Chemical Sensing; Plenum Press, New York & London (1994)).

By the binding of ions to the ionophore, the PET effect may be partly or completely inhibited, so that there is an increase in the fluorescence of the fluorophore moiety. Hence, the concentration or the activity of the ion to be determined can be deduced by measuring the change in fluorescence properties, i.e. fluorescence intensity and/or fluorescence decay time.

A variety of fluorescent indicators that are useful for the detection of biologically relevant soluble free metal ions (such as $Ca^{2+}$, $Mg^{2+}$ and $Zn^{2+}$) have been described that utilize oxygen-containing anionic or polyanionic chelators to bind to metal ions. In general, a useful property for metal ion indicators is selectivity, or the ability to detect and/or quantify a selected metal ion in the presence of other metal ions. Discrimination of $Ca^{2+}$, $Na^+$ and $K^+$ ions in the presence of other metal ions is particularly advantageous in certain biological or environmental samples. For most biological applications, it is useful that the indicators be effective in aqueous solutions. It is also beneficial if the indicator absorbs and emits light in the visible spectrum where biological materials typically have low intrinsic absorbance or fluorescence.

Optical methods using fluorescence detection of metal ions permit measurement of the entire course of ion flux in a single cell as well as in groups of cells. The advantages of monitoring transport by fluorescence techniques include the high level of sensitivity of these methods, temporal resolution, modest demand for biological material, lack of radioactivity, and the ability to continuously monitor ion transport to obtain kinetic information (Eidelman, O. Cabantchik, Z. I. Biochim. Biophys. Acta, 1989, 988, 319-334). The general principle of monitoring transport by fluorescence is based on having compartment-dependent variations in fluorescence properties associated with translocation of compounds.

Optical methods were developed initially for measuring $Ca^{2+}$ ion flux (U.S. Pat. No. 5,049,673, hereby incorporated by reference; Scarpa, A. Methods of Enzymology, 1979, 56, 301 Academic Press, Orlando, Fla.; Tsien, R. Y. Biochemistry, 1980, 19, 2396; Grynkiewicz, G., Poenic, M., Tsien, R. Y. J. Biol. Chem., 260, 3440) and have been modified for high-throughput assays (U.S. Pat. No. 6,057,114, hereby incorporated by reference). The flux of $Ca^{2+}$ ion is typically performed using calcium-sensitive fluorescent dyes such as Fluo-3, Fluo-4, Calcium Green, and others. (Molecular Probes Inc., Handbook of Fluorescent probes and research chemicals, 7th edition, chapter 1, Eugene, Oreg.).

In particular, fluorescent indicators utilizing a polycarboxylate BAPTA chelator have been previously described. A determination method utilizing aza-cryptands as the chelator moiety and using xanthenes and coumarins as fluorophores has also been described (U.S. Pat. No. 5,439,828 and US Patent Application 20020164616; each hereby incorporated by reference). These aza-cryptand may, depending on their structure, exhibit selectivity for lithium, sodium or potassium ions. Some fluorescent indicators selective for $Li^+$, $Na^+$ and $K^+$ in aqueous or organic solution have also been described, based on the chemical modification of crown ethers (U.S. Pat. No. 5,134,232; U.S. Pat. No. 5,405,975, each hereby incorporated by reference).
ion.

The desired indicator compound is generally prepared for use as a detection reagent by dissolving the indicator in solution at a concentration that is optimal for detection of the indicator at the expected concentration of the target ion. Modifications that are designed to enhance permeability of the indicator through the membranes of live cells, such as functionalization of carboxylic acid moieties using acetoxymethyl esters and acetates, may require the indicator to be predissolved in an organic solvent such as dimethylsulfoxide (DMSO) before addition to a cell suspension, where the indicators may then readily enter the cells. Intracellular enzymes then cleave the esters, generating more polar acids and phenols which are then well-retained inside the cells. For applications where permeability of cell-membranes is required, the indicators of the invention are typically substituted by only one fluorophore.

The specific indicator used in a particular assay or experiment may be selected based on the desired affinity for the target ion as determined by the expected concentration range in the sample, the desired spectral properties, and the desired selectivity. Initially, the suitability of a material as an indicator of ion concentration is commonly tested by mixing a constant amount of the indicating reagent with a measured amount of the target ion under the expected experimental conditions.

Where the binding of an ion in the metal ion-binding moiety of the indicator results in a detectable change in spectral properties of the indicator compound, that indicator may be used for the detection and/or quantification of that ion (the target ion). Although the change in spectral properties may include for example a change in absorption intensity or wavelength, preferably the change in spectral properties is a detectable fluorescence response. Preferred indicators display a high selectivity, that is, they show a sufficient rejection of non-target ions. The interference of a non-target ion is tested by a comparable titration of the indicator with that ion. In one aspect of the invention, the target ions for the indicators of the present invention are selected from $Ca^{2+}$, $Na^+$ and $K^+$.

A detectable fluorescence response, as used herein, is a change in a fluorescence property of the indicator that is capable of being perceived, either by direct visual observation or instrumentally, the presence or magnitude of which is a function of the presence and/or concentration of a target metal ion in the test sample. This change in a fluorescence property is typically a change in fluorescence quantum yield, fluorescence polarization, fluorescence lifetime, a shift in excitation or emission wavelength, among others, or a combination of one or more of such changes in fluorescence properties. The detectable change in a given spectral property is generally an increase or a decrease. However, spectral changes that result in an enhancement of fluorescence intensity and/or a shift in the wavelength of fluorescence emission or excitation may also be useful. The change in fluorescence on ion binding may be due to conformational or electronic changes in the indicator that may occur in either the excited or ground state of the fluorophore, due to changes in electron density at the ion binding site, due to quenching of fluorescence by the bound target metal ion, or due to any combination of these or other effects.

A typical indicator for a specific target ion is an indicator that exhibits at least a 50-fold change in net fluorescence emission intensity (either an increase or decrease), or at least a 1 nanosecond difference in fluorescence lifetime (either shorter or longer). In one aspect of the invention, the indicator exhibits a 50-fold or greater change in net fluorescence emission intensity, and/or a 100% change in fluorescence lifetime in the presence of the target ion. In an alternative aspect of the invention, the indicator exhibits a shift in excitation or emission wavelength of at least 10 nm (either to shorter or longer wavelength), more preferably exhibiting a wavelength shift of 25 nm or greater.

The spectral response of a selected indicator to a specific metal ion is a function of the characteristics of the indicator in the presence and absence of the target ion. For example, binding to a metal ion may alter the relative electron densities of the fluorophore and the metal binding site. Additionally, or in the alternative, some metal ions may quench fluorescence emission when in close proximity to a fluorophore (heavy atom quenching). In one embodiment of the invention, the indicator is essentially nonfluorescent or exhibits low fluorescence in target ion-free solution and exhibits an increase in fluorescence intensity or fluorescence lifetime (or both) upon target metal ion binding. In yet another embodiment of the invention, the fluorescence intensity remains approximately the same but there is a shift in the excitation or emission spectrum, or both, upon metal ion binding.

As the optical response of the indicating reagent is typically determined by changes in fluorescence, the threshold of detection of the target ion will be dependent upon the sensitivity of the equipment used for its detection.

If the optical response of the indicator will be determined using fluorescence measurements, the sample of interest is typically stained with indicator concentrations of $10^{-9}$ M to $10^{-3}$ M. The most useful range of analyte concentration includes about one log unit above and below the dissociation constant of the ion-indicator complex. This dissociation constant may be determined by titration of the indicator with known concentrations of the target ion, usually over the range of virtually zero concentration to approximately 100 mM of the target ion, depending on which ion is to be measured and which indicator is being used. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects are readily determined, and can be taken into account when calibrating a selected indicator.

The indicator is typically combined with a sample in a way that will facilitate detection of the target ion concentration in the sample. The sample is generally a fluid or liquid suspension that is known or suspected to contain the target ion. Representative samples include intracellular fluids from cells such as in blood cells, cultured cells, muscle tissue, neurons and the like; extracellular fluids in areas immediately outside of cells; fluids in vesicles; fluids in vascular tissue of plants and animals; biological fluids such as blood, saliva, and urine; biological fermentation media; environmental samples such as water, soil, waste water and sea water; industrial samples such as pharmaceuticals, foodstuffs and beverages; and samples from chemical reactors. Detection and quantitation of the target ion in a sample can help characterize the identity of an unknown sample, or facilitate quality control of a sample of known origin.

In one embodiment of the invention, the sample includes cells, and the indicator is combined with the sample in such a way that the indicator is added within the sample cells. By selection of the appropriate chelating moiety, fluorophore, and the substituents thereon, indicators may be prepared that will selectively localize in a desired organelle, and provide measurements of the target ion in those organelles. Conjugates of the indicators of the invention with organelle-targeting peptides may be used to localize the indicator to the selected organelle, facilitating measurement of target ion presence or concentration within the organelle (as described in U.S. Pat. No. 5,773,227, hereby incorporated by reference). Alternatively, selection of a lipophilic fluorophore, or a fluorophore having predominantly lipophilic substituents may result in localization of the indicator in lipophilic environments in the cell, such as cell membranes. Selection of cationic indicators will typically result in localization of the indicator in mitochondria.

In one embodiment of the invention, the indicator compound of the invention optionally further includes a metal ion. In another embodiment, the compounds of the invention, in any of the embodiments described above, are associated, either covalently or noncovalently, with a surface such as a microfluidic chip, a silicon chip, a microscope slide, a microplate well, or another solid or semisolid matrix, and is combined with the sample of interest as it flows over the surface. In this embodiment, the detectable optical response may therefore be detected on the matrix surface itself, typically by use of instrumental detection. This embodiment of the invention may be particularly suited to high-throughput screening using automated methods.

The fluorescence response of the indicator to the target ion may be detected by various means that include without limitation measuring fluorescence changes with fluorometers, fluorescence microscopes, laser scanners, flow cytometers, and microfluidic devices, as well as by cameras and other imaging equipment. These measurements may be made remotely by incorporation of the fluorescent ion sensor as part of a fiber optic probe. The indicator may be covalently attached to the fiber optic probe material, typically glass or functionalized glass (e.g., aminopropyl glass) or the indicator may be attached to the fiber optic probe via an intermediate polymer, such as polyacrylamide. The indicator solution is alternatively incorporated non-covalently within a fiber optic probe, as long as there is a means whereby the target ion may come into contact with the indicator solution. More preferably, the BAPTA indicators of the invention are used with a fluorescence microplate reader that is equipped with an automated liquid handling system such as FLIPR, FLEXSTATION and FDSS.

In another aspect of the invention, the fluorescent ion indicators of the invention may be used in combination with one or more non-fluorescent dyes that are not substantially cell-permeable in order to reduce the background fluorescence analogous to the methods described in U.S. Pat. No. 6,420,183, hereby incorporated by reference. Non-fluorescent dyes and dye mixtures that have large water solubilities and minimal effects on the physiology of the cells are preferred for this application. More preferably are water-soluble azo dyes (such as trypan blue), which have been used in cell-based assays for many years (H. W. Davis, R. W. Sauter. Histochemistry, 1977, 54, 177; W. E. Hathaway, L. A. Newby, J. H. Githens, Blood, 1964, 23, 517; C. W. Adams, O. B. Bayliss, R. S. Morgan, Atherosclerosis, 1977, 27, 353).

The screening methods described herein can be performed with cells growing in or deposited on solid surfaces. A common technique is to use a microwell plate where the fluorescence measurements are performing using a commercially available fluorescent plate reader. These methods lend themselves to use in high throughput screening using both automated and semi-automated systems.

Using the indicators of the present invention, the measurement of fluorescence intensity can provide a sensitive method for monitoring changes in intracellular ion concentrations. Thus, fluorescence measurements at appropriate excitation and emission wavelengths provide a fluorescence readout which is sensitive to the changes in the ion concentrations.

In one embodiment, the invention includes a) adding a compound as described above to a sample containing a cell; b) incubating the sample for a time sufficient for the compound to be loaded into the cell and an indicator compound to be generated intracellularly; c) illuminating the sample at a wavelength that generates a fluorescence response from the indicator compound; d) detecting a fluorescence response from the indicator compound; and e) correlating the fluorescence response with the presence of intracellular calcium.

In one aspect of the invention, the disclosed method is useful for screening potential therapeutic drugs, for example drugs which may affect ion concentrations in biological cells. These methods may include measuring ion concentrations as described above in the presence and absence (as a control measurement) of the test sample. Control measurements are usually performed with a sample containing all components of the test sample except for the putative drug being screened. Detection of a change in ion concentration in the presence of the test agent relative to the control indicates that the test agent is active. Ion concentrations can also be determined in the presence or absence of a pharmacologic agent of known activity (i.e., a standard agent) or putative activity (i.e., a test agent). A difference in ion concentration as detected by the methods disclosed herein allows one to compare the activity of the test agent to that of a standard agent of known activity. It will be recognized that many combinations and permutations of drug screening protocols are known to one of skill in the art and they may be readily adapted to use with the method of ion concentration measurement disclosed herein to identify compounds which affect ion concentrations.

In yet another aspect of the invention, the disclosed method may facilitate the screening of test samples in order to identify one or more compounds that are capable of modulating the activity of an ion channel, pump or exchanger in a membrane, and the method further includes stimulating the cell, monitoring changes in the intensity of the fluorescence response from the indicator compound, and correlating the changes in fluorescence intensity with changes in intracellular calcium levels.

An additional method may be used to evaluate the efficacy of a stimulus that generates a target ion response, including (a) loading a first set and a second set of cells with the ion indicators of the invention which monitor ion concentrations; (b) optionally, exposing both the first and second set of cells to a stimulus which modulates the ion channel, pump or exchanger; (c) exposing the first set of cells to the test sample; (d) measuring the ion concentrations in the first and second sets of cells; and (e) relating the difference in ion concentrations between the first and second sets of cells to the ability of a compound in the test sample to modulate the activity of an ion channel, pump or exchanger in cells. In one aspect of the recited method, the method may include the addition of probenecid or a probenecid derivative to the sample.

One or more of the methods disclosed herein may be enhanced by the addition of a cell-impermeant and non-fluorescent dye to the sample, such that the dye remains in the extracellular solution, and acts as an acceptor dye for energy transfer from the indicator compound, thereby decreasing background signal from the sample solution. In one aspect of the method, the cell-impermeant and non-fluorescent dye is a water-soluble azo dye.

Ion channels of particular interest may include, but are not limited to, sodium, calcium, potassium, nonspecific cation, and chloride ion channels, each of which may be constitutively open, voltage-gated, ligand-gated, or controlled by intracellular signaling pathways.

Biological cells of potential interest for screening application may include, but are not limited to, primary cultures of mammalian cells, cells dissociated from mammalian tissue, either immediately or after primary culture. Cell types may include, but are not limited to white blood cells (e.g. leukocytes), hepatocytes, pancreatic beta-cells, neurons, smooth muscle cells, intestinal epithelial cells, cardiac myocytes, glial cells, and the like. The disclosed method may also include the use of recombinant cells into which ion transporters, ion channels, pumps and exchangers have been inserted and expressed by genetic engineering. Many cDNA sequences for such transporters have been cloned (see U.S. Pat. No. 5,380,836 for a cloned sodium channel, hereby incorporated by reference) and methods for their expression in cell lines of interest are within the knowledge of one of skill in the art (see, U.S. Pat. No. 5,436,128, hereby incorporated by reference). Representative cultured cell lines derived from humans and other mammals include LM cells, HEK-293 (human embryonic kidney cells), 3T3 fibroblasts, COS cells, CHO cells, RAT1 and HepG2 cells, Hela cells, $U_2OS$ cells and Jurkat cells etc.

Assay Kits

Due to the advantageous properties and the simplicity of use of the disclosed ion indicator compounds, they possess particular utility in the formulation of a kit for the complexation, detection, or quantification of selected target ions. An exemplary kit may include one or more compounds or compositions of the invention in any of the embodiments described above, either present as a pure compound, in a suitable carrier composition, or dissolved in an appropriate stock solution. The kit may further include instructions for the use of the indicator compound to complex or detect a desired target ion. The kit may further include one or more additional components, such as an additional detection reagent.

The indicator of the invention may be present in the kit associated with a surface, such as a chip, microplate well, or other solid or semi-solid matrix.

The additional kit components may be selected from, without limitation, calibration standards of a target ion, ionophores, fluorescence standards, aqueous buffers, surfactants and organic solvents. The additional kit components may be present as pure compositions, or as aqueous solutions that incorporate one or more additional kit components. Any or all of the kit components optionally further comprise buffers.

In one aspect of the disclosed kit, the kit includes at least one indicator compound as described above, and a non-fluorescent and cell-impermeant quencher dye. The non-fluorescent and cell-impermeant quencher dye is optionally present with the indicator compound in a combined composition, such as a mixed powder or a solution. Alternatively, or in addition, the cell-impermeant quencher dye is present in a container distinct from the indicator compound.

The examples provided below illustrate selected aspects of the invention. They are not intended to limit or define the entire scope of the invention.

EXAMPLES

Example 1

Preparation of Compound 205

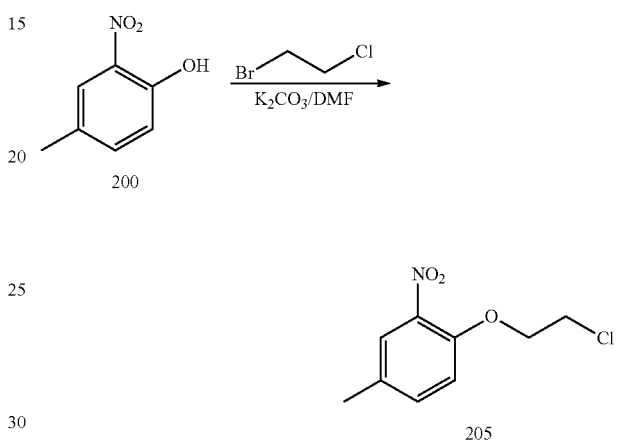

Compound 205 is analogously prepared according to the procedure of U.S. Application No. 2002/0164616, hereby incorporated by reference. A mixture of Compound 200 (15 g) and 1-bromo-2-chloroethane (50 g) is dissolved in DMF at room temperature. To the reaction mixture $K_2CO_3$ is added with stirring. The reaction mixture is stirred at room temperature for 4-6 days. The reaction mixture is poured into water, and the resulted solid is collected. The dried solid is purified on a silica gel column using a gradient of hexanes/ethyl acetate to give a light yellow solid.

Example 2

Preparation of Compound 215

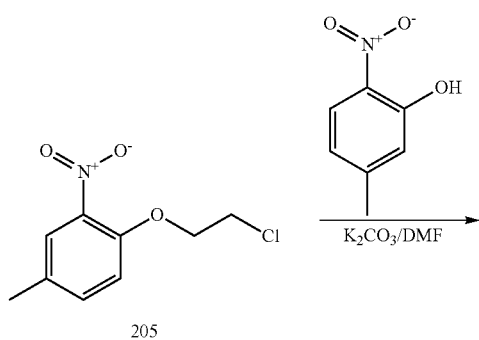

-continued

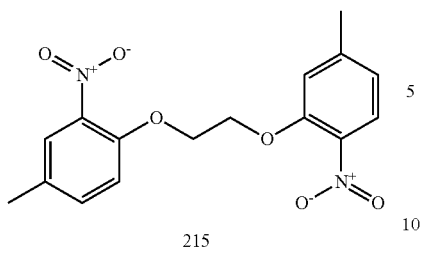

215

Compound 215 is prepared analogously to the procedure of U.S. Pat. No. 5,049,673 and U.S. Application No. 2002/0164616 (hereby incorporated by reference). The mixture of Compound 205 (20 g) and 5-methyl-2-nitrophenol (20 g) is dissolved in DMF at room temperature. To the reaction mixture $K_2CO_3$ is added, and the reaction mixture is stirred at 140-160° C. for 12-24 h. The reaction mixture is cooled, and poured into water, and resulted solid is collected. The dried solid is purified on a silica gel column using a gradient of hexanes/ethyl acetate to give a very light yellow solid.

Example 3

Preparation of Compound 225

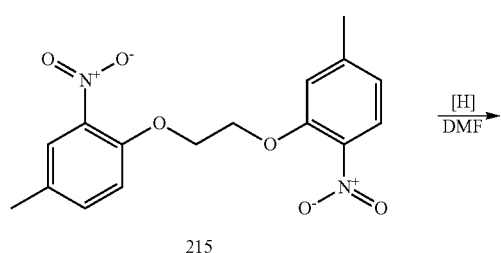

225

Compound 225 is prepared analogously to the procedure of U.S. Pat. No. 5,049,673 and U.S. Application No. 2002/0164616, each hereby incorporated by reference. Compound 215 is dissolved in DMF at room temperature. To the solution 10% palladium on carbon is added. The reaction mixture is hydrogenated at 40-45 psi for 3-4 h. The reaction mixture is filtered through diatomaceous earth to remove the catalyst that is washed with DMF. The combined DMF solution is poured into water. The formed solid is collected by filtration, and washed with water. The dried solid is purified on a silica gel column using a gradient of chloroform/ethyl acetate to give an off-white solid.

Example 4

Preparation of Compound 235

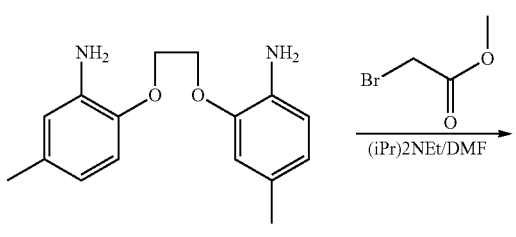

225

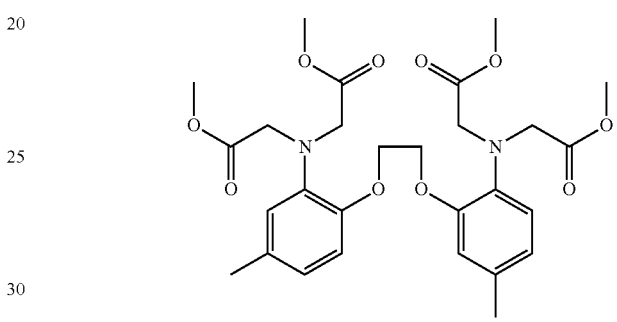

235

Compound 235 is prepared analogously to the procedure of U.S. Pat. No. 5,049,673. Compound 225 (25 g) is dissolved in DMF at room temperature. To the reaction mixture $(iPr)_2NEt$ (100 mL) is added with stirring, and then methyl bromoacetate (50 mL) is added with stirring. The reaction mixture is heated at 70-90° C. for 24-36 h. The concentrated DMF solution is poured into water. The formed solid is collected by filtration, and washed with water. The dried solid is purified on a silica gel column using a gradient of chloroform/ethyl acetate to give an off-white solid.

Example 5

Preparation of Compound 245

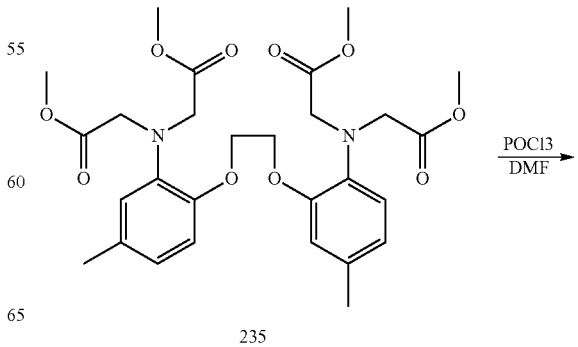

235

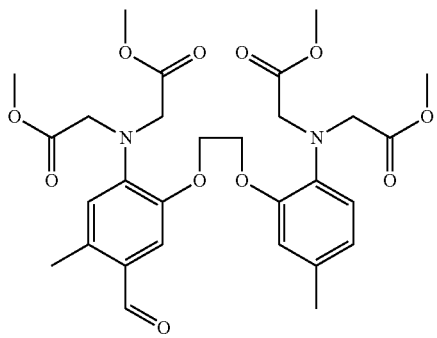

245

Compound 245 is prepared analogously to the procedure of U.S. Application No. 2002/0164616. DMF (50 mL) is cooled ice in water bath. To the DMF is added POCl₃ dropwise. The resulted solution is stirred at room temperature for 1-2 h, and cooled to 5-10° C. To the POCl₃/DMF mixture is dropwise added a solution of compound 235 (10 g) in DMF (100 mL) over 40-45 min. The reaction mixture is heated at 40-45° C. for 12-24 h. The resulted mixture is cooled to room temperature, and concentrated in vacuo, and poured into ice/water. The suspension is filtered to collect the solid that is washed with water. The dried solid is purified on a silica gel column to give of off-white solid using a gradient of chloroform/ethyl acetate.

Example 6

Preparation of Compound 252

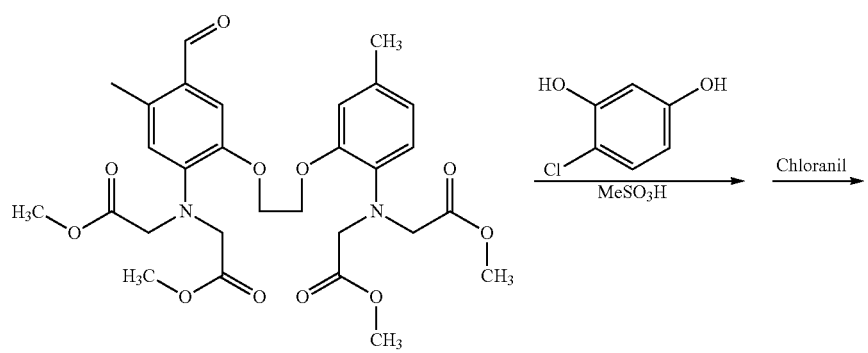

245

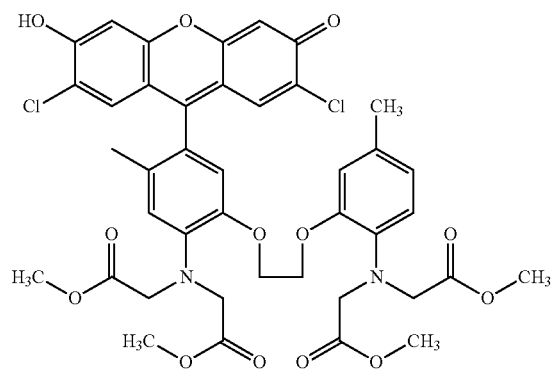

252

Compound 252 is prepared analogously to the procedures of U.S. Application No. 2002/0164616; K. R. Gee, Z. L. Zhou, W. J. Qian, R. Kennedy, J. Am. Chem. Soc. 2002, 124, 776; V. V. Martin, A. Rothe, Z. Diwu and K. Gee, Bioorg. Med. Chem. Lett. 2004, 14, 5313; and J. P. Bacci, A. M. Kearney and D. L. Van Vranken, J. Org. Chem. 2005, 70, 9051). The mixture of aldehyde 245 (2 g) and 4-chlororesorcinol (1.5 g) in MeSO$_3$H (30 mL) is stirred overnight, and then poured into NaOAc solution. The precipitated solid is filtered, washed with water and dried to give the dihydro form of Compound 252 that is directly used in the next step without additional purification. The mixture of the crude dihydro form of Compound 252 and chloranil in MeOH is heated at reflux for 12 to 24 h, then cooled to room temperature, filtered (to remove excess oxidizer), and evaporated. The residue is concentrated and purified on a silica gel column using a gradient of chloroform/methanol.

Example 7

Preparation of Compound 256

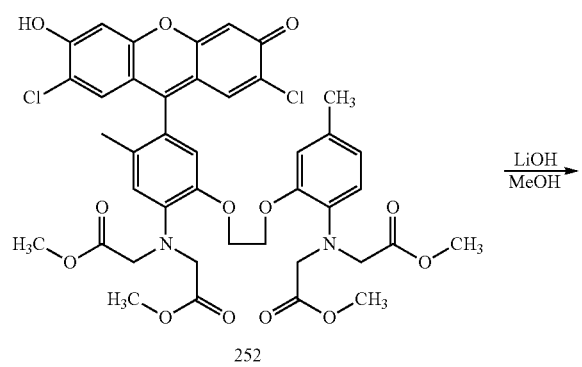

252

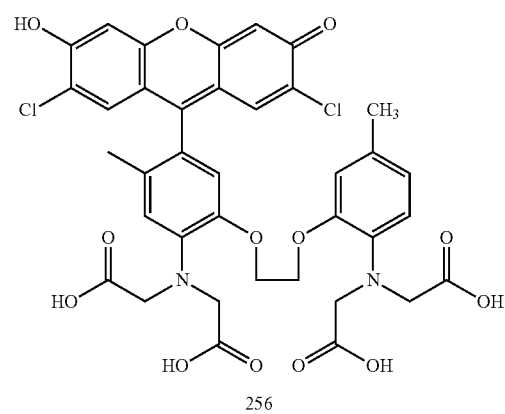

256

Compound 252 (100 mg) is suspended in 1:1 methanol/water (10 mL). To the suspension LiOH (150 mg) is added slowly while cooled in ice/water bath, and stirred at room temperature for 12-24 h. The reaction mixture is diluted with water (200 mL), and neutralized with concentrated HCl (2-3 mL). The mixture is filtered to collect the precipitate. The solid is redissolved in methanol, and further purified by HPLC to give Compound 256.

Example 8

Preparation of Compound 258

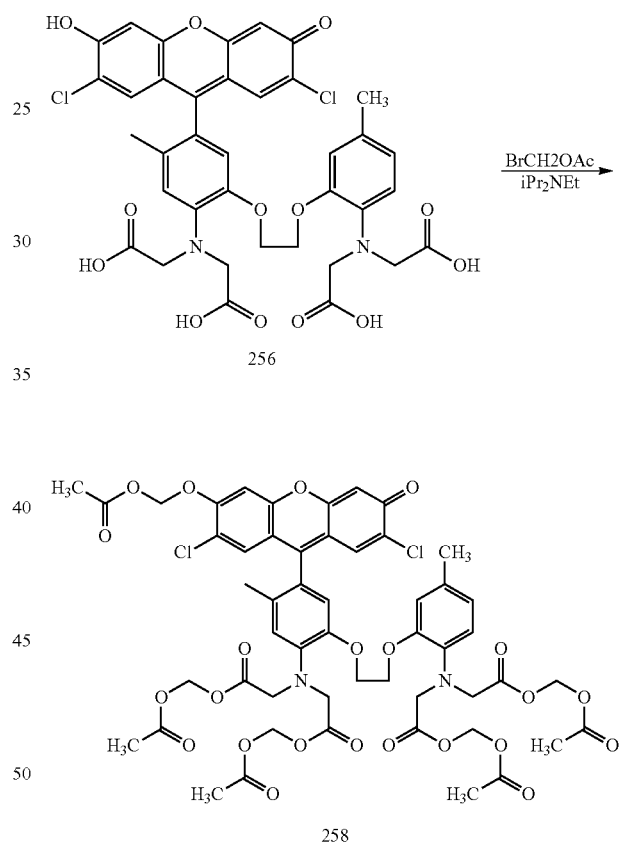

256

258

Compound 256 (50 mg) is dissolved in anhydrous DMF (3 mL) at room temperature. To the solution BrCH$_2$OAc (70 μL) in anhydrous DMF (2 mL) is slowly added while stirring in a water bath. To the resulted mixture iPr$_2$Net (130 μL) is added slowly. The resulted mixture is stirred for 24-36 h. The reaction mixture is poured into ice/water. The suspension is filtered to collect the solid that is washed with water. The dried solid is purified on a silica gel column to give an off-white solid using a gradient of chloroform/ethyl acetate.

Example 9

Preparation of Compound 265

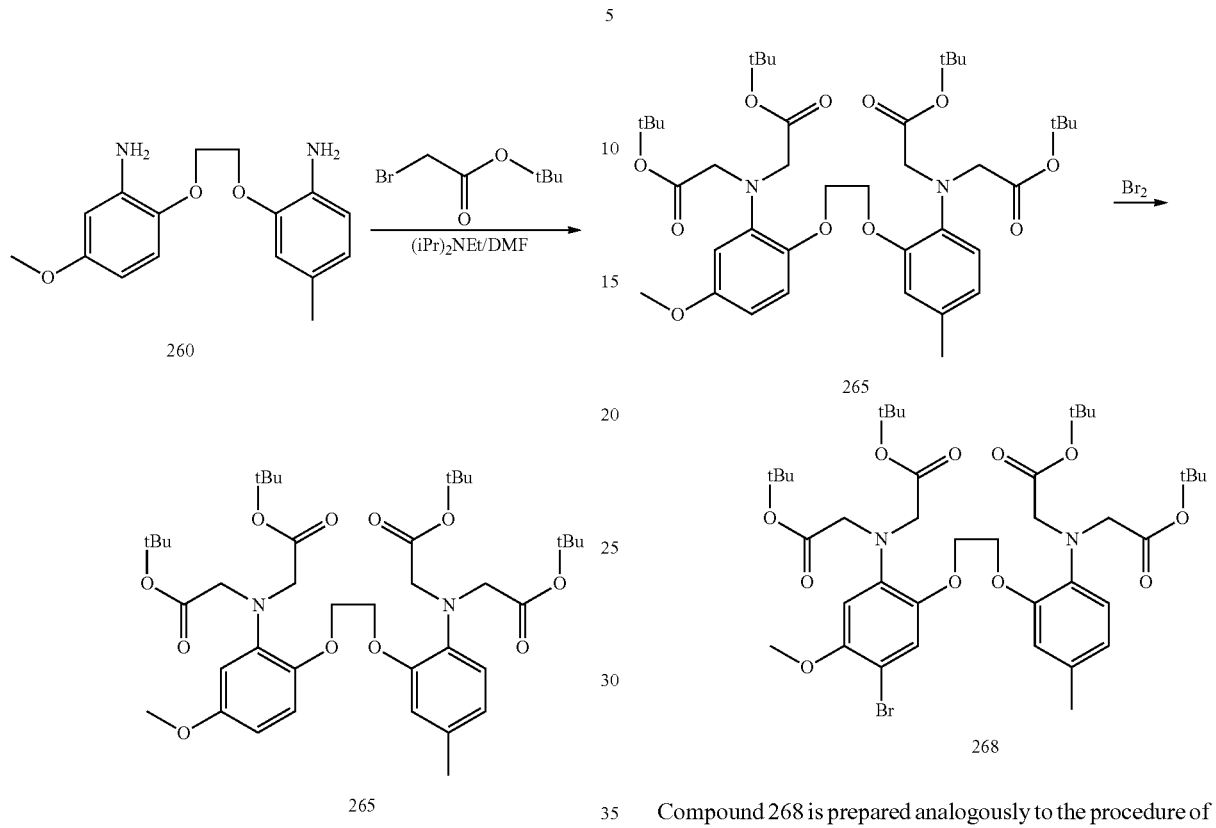

Compound 265 is prepared analogously to the procedure of U.S. Pat. No. 5,049,673. Compound 260 (10 g, prepared analogous to the procedure of Compound 235), 1,8-bis(dimethylamino)naphthalene (30 g), anhydrous sodium iodide (2 g), tert-butyl bromoacetate (50 g) and DMF (100 mL) is stirred with heating at 70-90° C. for 18 hours. The concentrated DMF solution is poured into water. The formed solid is collected by filtration, and washed with water. The dried solid is purified on a silica gel column to give an off-white solid.

Example 10

Preparation of Compound 268

Compound 268 is prepared analogously to the procedure of U.S. Pat. No. 5,049,673. Compound 265 (10 g) is dissolved in dichloromethane (100 mL) and cooled to −78° C. Pyridine (0.2 mL) is added and the mixture is stirred while bromine (3 g) in dichloromethane (20 mL) is added. The mixture is allowed to warm up to room temperature and then evaporated in vacuo. The residue is purified on a silica gel column using a gradient of chloroform/ethyl acetate to give an off-white solid.

Example 11

Preparation of Compound 275

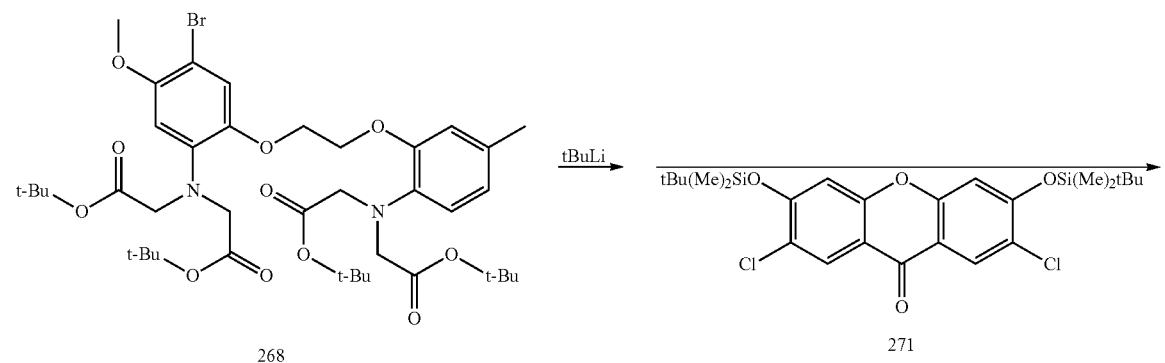

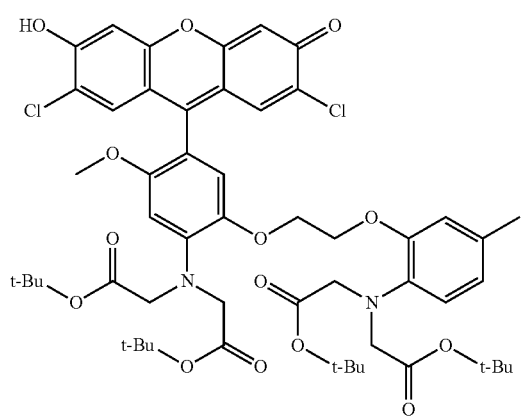

272

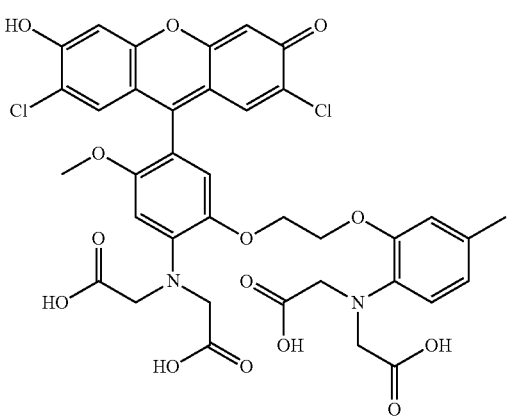

275

Compound 275 is prepared analogously to the procedure of U.S. Pat. No. 5,049,673. Compound 268 (150 mg) is dissolved in 2-methyl-tetrahydrofuran (5 mL) and stirred at −150° C. in a liquid nitrogen-isopentane bath. Tertiary butyllithium (6 equivalents) in hexane is added and the metallation monitored by thin layer chromatography of small samples quenched into water. Compound 271 (100 mg, see Parham, W. E., and Bradscher, C. K., Acc. Chem. Res., 1982, 15, 300; U.S. Pat. No. 5,049,673), dissolved in tetrahydrofuran, is added dropwise to the reaction mixture. Stirring is continued for another 30 minutes. The reaction mixture is quenched with water in tetrahydrofuran and then allowed to warm up to room temperature, and extracted twice with ethyl acetate. The combined organic extracts are washed with brine and evaporated to dryness. The residue is then stirred with acetic acid to convert all the leuco-base into the desired dye. Evaporation of the acetic acid in vacuo leaves a gummy residue which is purified by column chromatography on silica gel using a gradient of chloroform/ethyl acetate/methanol to give pure Compound 272.

Compound 272 (10 mg) is dissolved in acetic acid (1 mL) and BF$_3$ etherate (0.1 mL) is added. The resulting solution is stirred at room temperature overnight. The solution is then evaporated in vacuo. The crude product is further purified by HPLC.

Example 12

Preparation of Compound 280

Compound 280 is prepared analogously to the procedure of Compound 256.

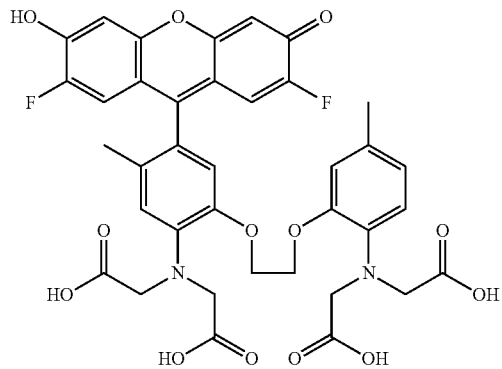

280

Example 13

Preparation of Compound 282

Compound 282 is prepared analogously to the procedure of Compound 256.

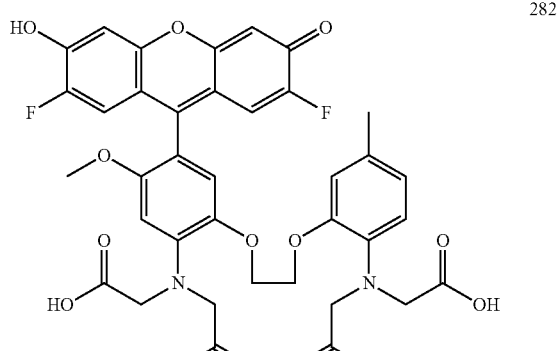

282

Example 14
Preparation of Compound 284
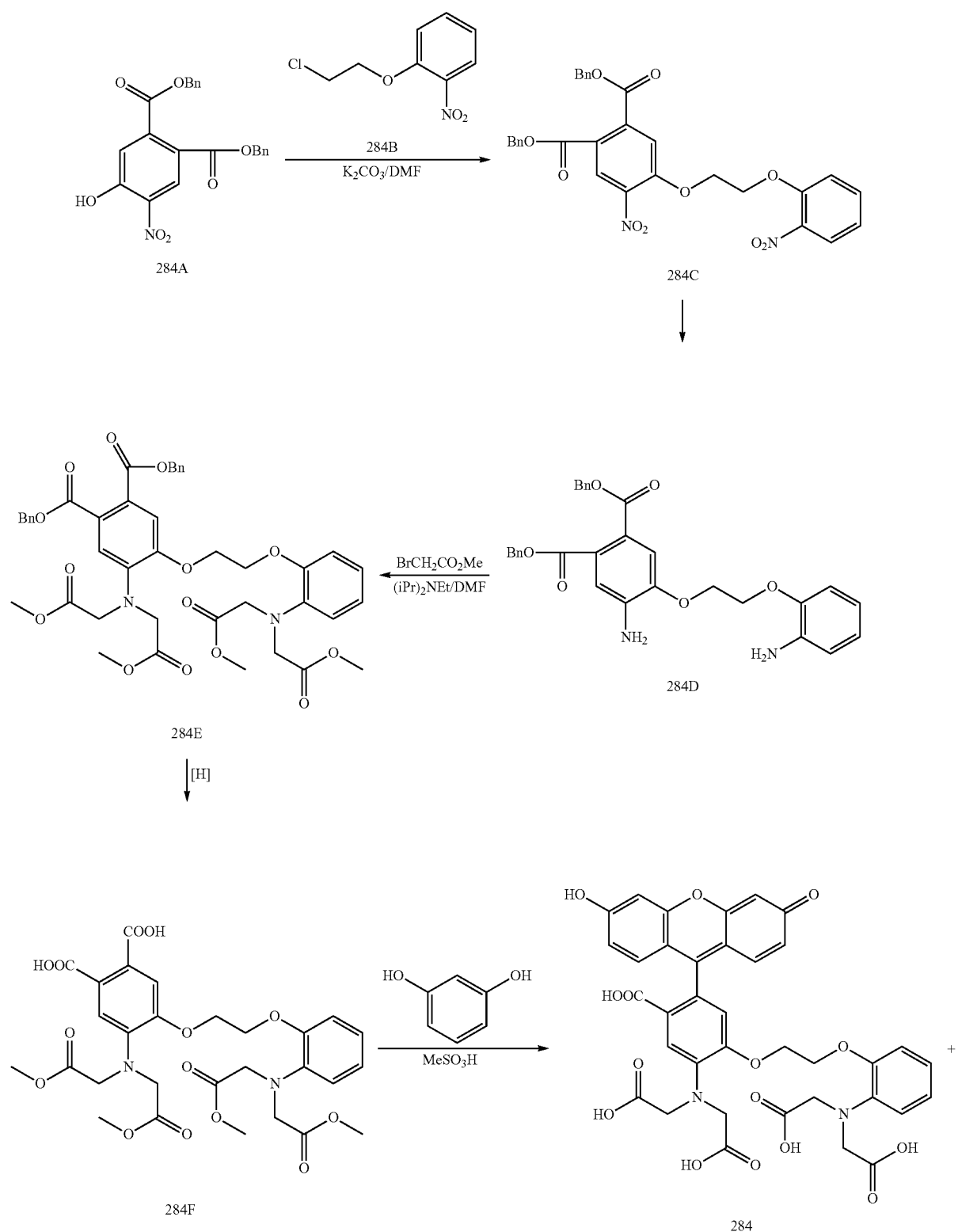

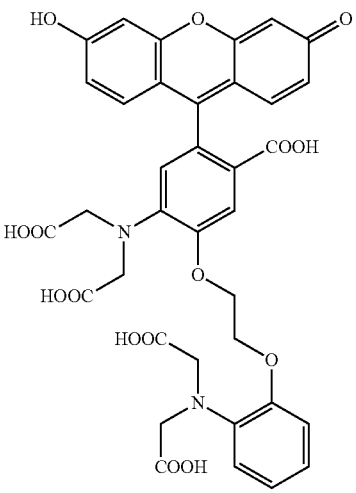

284G

Compound 284A (20 g, Shaanxi Zhendi Chemical Biology, Ltd.) is converted to Compound 284C (22 g) analogously to the protocol of Compound 215.

Compound 284C (12 g) is dissolved in ethanol. To the ethanol solution is added 23 g stannous chloride hydrate. The reaction mixture is heated at reflux until Compound 284C is completely consumed, cooled to room temperature, and poured into ice water. The reaction mixture is neutralized with sodium carbonate to have pH=6-7, and filtered to collect the solid that is further purified on a silica gel column eluted with a gradient of chloroform/methanol to give pure Compound 284D.

Compound 284D (10 g) is converted to Compound 284E analogously according to the protocol of Compound 235.

Compound 284E is dissolved in DMF at room temperature. To the solution palladium on carbon is added. The reaction mixture is hydrogenated until Compound 284E is completely consumed. The reaction mixture is filtered through diatomaceous earth to remove the catalyst which is washed with DMF. The combined DMF solution is poured into water. The formed solid is collected by filtration, and washed with water. The dried solid is purified on a silica gel column using a gradient of chloroform/ethyl acetate to give Compound 284F as an off-white solid.

Phthalic acid 284F (6 g) is added to the solution of resorcinol (3 g) in methanesulfonic acid (10 mL). The resulting mixture is heated under dry nitrogen at 70-80° C. until Compound 284F is completely consumed. The cooled mixture is poured into ice water followed by filtration. The filtrate containing Compound 284 and its isomer 284G is dried, and purified on a silica gel column eluted with a gradient of water/acetonitrile to give the mixture of Compound 284 and its isomer 284G. The mixture of Compounds 284 and 284G is further purified by HPLC using C18 column and a gradient of 1% TFA acetonitrile-1% TFA buffer to give the pure Compound 284.

Example 15

Preparation of Compound 286

Compound 286 is prepared analogously to the procedure of Compound 284 or FIG. 2.

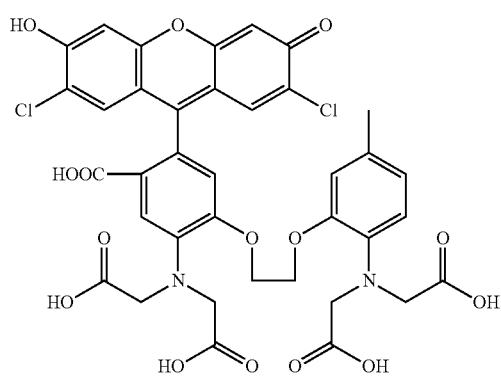

286

Example 16

Preparation of Compound 288

Compound 288 is prepared analogously to the procedure of Compound 256.

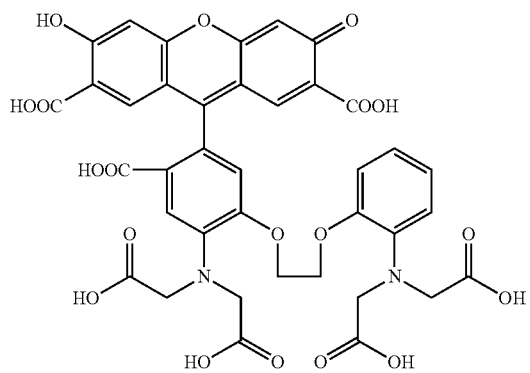

288

Example 17

Preparation of Compound 290

Compound 290 is prepared analogously to the procedure of Compound 256.

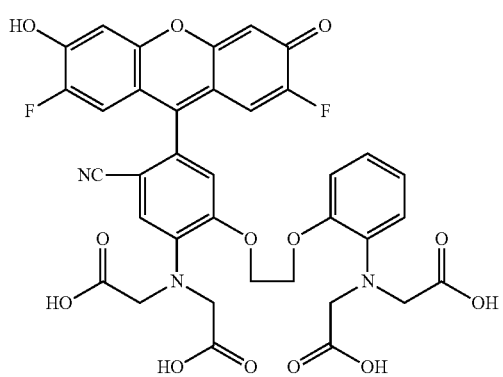

Example 18

Preparation of Compound 292

Compound 292 is prepared analogously to the procedure of Compound 256 or 275.

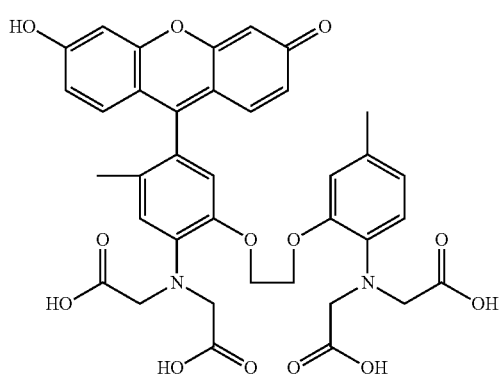

Example 19

Preparation of Compound 294

Compound 294 is prepared analogously to the procedure of Compound 258.

Example 20

Preparation of Compound 296

Compound 296 is prepared analogously to the procedure of Compound 258.

Example 21

Preparation of Compound 298

Compound 298 is prepared analogously to the procedure of Compound 258.

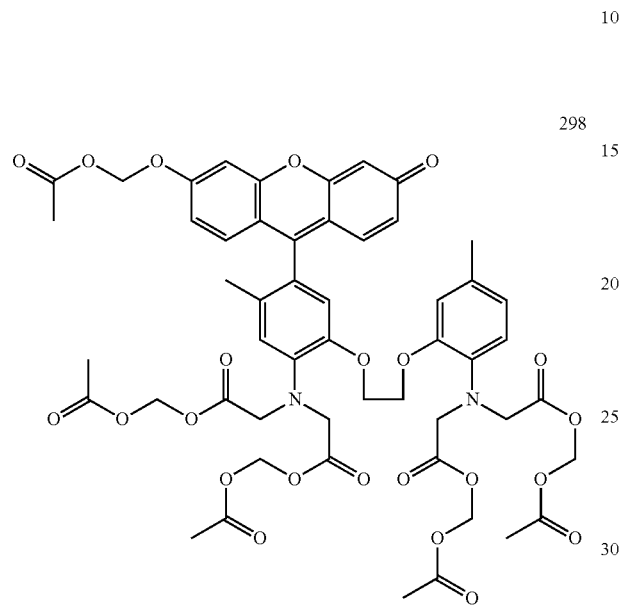

298

Example 22

Preparation of Compound 300

Compound 300 is prepared from the reaction of Compound 286 with acetic anhydride analogously to the procedure of U.S. Pat. No. 6,162,931.

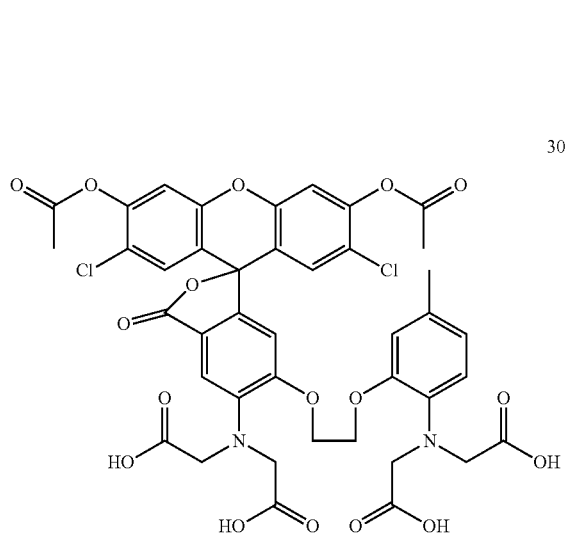

300

Example 23

Preparation of Compound 302

Compound 302 is prepared analogously to the procedure of Compound 258.

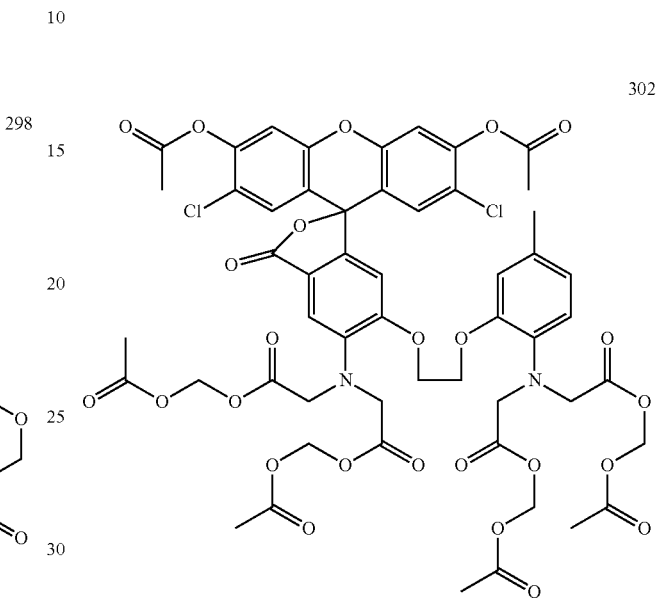

302

Example 24

Preparation of Compound 304

Compound 304 is prepared analogously to the procedure of Compound 258 by using a large excess of bromomethylacetate and base.

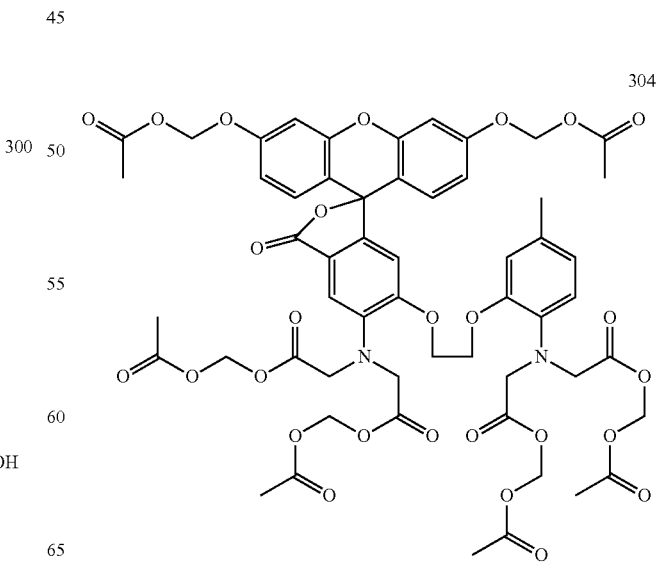

304

Example 25

Preparation of Compound 306

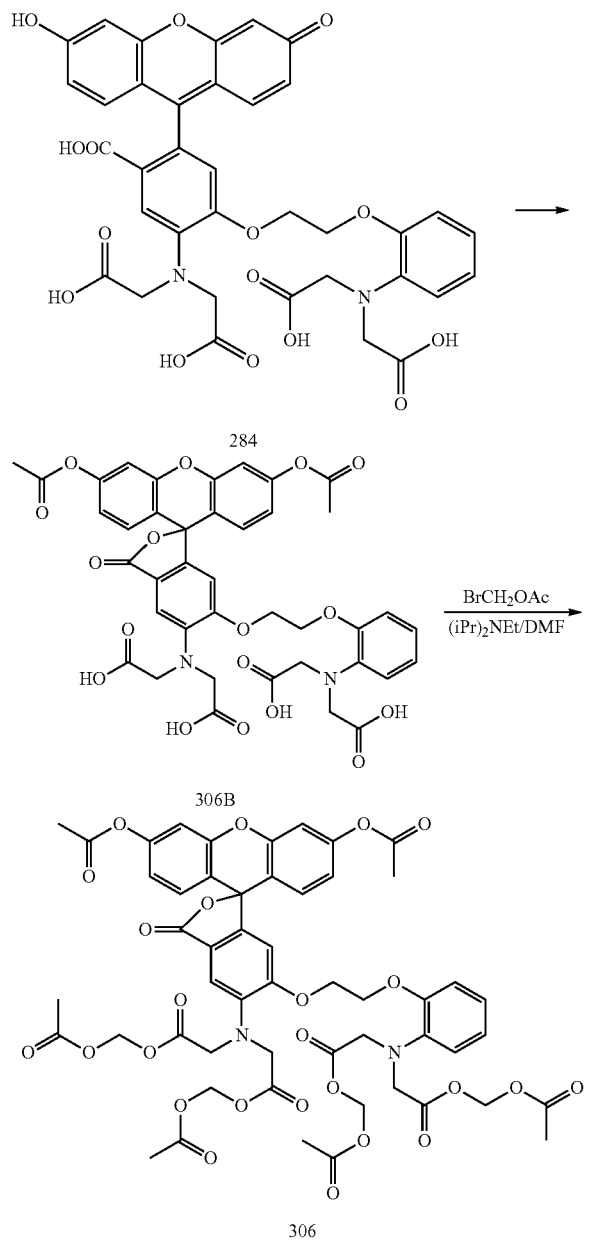

Compound 284 (350 mg) is heated at 80° C. with Ac₂O (5 mL) and pyridine (0.1 mL) until Compound 284 is completely consumed (10 to 30 min). The solution is cooled to room temperature. The reaction mixture is poured into ice water, and carefully adjusted to pH=4-5. The aqueous mixture is titrated with dioxane to give a precipitate that is collected by filtration. The resulting mixture is first air-dried, and further vacuum-dried in a desiccator with P₂O₅ for 12 h to yield crude Compound 306 B that is directly used for next step reaction.

The crude Compound 306B is converted into Compound 306 analogously to the procedure of Compound 258.

Example 26

Preparation of Compound 308

Compound 308 is prepared analogous to the procedure of Compound 275.

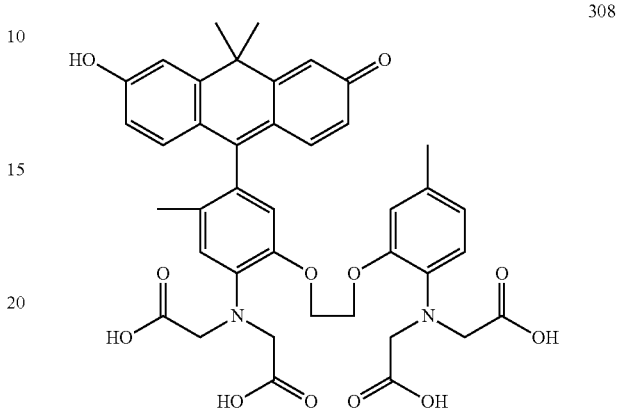

Example 27

Preparation of Compound 310

Compound 310 is prepared analogous to the procedure of Compound 275.

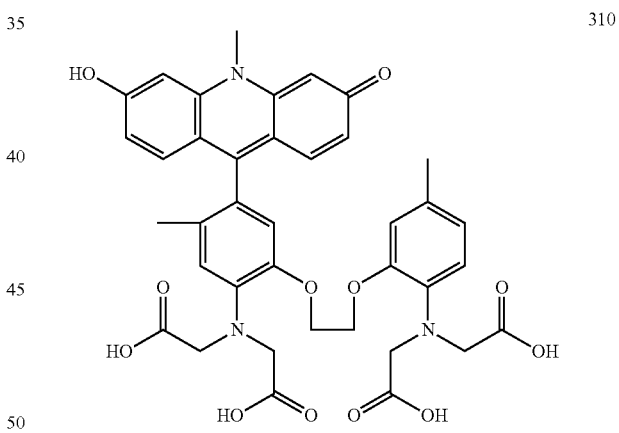

Example 28

Spectral Properties of the Fluorescent Indicators

Figure 13:
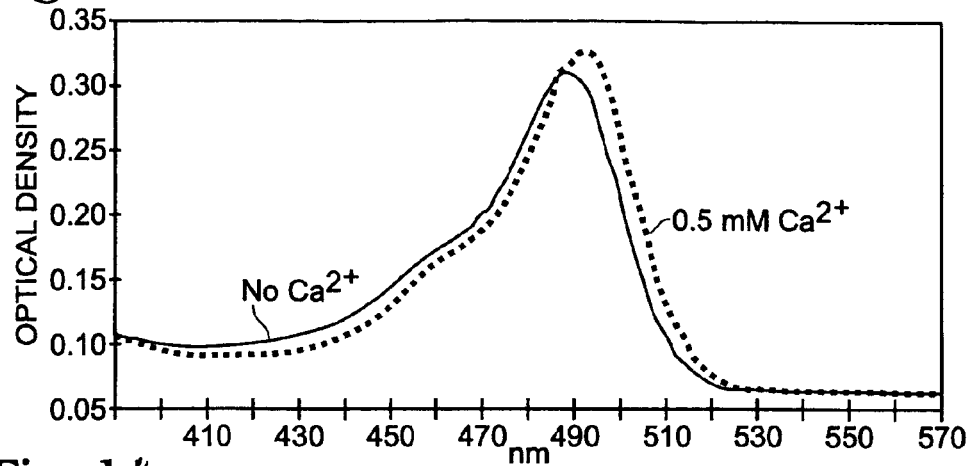
FIG. 13. The absorption spectra of Compound 284 in the presence of 0.5 mM $Ca^{2+}$ and in the absence of $Ca^{2+}$ (as described in Example 28).
Figure 14:
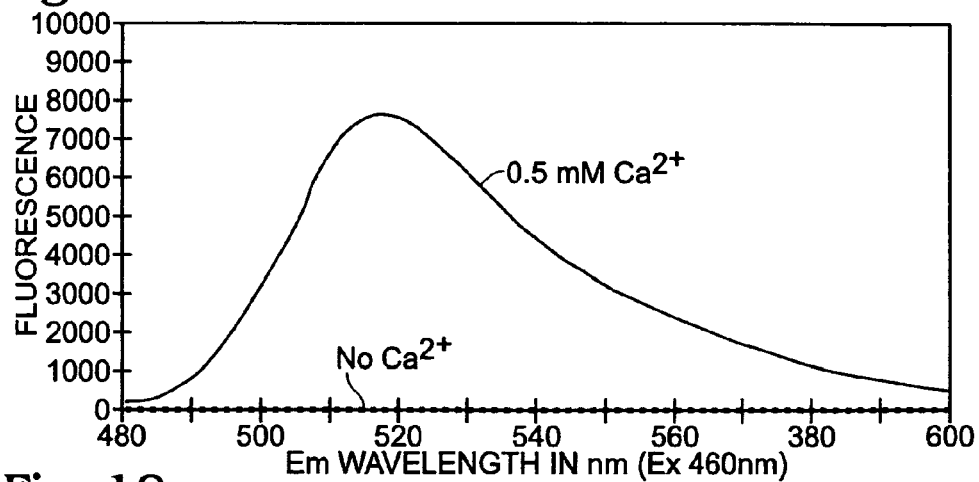
FIG. 14. The calcium-dependent fluorescence spectra of Compound 284 in the presence of 0.5 mM $Ca^{2+}$ and in the absence of $Ca^{2+}$ ion with fluorescence excitation at 460 nm, as described in Example 28.

The absorbance and fluorescence properties of a representative indicator in the presence and absence of Ca²⁺ are shown in FIGS. 13 and 14, using Compound 284. The calcium binding has little effect on the absorption spectra, as shown in FIG. 13. However, the indicator compounds of the present invention demonstrate fluorescence that is strongly enhanced by Ca²⁺ binding, as shown in FIG. 14. Additionally, Ca²⁺ binding has little effect on the wavelengths of peak excitation or emission. Specifically, 200 µL of 5 µM of compound 284 in 100 mM KCl with 30 mM Tris buffer in the presence and absence of 0.5 mM calcium is measured for absorption spectra using Spectra Max while the fluorescence spectra (excitation at 460 nm) is measured with Gemini fluorescence microplate reader. The indicators of the invention demonstrate substantially similar spectral responses to calcium binding.

Example 29

Calcium Responses of the Fluorescent Indicators Measured Using a Fluorescence Microscope Cells expressing a GPCR of interest that signals through calcium are pre-loaded with a selected indicator that has been functionalized with acetoxy methyl ester groups (or AM esters), such as for example Compounds 258, 294, 296, 298, 302, 304 and 306. Specifically, HEK-293 cells are plated at 50,000 cells per 100 µL per well in DMEM with 5% FBS and 1% L-glutamine in a 96-well black wall/clear bottom Costar plate, incubated in 5% $CO_2$, 37° C. incubator overnight. The Growth medium is removed, and 100 µL/well of 1-8 µM Fluo-3, AM, Fluo-4 AM, Compounds 258, 294, 296, 298, 302, 304, 306 or 365 in Hanks and HEPES buffer (HHBS) is added into the cells, incubated in 5% $CO_2$, 37° C. incubator for 1 hr. The cells are washed with 200 µL HHBS buffer twice, and then replaced with 100 HHBS. Images are taken using fluorescence microscope (Olympus, IX 71) with FITC filter at 20 ms exposure time. The indicators of the invention remain substantially photostable and permit fluorescence imaging of the cells.

Figure 15:
FIG. 15. Intracellular $Ca^{2+}$ response of the fluorescent indicator Fluo-3 AM when measured by a fluorescence microscope, as described in Example 29.
Figure 16:
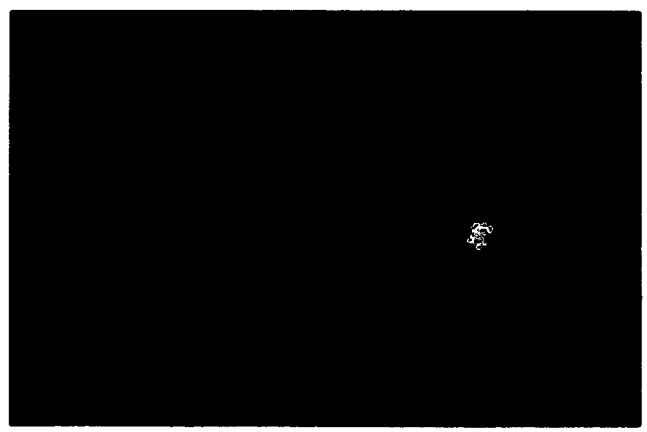
FIG. 16. Intracellular $Ca^{2+}$ response of the fluorescent indicator Fluo-4 AM when measured by a fluorescence microscope, as described in Example 29.
Figure 17:
FIG. 17. Intracellular $Ca^{2+}$ response of the fluorescent indicator Compound 365 when measured by a fluorescence microscope, as described in Example 29.

Representative fluorescence images for the indicators Fluo-3 AM (where $R^2$ and $R^5$ are chloro) and Fluo-4 AM (where $R^2$ and $R^5$ are fluoro) are provided in FIGS. 15 and 16, respectively. The fluorescence image for cells loaded with Compound 365 is provided in FIG. 17. Compound 365 is loaded into cells much faster than either Fluo-3 AM or Fluo-4 AM. In addition, Compound 365 is brighter than both Fluo-4 AM and Fluo-3 AM.

Example 30

Calcium Responses of the Fluorescent Indicators Measured Using a Microplate Reader Equipped with an Automated Liquid Handling System Calcium flux assays are preferred methods in drug discovery for screening G protein coupled receptors (GPCR). The fluorescent indicators of the invention provide a homogeneous fluorescence-based assay for detecting the intracellular calcium mobilization. Cells expressing a GPCR of interest that signals through calcium are pre-loaded with the indicator AM esters (such as Fluo-3 AM, Fluo-4 AM, Compounds 258, 294, 296, 298, 302, 304, 306 and 365) which can cross cell membrane. Once inside the cell, the lipophilic blocking groups are cleaved by non-specific cell esterase, resulting in a negatively charged fluorescein dye that is well-retained in cells, and its fluorescence is greatly enhanced upon binding to calcium. When the sample cells are stimulated with screening compounds, the receptor triggers a release of intracellular calcium, which then greatly increases the fluorescence of the intracellular indicators. The combination of long wavelength fluorescence properties, high sensitivity, and often a >100 times increase in fluorescence upon binding with calcium make the disclosed indicators well-suited for measurement of cellular calcium.

Figure 18:
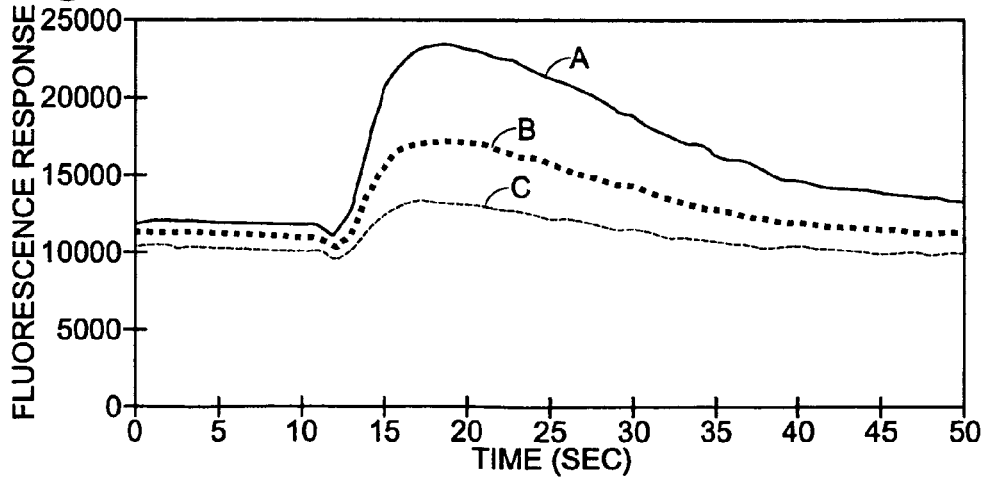
FIG. 18. The intracellular $Ca^{2+}$ response of selected fluorescent calcium indicators as measured by a fluorescence microplate reader that is equipped with an automated liquid handling system, as described in Example 30.

Specifically, CHO cells stably transfected with muscarinic receptor 1 are plated at 60,000 cells per 100 µl per well in F12 with 5% FBS and 1% L-glutamine in a 96-well black wall/clear bottom Costar plate, incubated in 5% $CO_2$, 37° C. incubator overnight. The growth medium is removed and the cells are incubated with 100 µL/well of 1-8 µM Fluo-3 AM, Fluo-4 AM, and one of Compounds 258, 294, 296, 298, 302, 304, 306 or 365 in Hanks and HEPES buffer with 2.5 mM probenecid for 1 hour at room temperature. Carbachol (50 µl/well) is added by NOVOstar (BMG LabTech) or FLIPR (Molecular Devices) to achieve the final desired concentration. A representative comparison is shown in FIG. 18.

Compound 365 (in which substituents $R^1$, $R^2$, $R^5$ and $R^6$ are all hydrogen) is loaded into cells much faster than Fluo-3, AM (in which $R^2$ and $R^5$ are chloro) and Fluo-4 AM (in which $R^2$ and $R^5$ are fluoro). In addition, Compound 365 (Curve A) demonstrates 2 times the fluorescence intensity of Fluo-4 AM (Curve B) and 4 times the fluorescence intensity of Fluo-3 AM (Curve C).

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

What is claimed is:

1. A method of monitoring intracellular calcium, wherein the method comprises:

a) contacting a sample comprising a cell with a compound;

b) incubating the sample for a time sufficient for the compound to be loaded into the cell and an indicator compound to be generated intracellularly;

c) illuminating the sample at a wavelength that generates a fluorescence response from the indicator compound;

d) detecting a fluorescence response from the indicator compound; and e) correlating the fluorescence response with the presence of intracellular calcium;

wherein the compound is described by one of the following formulae:

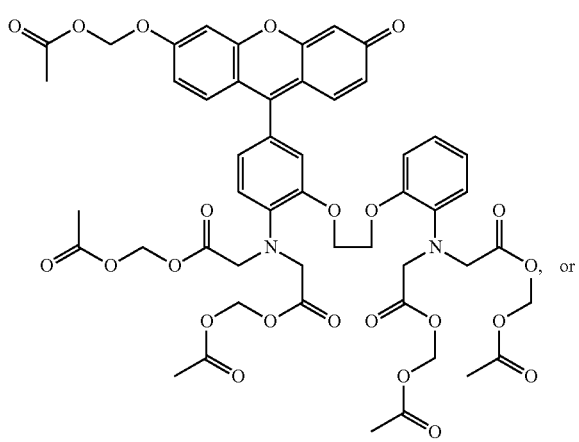

-continued

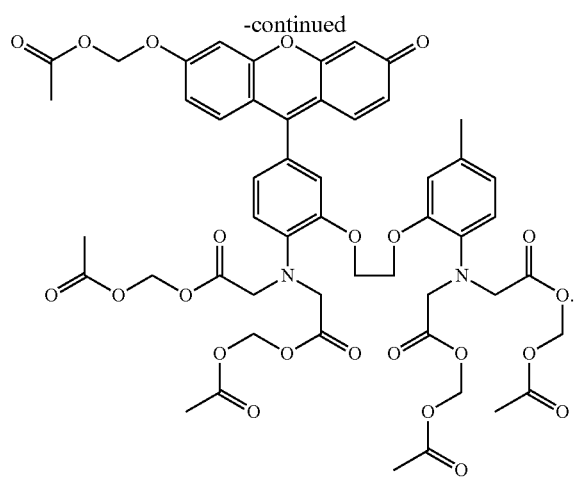

2. The method according to claim 1, wherein the compound is described by the following formula:

3. The method according to claim 1, wherein the compound is described by the following formula:

4. The method according to claim 1, wherein the method further comprises correlating the fluorescence response with intracellular calcium ion concentration.

5. The method according to claim 1, wherein the method further comprises monitoring the fluorescence response to detect a change and correlating the change in the fluorescence response with a change in intracellular calcium ion concentration.

6. The method according to claim 1, further comprising:
exposing the cell to a stimulus which modulates an ion channel in the cell;
monitoring changes in the intensity of the fluorescence response from the indicator compound; and
correlating the changes in fluorescence intensity with changes in intracellular calcium levels.

7. The method according to claim 1, further comprising:
exposing the cell to a stimulus which modulates a G protein-coupled receptor in the cell;
monitoring changes in the intensity of the fluorescence response from the indicator compound; and
correlating the changes in fluorescence intensity with changes in intracellular calcium levels.

8. The method according to claim 1, wherein the sample further comprises an agent suspected of modulating intracellular calcium ions.

9. The method according to claim 1,
further comprising adding a cell-impermeant and non-fluorescent dye to the sample.

10. A method of screening for modulation of intracellular calcium ions, the method comprising:
contacting a sample comprising a cell with a compound and a test agent;
incubating the sample for a time sufficient for the compound to be loaded into the cell and an indicator compound to be generated intracellularly;
illuminating the sample at a wavelength that generates a fluorescence response from the indicator compound;
detecting a fluorescence response from the indicator compound;
correlating the fluorescence response with the presence of intracellular calcium; and
determining whether the test compound modulates intracellular calcium ions;
wherein the compound is described by one of the following formulae:

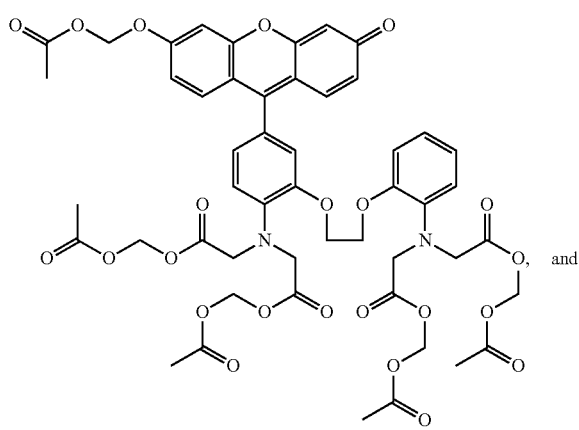

and

-continued

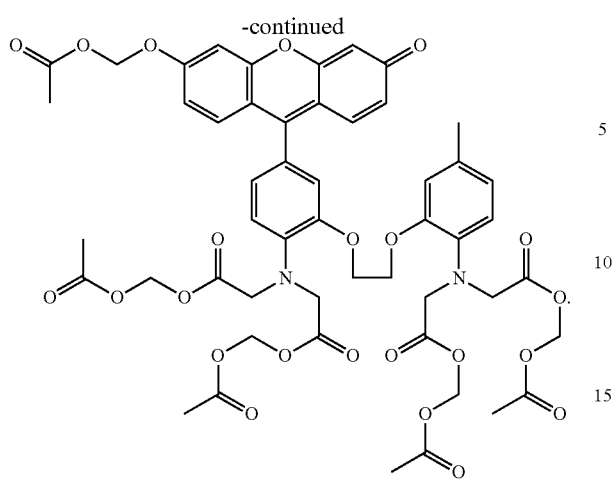

11. The method according to claim 10, wherein the compound is described by the following formula:

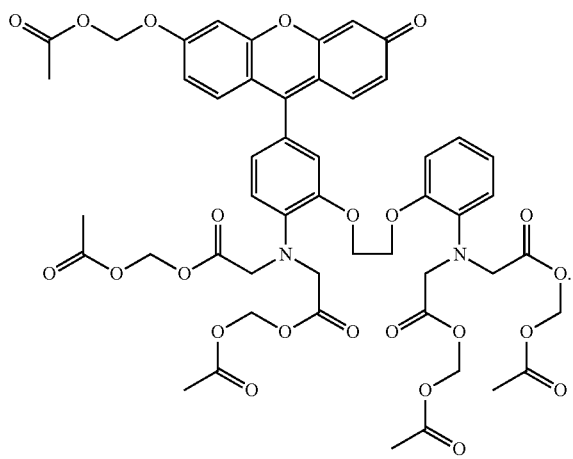 [SMILES: CC(=O)OCOC(=O)CN(CC(=O)OCOC(C)=O)c1ccccc1OCCOc1cc(-c2c3ccc(=O)cc-3oc3cc(OCOC(C)=O)ccc23)ccc1N(CC(=O)OCOC(C)=O)CC(=O)OCOC(C)=O]

12. The method according to claim 10, wherein the compound is described by the following formula:

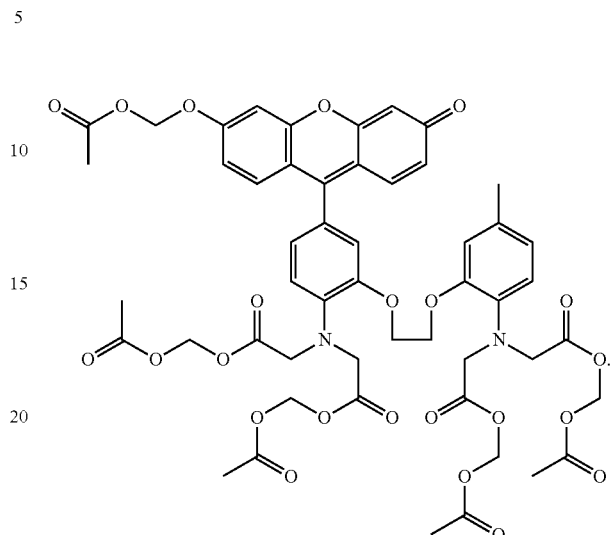

13. The method according to claim 10, further comprising correlating the fluorescence response with intracellular calcium ion concentration.

14. The method according to claim 10, wherein the test agent modulates the activity of an ion channel in the cell.

15. The method according to claim 10, wherein the test agent modulates the activity of a G-protein receptor.

16. The method according to claim 10, further comprising adding a cell-impermeant and non-fluorescent dye to the sample.

* * * * *